United States Patent [19]

Hartman et al.

[11] Patent Number: 5,416,099

[45] Date of Patent: * May 16, 1995

[54] FIBRINOGEN RECEPTOR ANTAGONISTS

[75] Inventors: George D. Hartman, Lansdale; Melissa Egbertson, Ambler; Laura M. Vassallo, Havertown; Laura A. Birchenough, Lansdale, all of Pa.

[73] Assignee: Merck & Co., Inc., Rahway, N.J.

[*] Notice: The portion of the term of this patent subsequent to Dec. 21, 2010 has been disclaimed.

[21] Appl. No.: 169,904

[22] Filed: Dec. 20, 1993

Related U.S. Application Data

[63] Continuation-in-part of Ser. No. 821,116, Jul. 15, 1992, Pat. No. 5,272,158, which is a continuation-in-part of Ser. No. 784,484, Oct. 29, 1981, abandoned.

[51] Int. Cl.[6] ............... A61K 31/445; A61K 31/44; C07D 401/06; C07D 401/14
[52] U.S. Cl. ........................... 514/323; 514/333; 514/339; 546/201; 546/256; 546/273
[58] Field of Search ............... 546/256, 201, 273; 514/333, 323, 339

[56] References Cited

U.S. PATENT DOCUMENTS

| | | | |
|---|---|---|---|
| 3,322,631 | 5/1967 | Sprague et al. | 167/65 |
| 4,010,274 | 3/1977 | Giraldi et al. | 424/274 |
| 4,122,255 | 10/1978 | Krapcho | 542/421 |
| 4,243,807 | 1/1981 | Friebe et al. | 546/232 |
| 4,313,947 | 2/1982 | Nakagawa et al. | 424/248.54 |
| 4,622,331 | 11/1986 | Jozic | 514/331 |
| 5,030,654 | 7/1991 | Barnish et al. | 514/510 |
| 5,260,316 | 11/1993 | Van Duzer et al. | 514/309 |

OTHER PUBLICATIONS

Sugimoto et al. J. Med. Chem. 27(10), (1984), 1300-5.

*Primary Examiner*—Raymond Henley, III
*Assistant Examiner*—Phyllis G. Spivack
*Attorney, Agent, or Firm*—Richard S. Parr; Melvin Winokur; Joseph F. DiPrima

[57] ABSTRACT

Fibrinogen receptor antagonists of the formula:

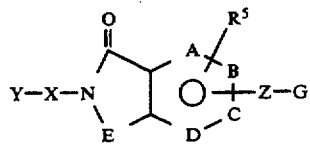

are disclosed for use in inhibiting the aggregation of blood platelets.

wherein G is:

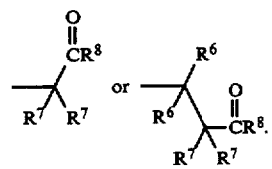

6 Claims, No Drawings

FIBRINOGEN RECEPTOR ANTAGONISTS

CROSS-REFERENCE TO RELATED APPLICATIONS

This application is a continuation-in-part patent application of U.S. Ser. No. 07/821,116, filed Jan. 15, 1992, now U.S. Pat. No. 5,272,158, which is a continuation-in-part patent application of U.S. Ser. No. 07/784,484, filed Oct. 29, 1991, abandoned.

FIELD OF THE INVENTION

This invention relates to the discovery of fibrinogen receptor antagonists of Formula I for use in inhibiting the binding of fibrinogen to blood platelets and inhibiting the aggregation of blood platelets when administered to mammals, preferably humans.

BACKGROUND OF THE INVENTION

The interaction of platelets with the coagulation and fibrinolytic systems in the maintenance of hemostasis may become pathogenic, requiring prevention and treatment. The fibrinogen receptor antagonists of Formula I are useful in treating various diseases related to platelet aggregation and fibrin formation.

An interest in platelet inhibitors has reemerged as a result of a better understanding of the role of platelets and thrombosis in the pathogenesis of vascular disease, including unstable angina, acute myocardial infarction and stroke.

Platelets are cell-like a nucleated fragments, found in the blood of all mammals which participate in blood coagulation. Fibrinogen is a glycoprotein present as a normal component of blood plasma. Fibrinogen participates in platelet aggregation and fibrin formation in the blood clotting mechanism. Platelets are deposited at sites of vascular injury where multiple physiological agonists act to initiate platelet aggregation culminating in the formation of a platelet plug to minimize blood loss. If the platelet plug occurs in the lumen of a blood vessel, normal blood flow is impaired.

Platelet membrane receptors are essential in the process of platelet adhesion and aggregation. Interaction of fibrinogen with a receptor on the platelet membrane complex IIb/IIIa is known to be essential for normal platelet function.

Zimmerman et al., U.S. Pat. No. 4,683,291, describes peptides having utility in the study of fibrinogen-platelet, platelet-platelet, and cell-cell interactions. The peptides am described as having utility where it is desirable to retard or prevent formation of a thrombus or clot in the blood.

Pierschbacher et al., U.S. Pat. No. 4,589,881, describes the sequence of an 11.5 kDal polypeptide fragment of fibronectin which embodies the cell-attachment-promoting activity of fibronectin.

Ruoslahti et al., U.S. Pat. No. 4,614,517, describes tetrapeptides which alter cell-attachment activity of cells to various substrates.

Pierschbacher et al., *Proc. Natl. Acad. Sci. USA*, Vol. 81, pp. 5985–5988, October, 1984, describe variants of the cell recognition site of fibronectin that retain attachment-promoting activity. Pierschbacher et. al. further assayed the cell attachment-promoting activities of a number of structures closely resembling the Arg-Gly-Asp-Ser peptide, and found "that the arginine, glycine, and aspartate residues cannot be replaced even with closely related amino acids, but that several amino acids can replace serine without loss of activity."

Ruoslahti et al., *Science*, Vol. 238, pp. 491–497, October 23, 1987, discuss cell adhesion proteins. They specifically state that "elucidation of the amino acid sequence of the cell-attachment domain in fibronectin and its duplication with synthetic peptides establish the sequence Arg-Gly-Asp (RGD) as the essential structure recognized by cells in fibronectin."

Cheresh, *Proc. Natl. Acad. Sci. USA*, Vol. 84, pp. 6471–6475, September 1987, describes the Arg-Gly-Asp-directed adhesion receptor involved in attachment to fibrinogen and the von Willebrand Factor.

Adams et al., U.S. Pat. No. 4,857,508, describes tetrapeptides which inhibit platelet aggregation and the formation of a thrombus.

Tjoeng et al., EP 352,249, describe platelet aggregation inhibitors which antagonize interactions between fibrinogen and/or extracellular matrix proteins and the platelet gpIIb/IIIa receptor.

Alig et al., EP 372,486, describe N-aryl beta-amino acids which inhibit fibrinogen, fibronectin and von Willebrand factor to the blood platelet fibrinogen receptor (glyco-protein IIb/IIIa).

Alig et al., EP 381,033, describe di-aryl or heteroaryl substituted alkanoic acid derivatives of a defined formula which inhibit binding of proteins to their specific receptors on cell surfaces, including fibrinogen.

Alig et al. EP 384,362, describe glycine peptides of a specified formula containing an amidine group which inhibit binding of fibrinogen to platelet fibrinogen receptors.

Horwell et al., EP 405,537, describe N-substituted cycloalkyl and polycycloalkyl alpha-substituted Trp-Phe- and phenethylamine derivatives which are useful for treating obesity, hypersecretion of gastric acid in the gut, gastrin-dependent tumors, or as antipsychotics.

It is an object of the present invention to provide fibrinogen receptor antagonists for use in inhibiting the binding of fibrinogen to blood platelets and inhibiting the aggregation of blood platelets. Another aspect of the present invention is to provide novel fibrinogen receptor antagonist compounds. Other objects of the present invention are to provide methods of inhibiting the binding of fibrinogen to blood platelets and inhibiting the aggregation of blood platelets, through the administration of novel fibrinogen receptor antagonist compounds. The above and other objects are accomplished by the present invention in the manner described below.

SUMMARY OF THE INVENTION

The present invention provides fibrinogen receptor antagonist compounds of the formula:

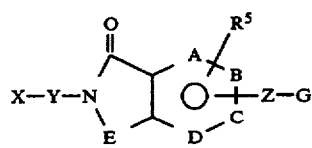

wherein G is

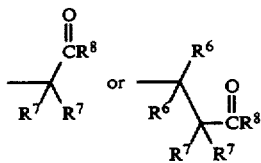

for use in inhibiting the binding of fibrinogen to blood platelets and for inhibiting the aggregation of blood platelets. The above-mentioned compounds can be used in a method of acting upon a fibrinogen receptor which comprises administering a therapeutically effective but non-toxic amount of such compound to a manmal, preferably a human. A pharmaceutical composition comprising a pharmaceutically acceptable carrier and, dispersed therein, an effective but non-toxic amount of such compound is another feature of this invention.

DETAILED DESCRIPTION OF THE INVENTION

Fibrinogen receptor antagonist compounds of Formula I are useful in a method of inhibiting the binding of fibrinogen to blood platelets and for inhibiting the aggregation of blood platelets. Fibrinogen receptor antagonists of this invention are illustrated by compounds having the formula:

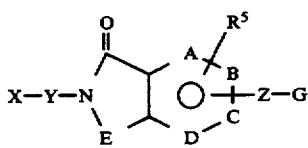

wherein G is

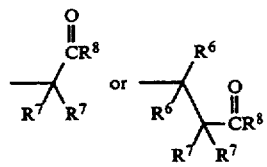

wherein:

A, B, C and D independently represent a carbon atom or a nitrogen atom;

E is
—$(CH_2)_n$—;
—$(C=C)$—;
—N—; or
—O—,
wherein n=1–4;

X is
—$NR^1R^2$,

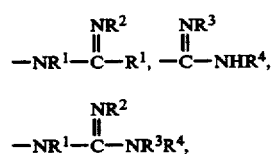

or a 4- to 10-membered mono- or polycyclic aromatic or nonaromatic ring system containing 0, 1, 2, 3 or 4 heteroatoms selected from N, O and S and either unsubstituted or substituted with $R^1$, $R^2$, $R^3$ or $R^4$, wherein $R^1$, $R^2$, $R^3$ and $R^4$ are independently selected from the group consisting of hydrogen,
$C_{1-10}$ alkyl,
aryl $C_{0-8}$ alkyl,
oxo,
thio,
amino, $C_{0-8}$ alkyl, $C_{1-3}$ acylamino $C_{0-8}$ alkyl,
$C_{1-6}$ alkylamino $C_{0-8}$ alkyl,
$C_{1-6}$ dialkylamino $C_{0-8}$ alkyl,
$C_{1-4}$ alkoxy $C_{0-6}$ alkyl,
carboxy $C_{0-6}$ alkyl, $C_{1-3}$ alkoxycarbonyl $C_{0-6}$ alkyl,
carboxy $C_{0-6}$ alkyloxy and
hydroxy $C_{0-6}$ alkyl;

Y is
$C_{0-8}$ alkyl,
$C_{0-8}$ alkyl—$NR^3$—CO—$C_{0-8}$ alkyl,
$C_{0-8}$ alkyl—$CONR^3$—$C_{0-8}$ alkyl,
$C_{0-8}$ alkyl—O—$C_{0-8}$ alkyl,
$C_{0-8}$ alkyl—$S(On)$—$C_{0-8}$ alkyl, or
$C_{0-8}$ alkyl—$SO_2$—$NR^3$—$C_{0-8}$ alkyl—,
$C_{0-8}$ alkyl—$NR^3$—$SO_2$—$C_{0-8}$ alkyl—,
$C_{1-8}$ alkyl—CO—$C_{0-8}$ alkyl;

Z is

O, S, SO, $SO_2$, $SO_2(CH_2)m$, $(CH_2)mSO_2$,

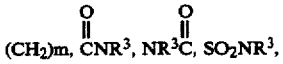

$\overset{S}{\underset{\|}{C}}NR^3$, $NR^3\overset{S}{\underset{\|}{C}}$, $NR^3SO_2$ or $CR^3=CR^4$, wherein m is 0–6;
$R^5$ is
hydrogen,
$C_{1-6}$ alkyl,
$C_{0-6}$ alkylcarboxy $C_{0-6}$ alkyl,
$C_{0-6}$ alkyloxy $C_{0-6}$ alkyl,
hydroxy $C_{0-6}$ alkyl,
aryl $C_{0-6}$ alkyl, or
halogen;
$R^6$ is
hydrogen,
$C_{1-8}$ alkyl,
aryl $C_{0-6}$ alkyl,
$C_{3-8}$ cycloalkyl $C_{0-6}$ alkyl,
$C_{0-6}$ alkylcarboxy $C_{0-6}$ alkyl, carboxy $C_{0-6}$ alkyl,
$C_{1-4}$ alkyloxy $C_{0-6}$ alkyl,
hydroxy $C_{0-6}$ alkyl,
provided that any of which $R^6$ groups may be substituted or unsubstituted independently with $R^1$ or $R^2$, and provided that, when two $R^6$ groups are attached to the same carbon, they may be the same or different;
$R^7$ is
hydrogen, fluorine,
$C_{1-8}$ alkyl,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$-alkyl,
aryl $C_{0-8}$ alkyloxycarbonylamino $C_{0-8}$ alkyl, $C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{0-6}$ alkylaminosulfonylamino $C_{0-6}$ alkyl,
aryl $C_{0-6}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl
aryl $C_{0-6}$ alkylcarbonyl $C_{0-6}$ alkyl,
$C_{1-6}$ alkylthiocarbonylamino $C_{0-6}$ alkyl
aryl $C_{0-6}$ alkylthiocarbonylamino $C_{0-6}$ alkyl wherein groups may be unsubstituted or substituted with one or more substituents selected from $R^1$ and $R^2$, and provided that when two $R^7$ groups are attached to the same carbon atom, they may be the same or different;

$R^8$ is
hydroxy,
$C_{1-8}$ alkyloxy,
aryl $C_{0-6}$ alkyloxy,
$C_{1-8}$ alkylcarbonyloxy $C_{1-4}$ alkyloxy,
aryl $C_{1-8}$ alkylcarbonyloxy $C_{1-4}$ alkyloxy, or
an L- or D-amino acid joined by an amide linkage and wherein the carboxylic acid moiety of said amino acid is as the free acid or is esterified by $C_{1-6}$ alkyl.

When substituent $R^1$, $R^2$, $R^3$, $R^4$, $R^5$, $R^6$, $R^7$, $R^8$ or Y includes the definition $C_0$, (e.g. aryl $C_0$ alkyl), the group modified by $C_0$ is not present in the substituent.

"Aryl" means a mono- or polycyclic system composed of 5-and 6- membered aromatic rings containing 0, 1, 2, 3 or 4 heteroatoms chosen from N, O or S and either unsubstituted or substituted with $R^1$.

"Alkyl" means straight or branched chain alkane, alkene or alkyne.

"Halogen" includes fluorine, chlorine, iodine and bromine.

"Oxo" means =O.
"Thio" means =S.

Under standard nomenclature used throughout this disclosure, the terminal portion of the designated side chain is described first followed by the adjacent functionallity toward the point of attachment. For example, a $C_{1-6}$alkyl substituted with $C_{1-6}$alkylcarbonylamino is equivalent to

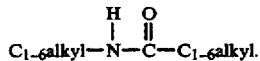

A preferred embodiment of the present invention is

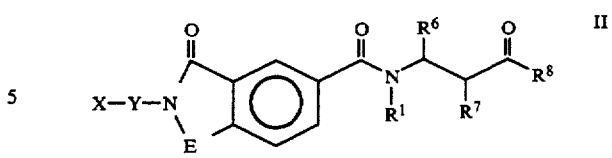

II wherein:
E is
—$(CH_2)_n$—;
—$(C=C)$—;
—N—; or
—O—,
wherein n=1-4;
X, Y, $R^1$, $R^2$, $R^3$, $R^4$, $R^6$, $R^7$ and $R^8$ are as previously defined.

A more preferred embodiment of the present invention is III wherein:

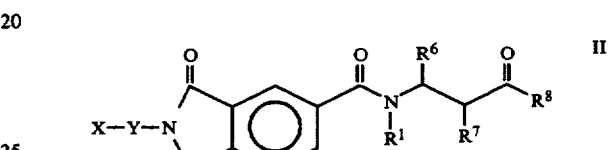

E is
—$(CH_2)_n$—;
—$(C=C)$—;
—N—; or
—O—,
wherein n=1-4;
X is
—$NR^1R^2$ or a 4- to 10-membered mono- or polycyclic aromatic or non-aromatic ring system containing 0, 1 or 2 heteroatoms chosen from N or O and either unsubstituted or substituted with $R^1$ and $R^2$, wherein $R^1$ and $R^2$ are independently chosen from:
hydrogen,
$C_{1-6}$ alkyl,
aryl $C_{0-6}$ alkyl,
carboxy $C_{0-6}$ alkyl,
hydroxy $C_{0-6}$ alkyl,
$C_{1-3}$ alkyloxy $C_{0-6}$ alkyl, or amino $C_{0-6}$ alkyl;
Y is
$C_{0-6}$ alkyl,
$C_{1-6}$ alkyl—CO—$C_{0-6}$ alkyl, or
$C_{0-6}$ alkyl—$NR_3$—CO—$C_{0-6}$ alkyl;
$R^6$ and $R^7$ are as previously defined and
$R^8$ is
hydroxy,
$C_{1-6}$ alkyloxy,
aryl $C_{1-4}$ alkyloxy, or
$C_{1-6}$ alkylcarbonyloxy $C_{1-4}$ alkyloxy.

Preferred compounds of the invention are:

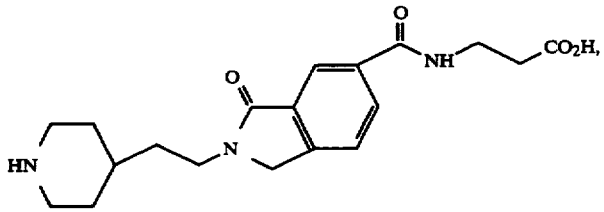

-continued
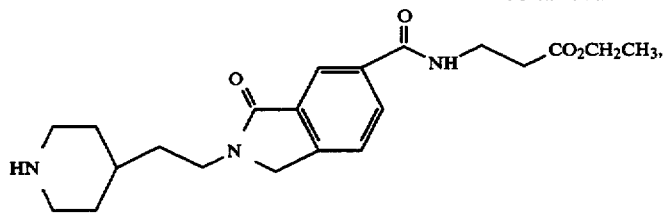
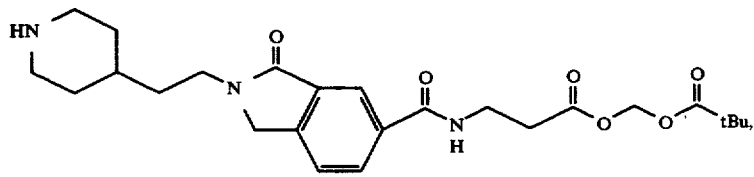
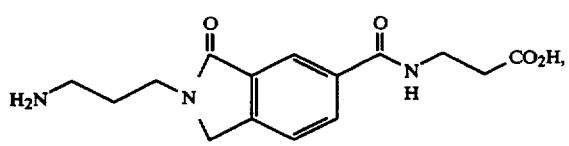
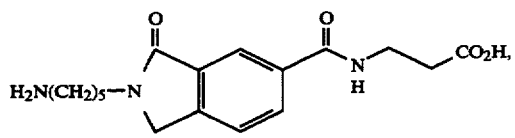
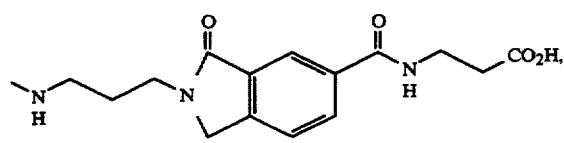
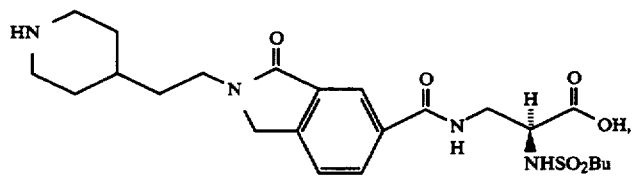
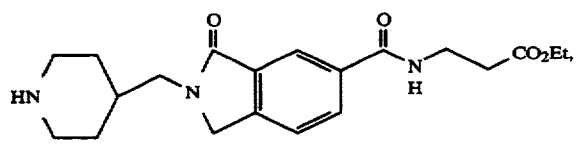
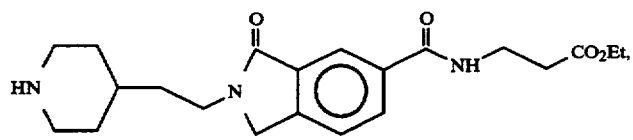
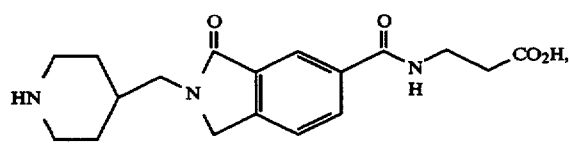

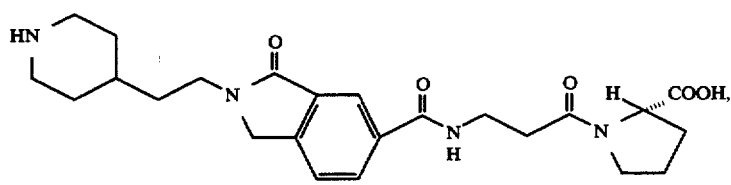
Other preferred compounds of the invention are:
Generally, compounds of the present invention can be made according to a procedure including the following steps:
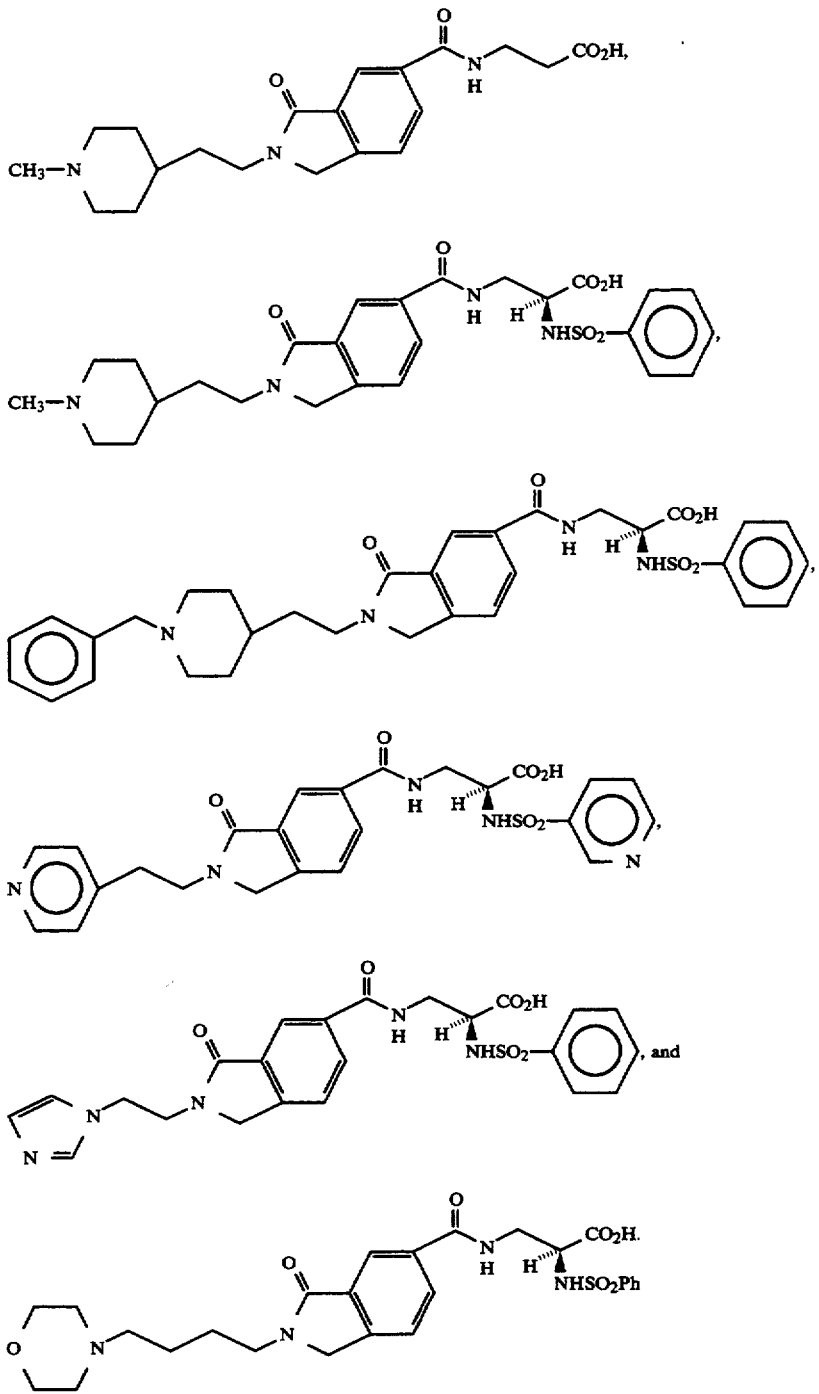

a) preparing a triflate activated aromatic group of the following general formula:

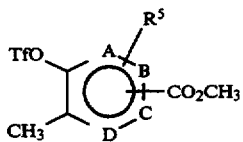

using

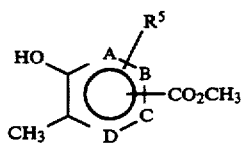

and Tf₂O;

b) inserting a carbonyl group for the triflate group using metal catalyzed carbonyl insertion, followed by trapping with methanol, to form

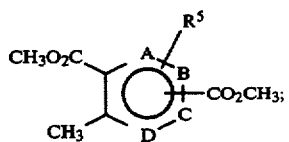

c) brominating the heterocyclic methyl group to form

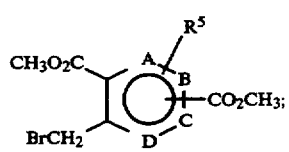

d) cyclizing with a primary amine to form

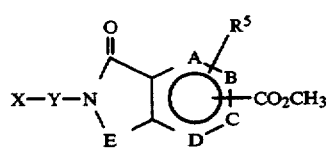

wherein X is an N-terminus protected primary amine, or a primary amine protected directly following this cyclization step;

e) converting the C-terminus ester, via hydrolysis, to an acid

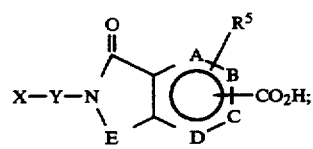

f) coupling the acid with an unsubstituted or substituted amino acid or C-terminus protected analog, or diamino acid or C-terminus protected analog, and optionally functionalizing the amino acid at the alpha- or beta-position, to form

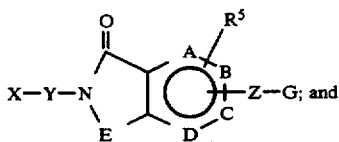

g) deprotecting the protected C-terminus and N-terminus.

Preferably the procedure involves a) preparing an activated aryl group:

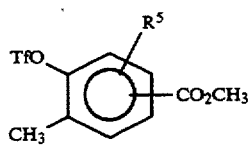

using

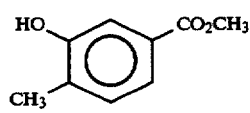

and T₂O;

b) inserting a carbonyl group for the triflate group using metal catalyzed carbonyl insertion followed by trapping with methanol to form

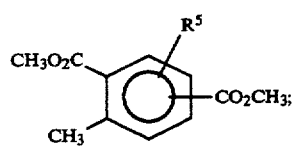

c) brominating the aryl methyl group to form

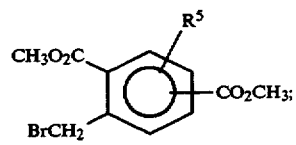

d) cyclizing with a primary amine to form

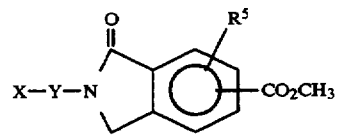

wherein X is an N-terminus protected primary amine, or a primary amine protected directly following this cyclization step;

e) converting the C-terminus ester, via hydrolysis, to an acid

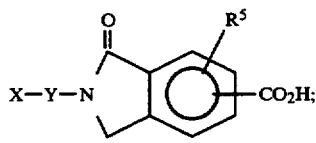

f) coupling the acid with an unsubstituted or substituted amino acid or C-terminus protected analog, or diamino acid or C-terminus protected analog, and optionally functionalizing the amino acid at the alpha- or beta-position via acylation or sulfonylation, to form

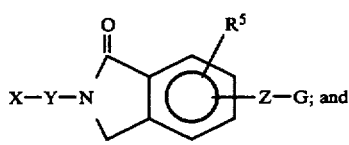

g) deprotecting the protected C-terminus and N-terminus.

An ADP-stimulated platelet aggregation assay was used to determine inhibition associated with compounds of the invention.

Human platelets were isolated from fresh blood, collected into acid citrate/dextrose by differential centrifugation followed by gel filtration on Sepharose 2B in divalent ion-free Tyrode's buffer (pH 7.4) containing 2% bovine serum albumin. Platelet aggregation was measured at 37° C. in a a Chronolog aggregometer. The reaction mixture contained gel-filtered human platelets ($2 \times 10^8$ per ml), fibrinogen (100 μg/ml), $Ca^{2+}$ (1 mM), and the compound to be tested. Aggregation was initiated by adding 10 uM ADP 1 minute after the other components had been added. The reaction was allowed to proceed for at least 2 minutes. The extent of inhibition of aggregation was expressed as the percentage of the rate of aggregation observed in the absence of inhibitor. The $IC_{50}$ is the dose of a particular compound inhibiting aggregation by 50% relative to a control lacking the compound.

Additional preferred embodiments of the invention, shown below with platelet aggregation inhibition potency data ($IC_{50}$ μM) are:

| Compound | $IC_{50}$ uM |
|---|---|
| | 0.16 |
| | 4.3 |
| | 5.7 |
| | 0.42 |
| | 1.0 |

| Compound | IC$_{50}$ uM |
|---|---|
| (structure) H$_2$N-...-N-isoindolinone-C(O)NH-CH$_2$CH$_2$-CO$_2$H | 21 |
| (structure) piperidine-CH-(CH$_2$)$_2$-N-isoindolinone-C(O)NH-CH$_2$CH$_2$-CO$_2$H | 0.92 |
| (structure) piperidine-CH-(CH$_2$)$_2$-N-isoindolinone-C(O)NH-CH$_2$-CO$_2$H | 14.0 |

The abbreviations listed below are defined as Bn, benzyl; NMM, N-methylmorpholine; HOBt, 1-hydroxybenzotriazole; EDC, 1-(3-dimethylaminopropyl)-3-ethylcarbodiimide hydrochloride; DMF, dimethylformamide; Pib, 4-(4-piperidyl)butanoyl; pTSA, para-toluenesulfonic acid; DMS, dimethylsulfide; TFA, trifluoroacetic acid; THF, tetrahydrofuran; DIBAL, diisobutylaluminum hydride; Boc (or BOC), tert-butoxycarbonyl; Cbz, benzyloxycarbonyl; Suc, succinoyl; alpine borane, β-isopinocamphenyl-9-borabicyclo[3.3.1]-nonane; TBDMS, tert-butyldimethylsilyl; Jones reagent, chromic acid; NBS, N-Bromosuccinimide; BPO, Benzoyl peroxide; PPh3, triphenyl phosphine; DMSO, Dimethylsulfoxide; Et3N, triethylamine; Tf$_2$O, triflic anhydride; DMAP, 4-dimethylaminopyridine; BOP, benzotriazol-1-yloxytris(dimethylamino)phosphonium hexafluorophosphate; PhCHO, benzaldehyde; and Boc$_2$O, di-t-butyldicarbonate; dppp, 1,3-bis(diphenylphosphino)propane; ETOH, ethyl acetate; CH$_2$Cl$_2$, methylene chloride; HOAc, acetic acid; CH$_3$OH, methanol; CHCl$_3$, chloroform.

Unless otherwise indicated, all degree values are Celsius.

The pharmaceutically acceptable salts of the compounds of Formula I include the conventional non-toxic salts or the quaternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

The compounds of Formula I are useful in inhibiting the binding of fibrinogen to blood platelets, inhibiting aggregation of blood platelets, treatment of thrombus formation or embolus formation, and in the prevention of thrombus formation or embolus formation. These compounds are useful as pharmaceutical agents for mammals, especially for humans. The compounds of this invention may be administered to patients where prevention of thrombosis by inhibiting binding of fibrinogen to the platelet membrane glycoprotein complex IIb/IIIa receptor is desired. Compounds of this invention may also be used to prevent or modulate the progress of myocardial infarction, unstable angina and thrombotic stroke, in either acute or chronic settings. In addition, they may be useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the circuit. (Gluszko et al., Amer. J. Physiol., 1987, 252:H, pp 615–621 ). Platelets released from artificial surfaces show impaired hemostatic function. Compounds of this invention may be administered to prevent adhesion.

Other applications of these compounds include prevention of platelet thrombosis, thromboembolism, reocclusion, and restenosis during and after thrombolytic therapy and prevention of platelet thrombosis, thromboembolism, reocclusion and restenosis after angioplasty of coronary and other arteries and after coronary artery bypass procedures.

The compounds of Formula I may be administered to mammals, preferably in combination with pharmaceutically-acceptable carriers or diluents, optionally with known adjuvants such as alum, in a pharmaceutical composition which is non-toxic and in a therapeutically effective amount, according to standard pharmaceutical practice. The compounds can be administered orally or parenterally, including intravenous, intramuscular, intraperitoneal, trans-dermal, subcutaneous and topical administration.

For oral use of a fibrinogen receptor antagonist according to this invention, the selected compounds may be administered, for example, in the form of tablets or capsules, or as an aqueous solution or suspension. In the case of tablets for oral use, carders which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added.

For intramuscular, intraperitoneal, subcutaneous, and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment and prevention of diseases related to platelet aggregation, fibrin formation, and thrombus and embolus formation, comprising the administration of a therapeutically effective but non-toxic amount of the compounds of Formula I, with or without pharmaceutically acceptable carriers or diluents.

Compositions of this invention include fibrinogen receptor antagonist compounds of this invention in combination with pharmacologically acceptable carriers, e.g. saline, at a pH level e.g. 7.4, suitable for achieving inhibition of platelet aggregation. The compositions may also be combined with anticoagulants such as heparin or warfarin. The compositions may also be combined with thrombolytic agents such as plasminogen activators or streptokinase in order to inhibit platelet aggregation in more acute settings. The composition may further be combined with antiplatelet agents such as aspirin. The compositions are soluble in an aqueous medium, and may therefore be effectively administered in solution.

When a compound according to Formula I is used as a fibrinogen receptor antagonist in a human subject, the daily dosage will normally be determined by the prescribing physician with the dosage generally varying according to the age, weight, and response of the individual patient, as well as the severity of the patients symptoms.

In one exemplary application, a suitable amount of compound is administered orally to a heart attack victim subsequent to angioplasty. Administration occurs subsequent to angioplasty, and is in an amount sufficient to inhibit platelet aggregation, e.g. an amount which achieves a steady state plasma concentration of between about 0.01–50 μM preferably between about 0.01–10 μM.

The present invention also includes a pharmaceutical composition comprising compounds of the present invention in combination with tissue type plasminogen activator or streptokinase. The invention also includes a method for promoting thrombolysis and preventing reocclusion in a patient which comprises administering to the patient an effective amount of compositions of the invention.

The present invention provides a method of inhibiting the binding of fibrinogen to blood platelets, inhibiting aggregation of blood platelets, treating thrombus formation or embolus formation, and in preventing thrombus formation or embolus formation in a mammal, comprising the administration of a therapeutically effective but non-toxic amount of the compounds of this invention, with or without pharmaceutically acceptable carriers or diluents.

The present invention still further provides a method of inhibiting the binding of fibrinogen to blood platelets, inhibiting aggregation of blood platelets, treating thrombus formation or embolus formation, and in preventing thrombus formation or embolus formation in a mammal, comprising the administration of a therapeutically effective but non-toxic amounts of the compounds of this invention in combination with thrombolytic agents, such as tissue plasminogen activators or streptokinase, anticoagulants such as heparin or warfarin, or antiplatelet agents such as aspirin, with or without pharmaceutically acceptable carriers or diluents.

The compounds of Formula I are prepared according to the reaction schemes set forth below.

SCHEME 1

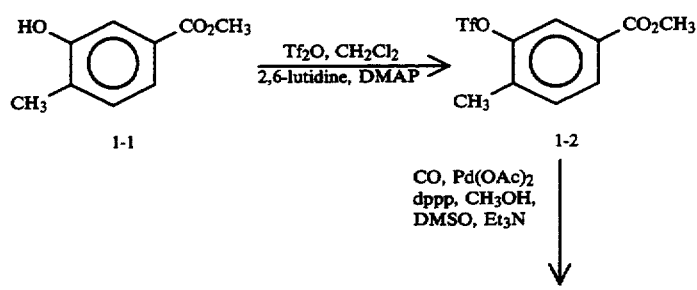

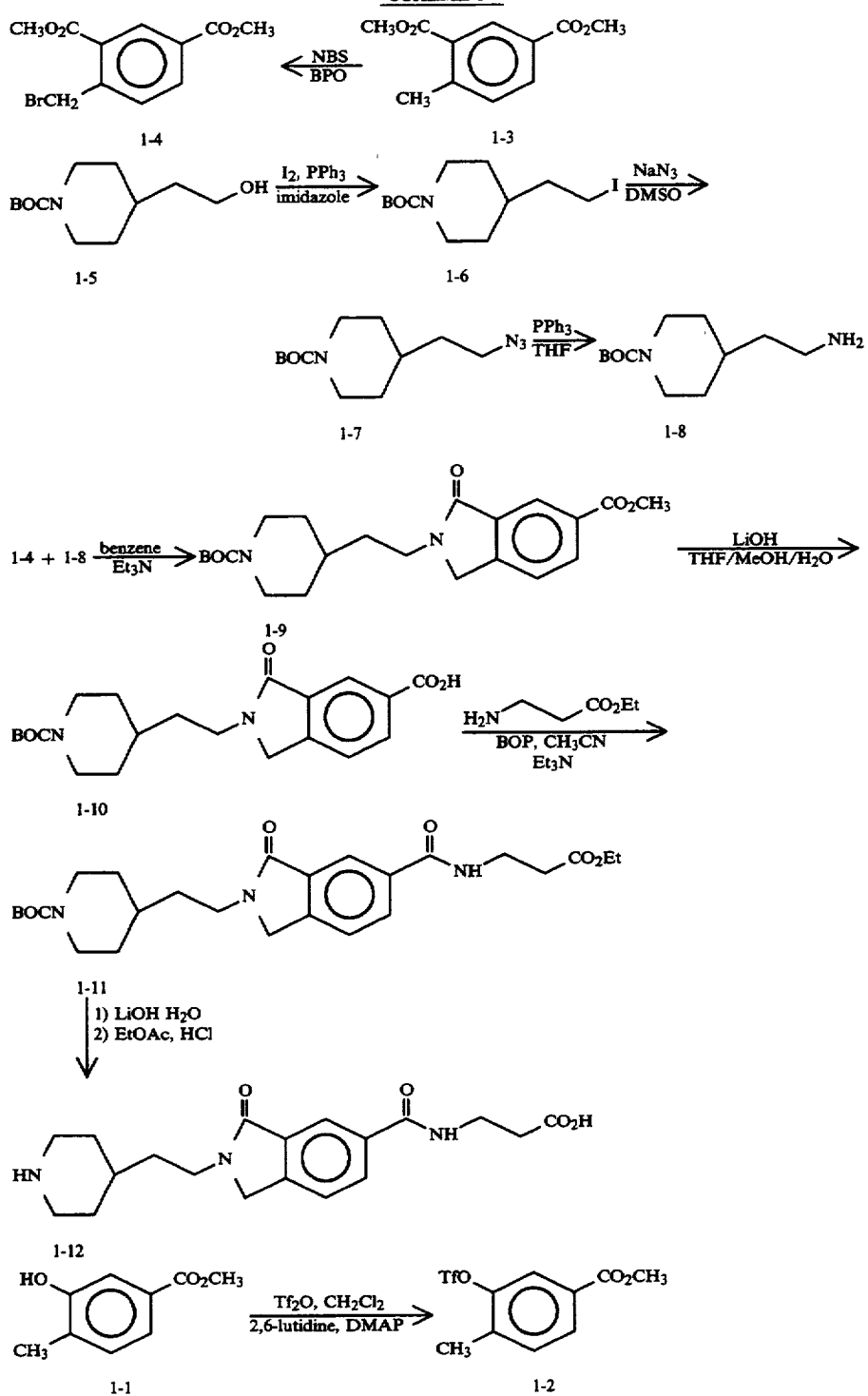

Methyl 4-methyl-3-trifluoromethanesulfonyloxybenzoate (1-2)

A solution of methyl 4-methyl-3-hydroxybenzoate (1—1) (20.0 g, 0.12 moles) [prepared from the corresponding carboxylic acid (Aldrich) by treatment with a methanolic solution of HCl gas] in $CH_2Cl_2$ (900 ml) was cooled to $-40°$ and treated successively with 2,6-lutidine (0.18 moles), DMAP (2.9 g, 0.024 moles) and trifluoromethylsulfonyl anhydride (0.18 moles). The cooling bath was then removed and the resulting mixture was stirred at ambient temperature for 2.0 hours. The solvent was then removed and the residue was purified by flask chromatography on silica eluting with hexane(8-)/EtOAc(2) to provide pure 1-2, $R_f 0.35$.

¹H NMR (300 MHz, CDCl₃) δ 2.18 (3H, s), 3.85 (3H, s), 7.30 (1H, d), 7.84 (1H, s), 7.90 (1H, d).

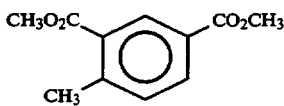

Dimethyl 4-methylbenzene-1,3-dicarboxylate (1-3)

A solution of 1-2 (30.0 g, 0.121 moles) in methanol/300 ml was treated successively with DMSO (180 ml), triethylamine (0.278 moles), palladium acetate (0.807 g, 3.6 mmoles) and dppp (1.48 g, 3.6 mmoles) as the reaction turned to a clear dark brown solution. Carbon monoxide was then bubbled through the reaction mixture for 3 minutes and the resulting mixture was heated at reflux, while continuing to bubble CO. After refluxing for 4 hours the reaction mixture was concentrated and the resulting brown oil was purified by flask chromatography on silica gel eluting with hexane(90-)/EtOAc(10) to provide pure 1-3.

¹H NMR (300 MHz, CDCl₃) δ 2.69 (3H, s), 3.95 (3H, s), 3.96 (3H, s), 7.37 (1H, d), 8.09 (1H, dd), 8.60 (1H, d).

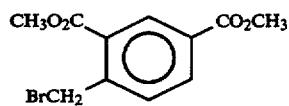

Dimethyl 4-bromomethylbenzene-1,3-dicarboxylicacid (1-4)

A solution of 1-3 (1.35 g, 6.5 mmole) in CHCl₃ (20 ml) was treated with dibenzoyl peroxide (0.078 g, 3.5 mmol) and N-bromosuccinimide (NBS) (1.1 g, 6.5 mmole) and the resulting solution was heated at reflux for 2 hours.

The cooled reaction mixture was concentrated, taken up in CCl₄, filtered and the filtrate was concentrated to give 1-4 as a tan solid. R$_f$0.5 [silica gel, hexane(70-)/EtOAc(30)].

Preparation of Boc-4-Piperidine-2-ethanol (1-5)

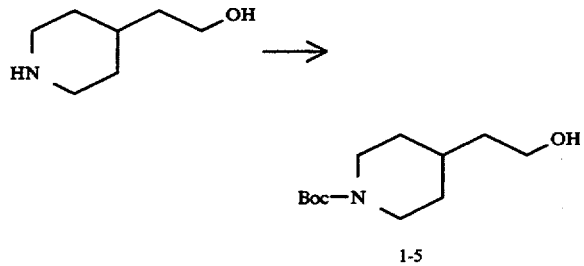

4-Piperidine-2-ethanol (Aldrich) (130 g, 1.0 mole) was dissolved in 700 mL dioxane, cooled to 0° C. and treated with 3N NaOH (336 mL, 1.0 mole), and di-t-butyldicarbonate (221.8 g, 1.0 mole). The ice bath was removed and the reaction stirred overnight. The reaction was concentrated, diluted with water and extracted with ether. The ether layers were combined, washed with brine, dried over MgSO₄, filtered and evaporated to give 1-5.

R$_f$=0.37 in 1:1 EtOAc/Hexanes, ninhydrin stain.

¹H NMR (300MHz, CDCl₃ ) a 4.07 (bs, 2H), 3.7 (bs, 2H), 2.7 (t, J=12.5 Hz, 2H), 1.8-1.6 (m, 6H), 1.51 (s, 9H), 1.1 (ddd, J=4.3, 12.5, 12 Hz, 2H).

Boc-4-piperidine-2-ethyl iodide (1-6)

Boc-4-piperidine-ethanol (1-5) (10.42 g, 0.048 mole was dissolved in 400 ml benzene and imidazole (4.66 g, 0.068 moles) and triphenylphosphine (15.24 g, 0.05 moles) were added at room temperature. After 6 hours the reaction mixture was filtered and the filtrate was evaporated to give a dark residue. This was purified by flash chromatography on silica gel eluting with 10% EtOAc-hexanes to give 1-6 as a yellow oil.

Boc-4-piperidine-2-ethylazide (1-7)

To 1-6 (27.9 g, 0.082 moles) dissolved in DMSO (400 ml) was added sodium azide (5.01 g, 0.086 moles) at room temperature and the resulting solution was heated at 65° for 2 hours. The cooled reaction mixture was diluted with 250 ml EtOAc, extracted with 2×100 ml portions of water 2×50 ml portions of brine and then dried (MgSO₄). Solvent removal provided 1-7 as a pale yellow oil, R$_f$0.5 (silica gel, 70% acetone/hexane).

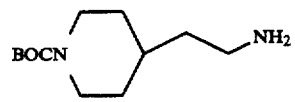

Boc-4-piperidine-2-ethylamine( 1-8)

To a solution of 1-5 (19.3 g, 0.076 moles) in THF (400 ml)/H₂O (195 ml) was added triphenylphosphine (80.0 g, 0.305 moles) in one portion at room temperature. This was stirred at room temperature 3 hours and the organic solvents were then removed in vacuo. The residue was acidified to pH 2 with 10% KHSO₄ solution and this was extracted 4×100 ml portions of EtOAc. The organic extract was extracted with 2×100 ml portions of 10% KHSO₄ and the aqueous phases were combined and the pH was adjusted to 10 with 2N NaOH. This solution was extracted with 4×200 ml portions of CH₂Cl₂. These were combined, dried (MgSO₄) and the solvent was removed to give 1-8 as an oil. R$_f$0.3 (silica gel, eluting with 10% CH₃OH in CHCl₃/NH₃).

¹H NMR (300 MHz, CDCl₃) δ 4.05 (broad, 2H), 2.72 (t, J=7.2Hz, 2H), 2.62 (m, 2H), 1.64 (d, J=12.2Hz, 2H), 1.43 (s, 9H), 1.42-1.32 (m, 5H), 1.09 (m, 2H).

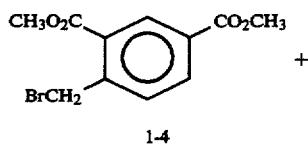

-continued

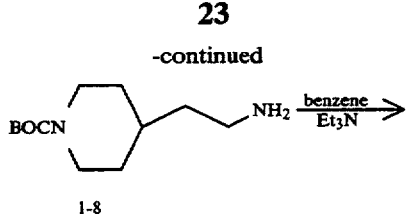

1-8

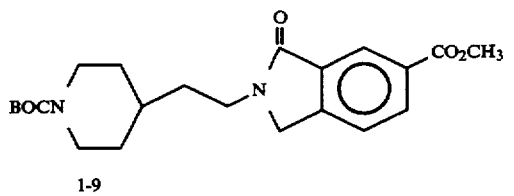

1-9

Methyl-1H-Isoindole-5-carboxylate, 2,3-dihydro-N-[2(4-N-t-butyloxycarbonylpiperidinyl)ethyl]-3-oxo (1–9)

A solution of 1-4 (1.0 g, 3.5 mmoles) in benzene (5 ml) was treated with 1-8. (0.80 g, 3.5 mmol) and triethylamine (0.49 ml, 3.5 mmol) and the reaction mixture was heated at reflux for 3 hours. The solvent was removed and the residue was taken up in EtOAc, washed in 10% KHSO$_4$ solution, H$_2$O, brine and dried. Solvent removal gave a residue that was purified by flash chromatography on silica gel eluting with hexane( 1 )/EtOAc( 1 ) to give pure 1–9.

R$_f$0.2 (silica gel, hexane(1)/EtOAc(1)). $^1$H NMR (300 MHz, CDCl$_3$) δ 1.08 (2H, m), 1.43 (9H, s) 1.61 (4H, m), 1.73 (2H, bd), 2.62 (2H, bt), 3.64 (2H, t), 3.93 (3H, s), 4.07 (2H, m), 4.40 (2H, s), 7.50 (1H, d), 8.21 (1H, dd), 8.47 (1H, d).

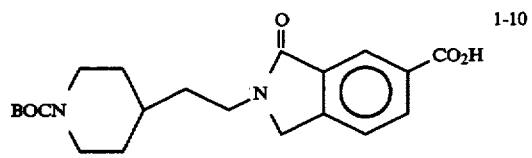

1-H-Isoindole-5-carboxylic acid, 2,3-dihydro-N-[2-(4-N-t-butyloxycarbonylpiperidinyl)ethyl]-3-oxo (1–10)

A solution of 1-9 (0.43 g, 1.12 mmole) in THF (1)/MeOH(1)/H$_2$O(1) (9 ml) was treated at room temperature with LiOH·H$_2$O(0.235 g, 5.6 mmol) and the resulting solution was stirred for 4 hours. The reaction mixture was then diluted with EtOAc (75 ml)/10% KHSO$_4$ solution (30 ml) and the organic phase was separated and dried (Na$_2$SO$_4$). Solvent removal gave the desired acid 1-10. R$_f$ 0.5 (silica gel, CH$_2$Cl$_2$ (9)/MeOH (0.5)/HOAc(0.5)).

$^1$H NMR (300 MHz, CDCl$_3$) δ 1.12 (2H, m), 1.42 (9H, s), 1.60 (3H, m), 1.71 (2H, bd), 2.63 (2H, bt), 3.68 (2H, t), 4.08 (2H, m), 4.40 (2H, s), 7.03 (1H, d), 8.28 (1H, dd), 8.60 (1H, s).

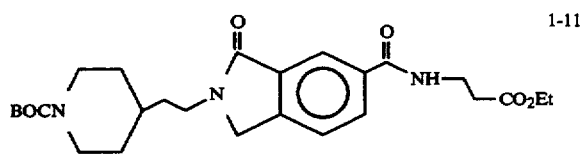

1-H-Isoindole-5-carboxamide, 2,3-dihydro-N-[2-(carboetboxy)ethyl]-2-[2-(4-N-t-butyloxycarbonylpiperidinyl)ethyl]-3-oxo (1–11)

A solution of 1-10 (0.35 g, 0.94 mmole), triethylamine (0.40 ml, 2.82 mmol), and p-alanine ethyl ester (0.22 g, 1.41 mmol) (Aldrich) in CH$_3$CN (5 ml) was treated at room temperature with BOP (1.2 mmoles) reagent and the resulting solution was stirred for 16 hours.

The solvent was removed and the residue was taken up in EtOAc, washed with H$_2$O, 10% KHSO$_4$ solution, brine and dried (Na$_2$SO$_4$). Solvent removal gave a residue that was purified by flash chromatography on silica gel eluting with hexane(20)/EtOAc(80) to give pure 1–11 as a clear oil.

$^1$H NMR (300 MHz, CDCl$_3$) δ 1.10–1.30 (3H, m), 1.44 (9H, s), 1.60 (3H, m), 1.75 (2H, bd), 2.63 (4H, m), 3.70 (4H, m), 4.05–4.20 (4H, m), 4.38 (2H, s), 7.50 (1H, d), 8.08 (2H, m).

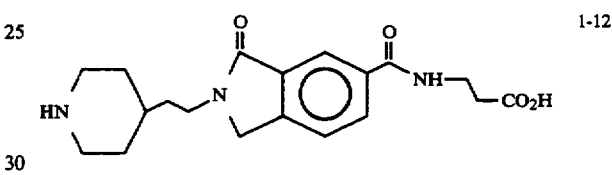

1-H-Isoindole-5-carboxamide, 2,3-dihydro-N-(2-carboxyethyl)-2-[2-(4-piperidinyl)ethyl]-3-oxo (1–12)

A solution of 1-11 (0.32 g, 0.68 mmol) in THF(1)/MeOH-(1)/H$_2$O(1) (9 ml) was treated with LiOH·H$_2$O (0.14 g, 3.4 mmoles) at room temperature for 1.0 hr. The solvent was then removed and the residue was taken up in EtOAc and washed with 10% KHSO$_4$ solution, brine and dried (Na$_2$SO$_4$). Solvent removal gave the desired acid. R$_f$0.3 (silica gel, CHCl$_3$ (9)/MeOH (0.5)/HOAc (0.5)).

This acid (0.30 g, 0.68 mmole) was dissolved in CH$_2$Cl$_2$ and anisole (150 μl) was added. This was cooled to −15° C. and trifluoroacetic acid (3 ml) was added and the resulting mix stirred for 0.5 hours. The solvent was removed and the residue purified by flash chromatography on silica gel eluting with EtOH (9)/NH$_4$OH (1.2)/H$_2$O (1.2) to provide pure 1–12.

$^1$H NMR (300 MH$_3$, D$_2$O) δ1.30 (7H, m), 1.50–1.70 (3H, m), 1.83 (2H, bd), 2.38 (2H, t), 2.80 (2H, dt), 3.27 (2H, bd), 3.50 (4H, m), 4.42 (2H, s), 7.51 (1H, d), 7.83 (2H, m).

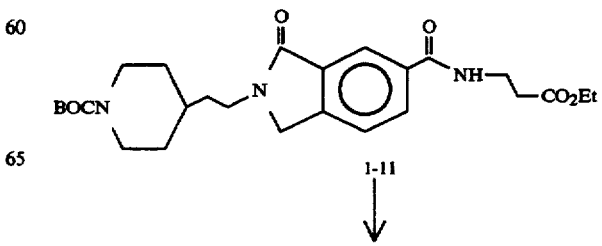

1-11

↓

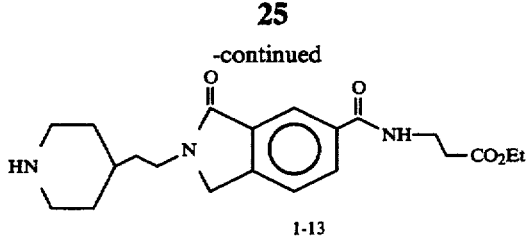

1-13

1-H-Isoindole-5-carboxamide,
2,3-dihydro-N-[2-(carboethoxy)ethyl]-2-[2-(4-piperidinyl)ethyl)ethyl]-3-oxo (1-13)

A solution of 1-11 (0.72 g, 1.57 mmoles) in EtOAc (20 ml) was cooled to −78° C. and HCl gas was bubbled through. This solution for 1-2 minutes and the reaction mixture was then stirred at 0° C. After a few minutes a white solid had precipitated and this mixture was stirred for 0.5 hours. The solvent was then removed and the residue was triturated with Et2O to give pure 1-13.

$^1$H NMR (300 MHz, CD$_3$OD) δ1.23 (3H, t), 1.45 (2H, m), 1.66 (2H, m), 1.72 (2H, m), 2.07 (2H, m), 2.65 (2H, t), 2.94 (2H, m), 3.47 (2H, bd), 3.68 (4H, m), 4.12 (2H, q), 4.57 (2H, s), 7.67 (1H, d), 8.03 (1H, dd), 8.14 (1H, d).

room temperature and the resulting mixture was stirred for 45 minutes. The solvent was then removed and the residue was slurried in DMF (20 ml) and this was treated at room temperature with chloromethyl pivalate (1.8 mmoles). The resulting mixture was stirred at room temperature for 24 hours.

The reaction mixture was then diluted with EtOAc and washed with H$_2$O, 10% KHSO$_4$, saturated with NaHCO$_3$ solvent and brine. The organic phase was dried (MgSO$_4$), and the solvent removed to provide 1-15 as a white solid.

$^1$H NMR (300 MHz, CDCl$_3$) δ1.11-1.25 (13H, m), 1.46 (9H, s), 1.63 (2H, q), 1.77 (2H, bd), 2.62-2.76 (4H, m), 3.72 (9H, m), 4.09 (2H, bd), 4.42 (2H, s), 5.80 (2H, s), 6.89 (1H, bt), 7.53 (1H, d), 8.09 (1H, d), 8.14(1H, s).

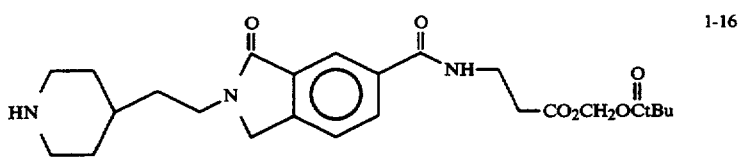

1-16

1-H-Isoindole-5-carboxamide,
2,3-dihydro-N-[2-(t-butylcarbonyloxymethylcarboxy)ethyl]-2-[2-(4-piperidinyl)ethyl]-3-oxo (1-16)

A solution of 1-15 (15 mg) in EtOAc (5 ml) was cooled to −78° C. and treated with HCl gas for 10 minutes and the resulting solution was stirred at −10° C. for 1.0 hour. The solvent was then removed to provide pure 1-16 as a white solid.

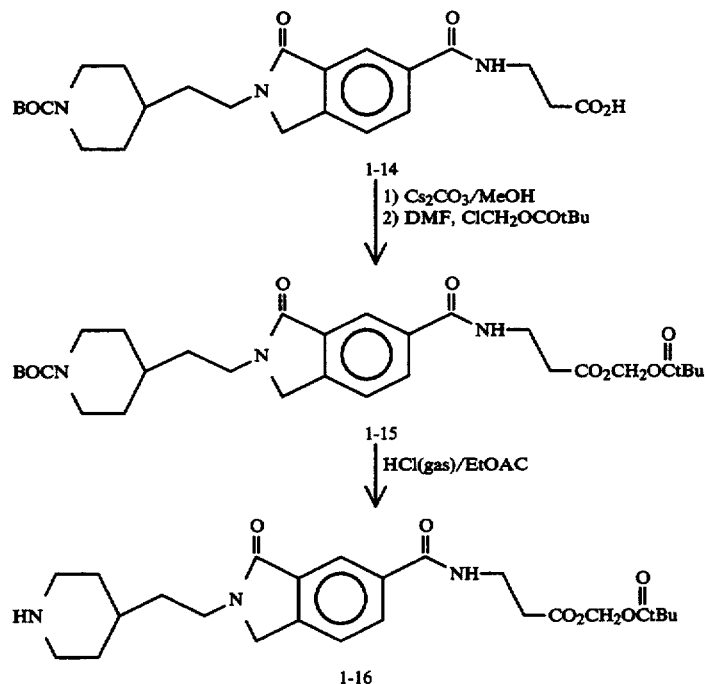

1H-Isoindole-5-carboxamide,
2,3-dihydro-N-[2-(t-butylcarbonyloxymethylcarboxy)ethyl]-2-[2-(4-N-t-butyloxycarbonylpiperidinyl)ethyl]-3-oxo (1-15)

A slurry of 1-16 (0.80 g, 1.8 mmoles) in MeOH (20 ml) was treated with Cs$_2$CO$_3$ (0.24 g, 0.90 mmoles) at $^1$H NMR (300 MHz, CD$_3$OD) δ1.06 (9H, s), 1.92 (1H, m), 1.70 (2H, m), 2.08 (2H, bd), 3.73 (2H, t), 2.95 (2H, dt), 3.38 (2H, bd), 3.70 (6H, m), 4.58 (2H, s), 5.86 (2H, s), 7.67 (1H, d), 8.06 (1H, d), 8.17 (1H, s).

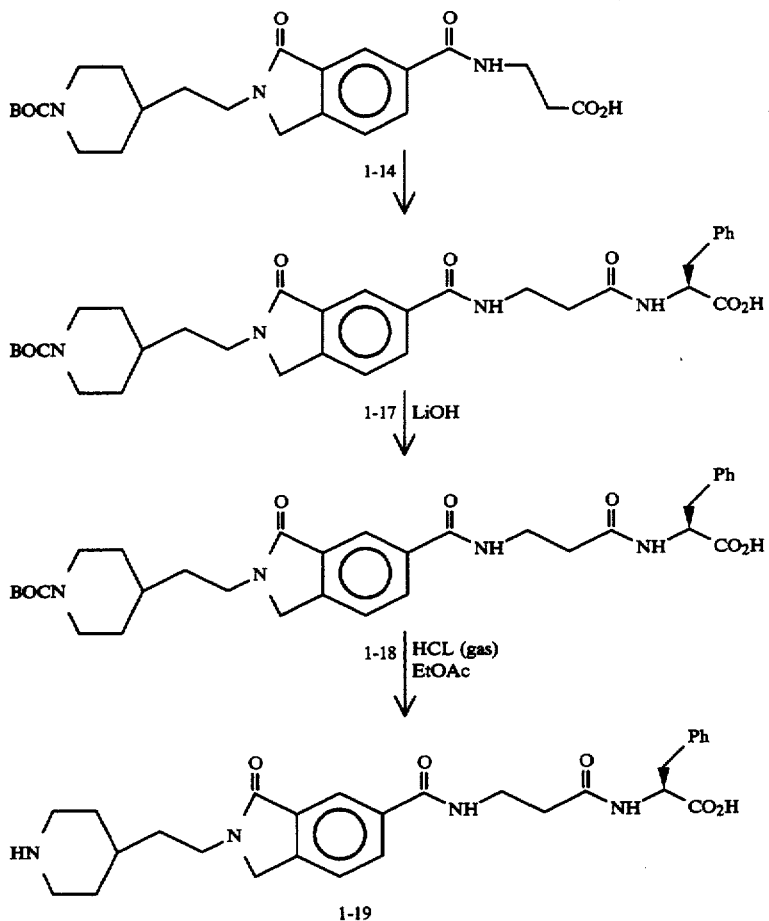

1-H-Isoindole-5-carboxamide,

2,3-dihydro-N-[L-Phe(OEt)-2(carboxamido)ethyl]-2-[2-(4-N-t-butyloxycarbonylpiperidinyl)ethyl]-3oxo(1-17)

1-14 (0.35 g, 0.76 mmoles) was treated with L-phenylalanine ethyl ester (2.0 mmoles), N-methylmorpholine (2.0 mmoles) and BOP (0.886 g, 2.0 mmoles), in CH$_3$CN (5 ml) at room temp for 24 hrs. as described for 6-3. Flash chromatography on silica gel eluting with EtOAc (9)/MeOH (1) gave pure 1–17 as a white solid. R$_f$0.3 (silica gel, CHCl$_3$(2)/acetone (1).

$^1$H NMR (300 MHz, CDCl$_3$) δ1.28 (3H, t), 1.47 (9H,S), 1.79 (2H, bd), 2.54 (2H, t), 2.72 (2H, m), 3.15 (2H, m) 3.75 (5H, m), 4.20 (4H, m), 4.43 (2H, S), 2.90 (1H, q), 7.12 2H, m), 7.25 (5H, m), 7.54 (1H, d), 8.08 d), (1H, d), 8.19 (1H, S).

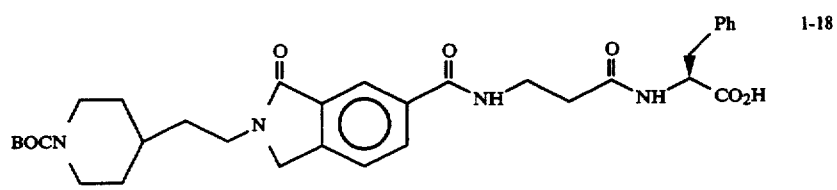

1-H-Isoindole-5-carboxamide, 2,3-dihydro-N[L-Phe-2-(carboxamido)-ethyl]-2-[2-(4-N-t-butyloxycarbonylpiperidinyl)ethyl]-3-oxo(1-18)

1–17 (0.46 g, 0.72 mmoles) was treated with LiOH·H$_2$O (0.152 g, 3.6 mmoles) as described for 1–12 to give 1–18 as a white solid.

$^1$H NMR (300 MHz, CD$_3$OD) δ1.13 (2H, m), 1.43 (9H, s), 1.66 (2H, q), 1.80 (2H, bd), 2.50 (2H, t), 2.70 (2N, M), 2.93 (1H, m), 3.20 (1H, dd), 3.58 (2H, q), 3.70 (2H, t), 4.04 (2H, m), 4.56 (2H, S), 4.68 (1H, m), 7.20 (5H, m), 7.56 (1H, d), 8.02 (1H, d), 8.15 (1H, s).

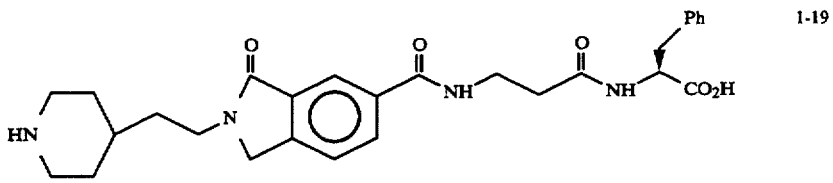

1-H-Isoindole-5-carboxamide, 2,3-dihydro-N[L-Phe-2-(carboxamido)-ethyl]-2-[2-(4-piperidinyl)ethyl]-3-oxo (1-19)

1—18 (0.35 g, 0.37 mmoles) was treated with HCl gas as described for 1–13 to give pure 1–19 as a white solid.

$^1$H NMR (300 MHz, D$_2$O) δ1.35 (2H, m), 1.62 (2H, m), 1.93 (2H, m), 2.43 (2H, m), 2.79 (3H,m), 3.07 (1H, m), 3.28 (2H, m), 3.45(2H, m), 4.50 (2H, S), 6.80 (1H, m), 6.92 (2H, m), 7.00 (2H, m), 7.55 (1H, d), 7.77 (2H, bs).

1H NMR (300 MHz, CDCl$_3$) δ1.16 (2H, m), 1.45 (9H,s), 1.42 (2H, q), 1.65 (2H, bd), 2.03 (2H, m), 2.66 (5H, m), 3.51 (1H, m), 3.67 (2H, m), 3.80 (2H, m), 4.09 (2H, m), 4.20 (2H, q), 4.40 (2H, s), 4.50 (1H, m), 7.41 (1H, m), 7.50 (1H, d), 8.03 (1H, d), 8.19 (1H, s).

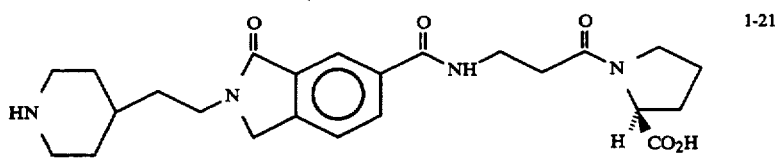

1-H-Isoindole-5-carboxamide, 2,3-dihydro-N-[L-Pro-2-(carboxamido)ethyl]-2-[2-(4-piperidinyl)ethyl]-3-oxo(1-21)

1—20 (0.2 g, 0.34 moles) was treated with LiOH·H$_2$O (0.071 g, 1.7 mmoles) as described for 1–12 to give the desired acid.

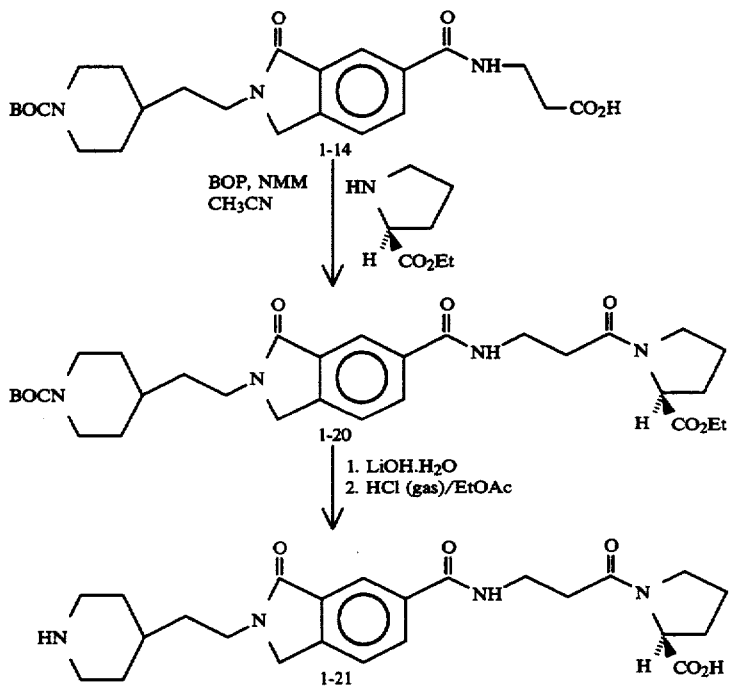

1-H-Isoindole-5-carboxamide, 2,3-dihydro-N-[L-Pro(OEt)-2-(carboxamido)ethyl]-2-[2-(4-N-t-butyloxycarbonylpiperidinyl)ethyl]-3-oxo (1-20)

1—14 (0.35 g, 0.76 mmoles) was treated with L-Proline ethyl ester (0.288 g, 2.0 mmoles), N-methylmorpholine (2.0 mmoles) and BOP (0.886 g, 2.0 mmoles) in CH$_3$CN (5 ml) as described for 1–17 to give an oily residue. This was purified by flash chromatography on silica gel eluting with acetone (1)/CHCl$_3$(1) to give pure 1–20.

$^1$H NMR (300 MHz, CD$_3$OD) δ1.15 (2H, m), 1.44 (9H, s), 1.67 (2H, q), 2.80 (2H, bd), 2.25 (1H, m) 2.73 (2H, m), 3.68 (4H, m), 4.06 (2H, m), 4.55 (2H, s), 7.66 (1H, d), 8.05 (1H, d), 8.17 (1H, s).

This acid (0.15 g) was dissolved is EtOAc (10 ml) and treated with HCl gas as described for 1–13 to give pure 1–21 as a white solid.

1H NMR (300 MHz, D$_2$O) δ1.48 (2H, m), 1.67 (1H, m), 1.76 (2H, m), 2.06 (4H, m), 2.32 (1H, m), 2.62 (1H, m), 2.84 (2H, t), 2.96 (2H, t), 3.43 (2H, d), 3.70 (6H, m), 4.47 (1H, m), 4.66 (2H, s), 7.72 (1H, d), 8.00 (1H, d), 8.09 (1H, s).

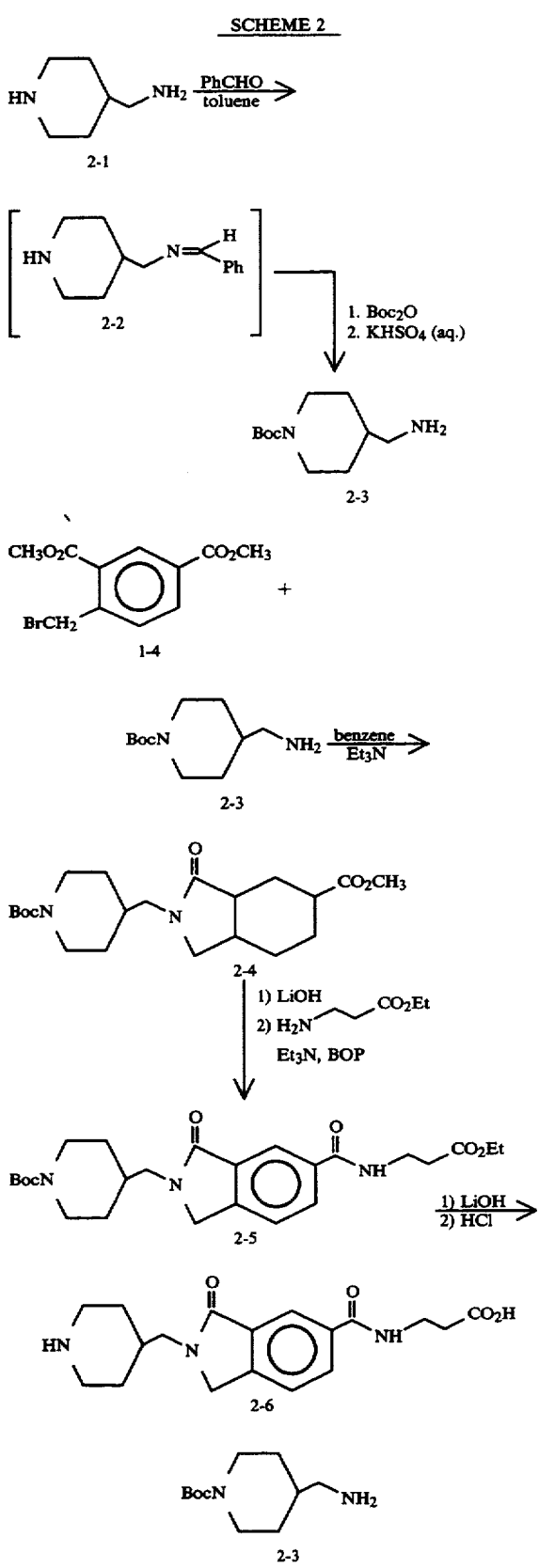

4-(N-t-Butyloxycarbonylpiperidinyl)methylamine (2-3)

A solution of 4-(piperidinyl)methylamine (2-1) (22.8 g, 0.2 mmoles) in toluene (250 ml) was treated with benzaldehyde (21.2 g, 0.2 mmoles) at room temperature and the resulting mixture was heated at reflux for 3 hours with the aid of a Dean-Stark trap for water removal. The cooled reaction mixture containing the desired Schiff's base 2—2 was treated portionwise with di-t-butyl dicarbonate (47.96 g, 0.22 moles) and the resulting solution was stirred at room temperature for 16 hours. The solvent was then removed and the residue was cooled to 0°-5° C. and treated with 1N KHSO$_4$ (220 ml) with stirring for 3 hours. The resulting reaction mixture was extracted with ether (3×200 ml) and then made basic with 1N KOH solution and extracted with CHCl$_3$ (4×75 ml). The combined organic extract was washed with brine, dried (Na$_2$SO$_4$) filtered through celite, and the solvent removed to provide pure 2-3 as a clear oil.

$^1$H NMR (300 MHz, CDCl$_3$) δ1.13 (2H, m), 1.45 (9H, s), 1.60 (1H, m), 1.74 (2H, d), 2.68 (4H, m), 4.15 (2H, bd).

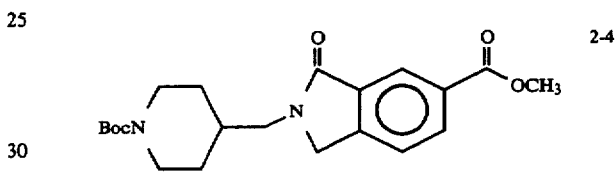

Methyl-1H-Isoindole-4-carboxylate, 2,3-dihydro-N-[(4-N-t-butyloxycarbonylpiperidinyl)-methyl]-3-oxo (2-4)

A solution of 1-4 (3.01 g, 10.5 mmoles) in benzene (20 ml) was treated at room temperature with 2-3 (2.30 g, 10.7 mmoles) and Et$_3$N (10.8 mmoles) and the resulting solution was heated at reflux for 2 hours. The solvent was removed and the residue was taken up in EtOAc (200 ml) and extracted with 10% KHSO$_4$ solution (5×50 ml), brine and dried (MgSO$_4$). Solvent removal gave a residue that was purified by flash chromatography on silica gel eluting with hexane (1)/EtOAc (1) to give pure 2-4. R$_f$0.25.

$^1$H NMR (300 MHz, CDCl$_3$) δ1.29 (2H, m), 1.45 (9H, s), 1.67 (4H, m), 1.95 (1H, m), 2.70 (2H, t), 3.52 (2H, b), 3.97 (3H, s), 4.13 (2H, b), 4.95 (2H, s), 7.52 (1H, d), 8.23 (1H, d), 8.50 (1H, s).

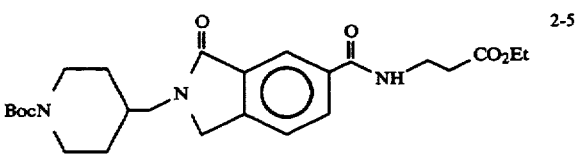

1-H-Isoindole-5-carboxamide, 2,3-dihydro-N-[2-(carboethoxyethyl]-2[(4-N-t-butyloxycarbonylpiperidinyl)methyl]-3-oxo (2-5)

A solution of 2-4 (1.92 g, 5.58 mmoles) in 150 ml of THF(1)/MeOH(1)/H$_2$O(1) was treated with LiOH·H$_2$O (1.20 g, 28.6 mmoles) at room temperature and the resulting solution was stirred for 1.0 hr. The solvent was then removed and the residue was taken up in H$_2$O (100 ml) acidified to pH 2 with 10% KHSO$_4$ solution. The desired acid precipitated from solution and was collected.

¹H NMR (300 MHz, CD₃OD) δ1.13 (2H, m), 1.40 (9H, s), 1.50–1.65 (3H, m), 2.70 (2H, b), 3.45 (2H, d), 3.98 (2H, d), 4.45 (2H, s), 7.60 (1H, d), 8.10 (1H, d), 8.21 (1H, s).

This acid (1.62 g, 4.91 mmoles) was dissolved in CH₃CN (25 ml) and treated at 0° successively with Et₃N (34.4 mmoles), β-alanine ethyl ester (5.0 moles), and BOP (3.27 g, 7.38 moles). The reaction mixture was then stirred at room temperature for 16 hrs. The solvent was removed and the residue purified by flash chromatography in silica gel eluting with EtOAc (7)/hexane (1) to provide 2-5 as a white solid.

¹H NMR (300 MHz, CDCl₃) δ 1.27 (6H, m), 1.42 (9H, s), 1.67 (5H, m), 1.95 (1H, m), 2.66 (4H, m), 3.50 (2H, b), 3.74 (2H, g), 4.16 (4H, m), 4.45 (2H, s), 7.00 (1H, t), 7.53 (1H, d), 8.11 (2H, m).

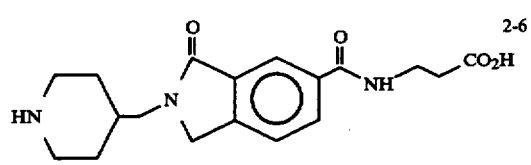

1-H-Isoindole-5-carboxamide, 2,3-dihydro-N-(2-carboxyethyl)-2-[(4-piperidinyl)methyl]-3-oxo (2-6)

A solution of 2-5 (0.86 g, 2.0 mmoles) in 60 ml of THF(1)/MeOH(1)/H₂O(1) was treated with LiOH·H₂O (0.45 g, 10.7 mmoles) at room temperature and the resulting solution was stirred at room temperature for 1.0 hr. The solvent was removed and the residue was dissolved in H₂O (25 ml), acidified to pH 2–3 with 10% KHSO₄ solution and extracted with EtOAc (4×25 ml). The combined organic extracts were washed with brine, dried (Na₂SO₄) and the solvent removed to give the desired acid as a white solid.

1H NMR (300 MHz, CD₃OD) δ1.16 (2H, m), 1.39 (9H, s), 1.45 (1H, m), 1.80 (2H, bd), 1.93 (2H, d), 2.58 (2H, t), 2.70 (2H, b), 3.45 (2H, d), 3.57 (2H, t), 4.00 (2H, m), 7.59 (1H, d), 8.00 (1H, d), 8.09 (1H, s).

This acid (0.80 g, 1.89 moles) was treated with HCl gas in EtOAc solution as described for 2-3 to provide pure 2-6 as a white solid.

¹H NMR (300 MHz, CD₃OD) δ1.43 (2H, m), 1.85 (2H, m), 2.10 (1H, m), 2.56 (2H, t), 2.90 (2H, t), 3.34 (2H, bd), 3.54 (4H, m), 4.52 (2H, s), 7.61 (1H, d), 8.00 (1H, d), 8.10 (1H, s).

2-5 can also be converted to 2-7 as shown below:

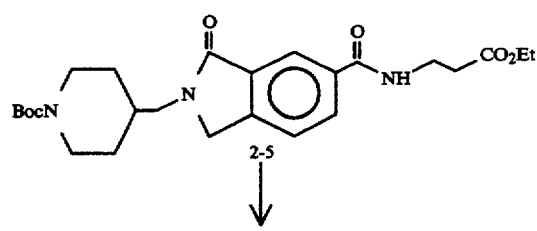

1-H-Isoindole-5-carboxamide,2,3-dihydro-N-[(2-carboethoxy)ethyl]-2-[2-(4-piperidinyl)methyl]-3-oxo(2-7)

Treatment of 2-5 (0.90 g, 2.09 mmoles) in EtOAc with HCl gas as described for 1-12 gave 2-7 as an white, solid.

¹H NMR (300 MHz, CD₃OD) δ1.09 (3H, t), 1.45 (2H, m), 1.86 (2H, bd), 2.13 (2H, m), 2.60 (2H, t), 2.90 (2H, t), 3.32 (2H, bd), 3.56 (4H, m), 4.08 (2H, q), 4.56 (2H, s), 7.62 (1H, d), 8.00 (1H, d), 8.09 (1H, s).

SCHEME 3

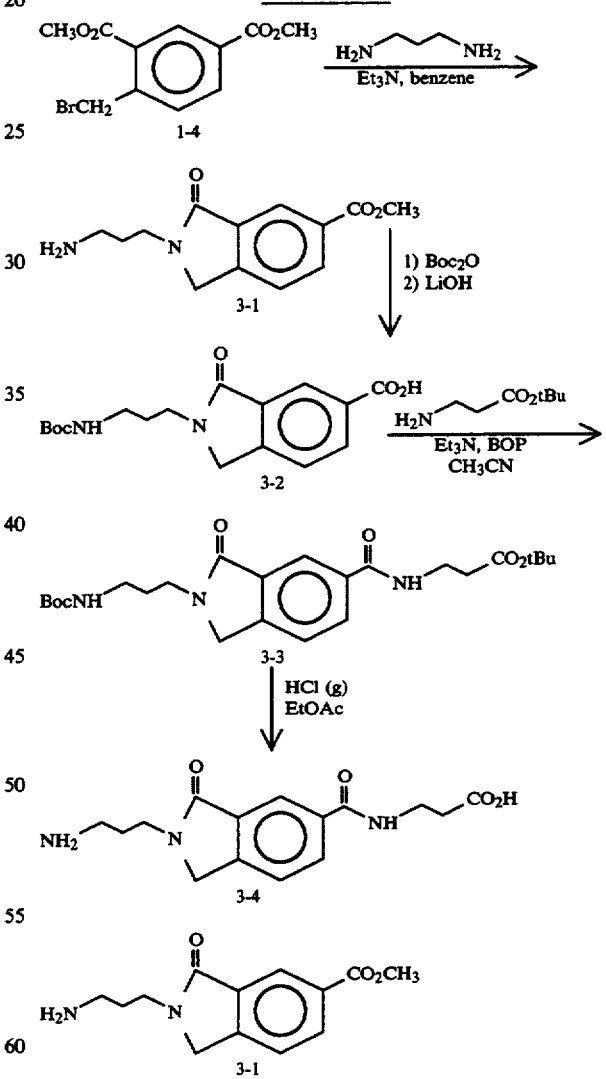

Methyl- 1H-Isoindole-5-carboxylate, 2,3-dihydro-N-[3-aminopropyl]-3-oxo (3-1)

A solution of 1-4 (2.58 g, 8.99 mmoles in benzene (10 ml) was treated with Et₃N (12.9 mmoles) and 1,3-diaminopropane (13.0 mmoles) at room temperature and the resulting mixture was heated at reflux for 2 hrs. The reaction mixture was cooled and the solvent removed to give 3-1.

¹H NMR (300 MHz, CD₃OD) δ1.53 (9H, s), 1.79 (2H, m), 3.02 (2H, m), 3.58 (2H, m), 3.84 (3H, s), 4.48 (2H, s), 7.58 (1H, d), 8.10 (1H, d), 8.20 (1H, s).

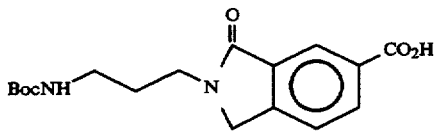

1-H-Isoindole-5-carboxylic acid, 2,3-dihydro-N-[3-(N-t-butyloxycarbonylamino)propyl]-3-oxo (3-2)

3-1 (2.22 g, 8.99 mmoles) was suspended in 100 ml of THF(1)/H₂O(1) and treated with Et₃N (9.3 mmoles) and di-t-butyl dicarbonate (4.0 g, 18.3 mmoles) and the resulting mixture was stirred vigorously for 5 hrs. The solvent was removed and the residue was purified by flash chromatography to give the desired protected ester.

¹H NMR (300 MHz, CD₃OD) δ1.53 (9H, s), 1.80 (2H, m), 3.03 (2H, m), 3.58 (2H, m), 3.86 (3H, s), 4.48 (2H, s), 7.55 (1H, d), 8.10 (1H, d), 8.20 (1H, s).

This ester (0.67 g, 1.93 mmoles) was treated with LiOH·H₂O (0.41 g, 9.76 mmoles) in 60 ml of THF(1)/MeOH(1)/H₂O(1) at room temperature for 1 hr. Solvent removal gave a residue that was dissolved in 25 ml H₂O, acidified to pH 2-3 with 10% KHSO₄ solution and extracted with EtOAc (4×25 ml). The organic extract was washed with brine, dried (MgSO₄) and the solvent removed to give 3-2 as a white solid.

¹H NMR (300 MHz, CD₃OD) δ1.35 (9H, s), 1.80 (2H, m), 3.04 (2H, t), 3.62 (2H, t), 4.55 (2H, s), 7.62 (1H, d), 8.20 (1H, d), 8.32 (1H, s).

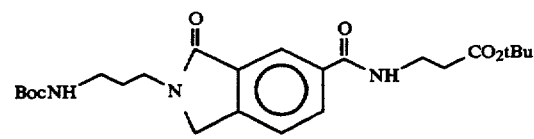

1-H-Isoindole-5-carboxamide, 2,3-dihydro-N-[2-(t-butyloxycarbonyl)-ethyl]-2-[3-(N-t-butyloxycarbonylamino)propyl]-3-oxo (3—3)

A solution of 3-2 (0.65 g, 1.94 mmoles) in 10 ml CH₃CN was cooled to 0°-10° and treated with Et₃N (13.6 mmoles) and BOP (1.30 g, 2.93 mmoles) and the resulting solution was stirred at room temperature for 16 hrs. The solvent was then removed and the residue was taken up in EtOAc (100 ml) extracted with H₂O (4×25 ml), 10% KHSO₄ solution and dried (MgSO₄). Solvent removal give a residue that was purified by flash chromatography on silica gel eluting with CHCl₃(95)/MeOH(5) to give pure 3—3 as a white solid. Rƒ0.3 (silica gel, CHCl₃(95)/MeOH(5)).

¹H NMR (300 MHz, CDCl₃), δ1.46 (9H, s), 1.53 (9H, s), 1.90 (2H, m), 2.62 (2H, t), 3.60 (2H, m), 3.76 (4H, m), 4.50 (2H, s), 7.00 (1H, 6t, 7.62 (1h, d). 8.17 (1H, d), 8.20 (1H, s).

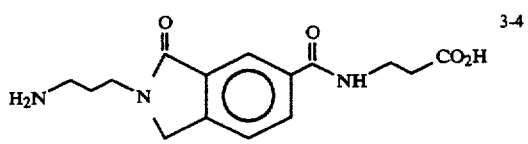

1-H-Isoindole-5-carboxamide, 2,3-dihydro-N-(2-carboxyethyl)-2-[3-aminopropyl]-3-oxo (3-4)

3—3 (0.77 g, 1.67 mmoles) was suspended in EtOAc (25 ml) and after cooling to −70°, HCl gas was bubbled into the mixture for 5 minutes at which time the reaction mixture was homogeneous. The reaction mixture was then stirred at 0°-5° for 30 minutes. The solvent was removed and the residue was dried at high vacuum to provide pure 3-4 as a white solid.

¹H NMR (300 MHz, CD₃OD) δ 2.00 (2H, m), 2.60 (2H, t) 2.92 (2H, t), 3.59 (2H, m), 3.70 (2H, t), 4.28 (2H, s), 7.63 (1H, d), 8.02 (1H, d), 8.12 (1H, s).

SCHEME 4

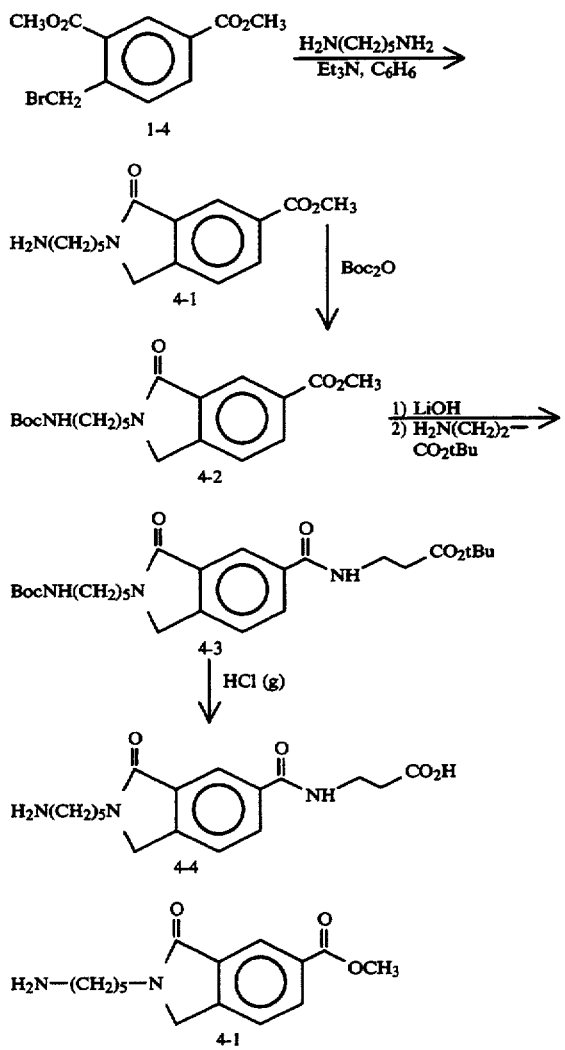

Methyl- 1H-Isoindole-5-carboxylate, 2,3-dihydro-N-[5-aminopentyl]-3-oxo (4-1)

A solution of 1-4 (2.56 g, 8.92 mmoles) in benzene (15 ml) was treated with Et₃N (11.5 mmoles) and 1,5- diaminopentane (11.9 mmoles) and the resulting reaction mixture was heated at reflux for 3 hrs. The solvent was then removed and the residue was purified by flash chromatography on silica gel eluting with 25% MeOH in CHCl₃ (MHz) to provide pure 4-1.

¹H NMR (300 MHz, CDCl₃) δ1.77 (6H, m), 2.45 (2H, bs), 2.71 (2H, t), 3.63 (2H, t), 4.44 (2H, s), 7.52 (1H, d), 8.22 (1H, d), 8.49 (1H, s).

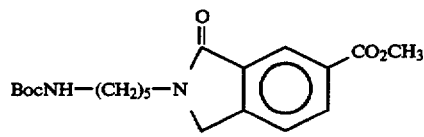

4-2

Methyl-1H-Isoindole-5-carboxylate, 2,3-dihydro-N-[5-(N-t-butyloxycarbonylamino)pentyl]-3-oxo (4-2)

A solution of 4-1(0.64 g, 2.32 mmoles) in CH₂Cl₁₂ (10 ml) was treated at room temperature with Et₃N (2.29 mmoles) and Boc₂O (0.74 g, 3.39 mmoles) for 48 hrs. The solvent was then removed and the residue was purified by flash chromatography on silica gel eluting with hexane(7)/acetone(3) to give pure 4-2.

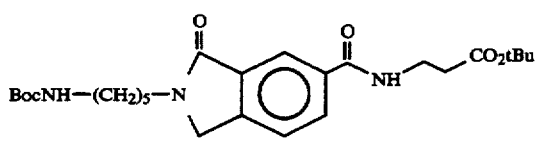

4-3

1-H-Isoindole-5-carboxamide, 2,3-dihydro-N-[2-(2-t-butyloxycarbonyl)ethyl]-2-[5-N-t-butyloxycarbonylamino)pentyl]-3-oxo (4-3)

A solution of 4-2 (0.71 g, 1.89 mmoles) in THF(1)/MeOH(1)/H₂O(1) (60 ml) was treated with LiOH·H₂O (0.42 g, 10.0 mmoles) at room temperature for 0.5 hr. The solvent was then removed and the residue was dissolved in H₂O (50 ml), acidified to pH 2–3 with 10% KHSO₄ solution and extracted with EtOAc. The organic phase was washed with brine, dried (MgSO₄) and the solvent removed to give the desired acid.

¹H NMR (300 MHz, CD₃OD) δ1.30 (9H, s), 1.45 (3H, m), 1.63 (3H, m), 2.92 (2H, t), 3.55 (2H, t), 4.47 (2H, s), 7.58 (1H, d), 8.16 (1H, d), 8.03 (1H, s).

This acid (0.75 g, 2.07 mmoles) was dissolved in CH₃CN (15 ml) and was treated at room temperature with p-alanine t-butyl ester (0.39 g, 2.54 mmoles), BOP (1.4 g, 3.16 mmoles), Et₃N (6.1 mmoles) and the resulting solution was stirred at room temperature for 20 hrs. The solvent was then removed and the residue was dissolved in EtOAc and extracted with H₂O, 10% KHSO₄ solution and brine. The organic phase was dried (MgSO₄) and was solvent was removed to give a residue that was purified by flash chromatography on silica gel eluting with EtOAc(7)/hexane(3) to give pure 4-3.

¹H NMR (300 MHz, CD₃OD) δ1.39 (9H, s), 1.45 (2H, m), 1.65 (2H, m), 2.50 (2H, t), 2.96 (2H, q), 3.53 (4H, q), 4.47 (2H, s), 7.58 (1H, d), 7.96 (1H, d), 8.08 (1H, s).

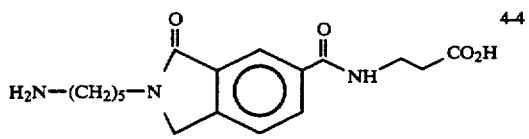

4-4

1-H-Isoindole-5-carboxamide, 2,3-dihydro-N-(2-carboxyethyl)-2-[5-aminopentyl]-3-oxo (4—4)

A solution of 4-3 (0.71 g, 1.45 mmoles) in EtOAc (20 ml) was cooled to −78° and treated with HCl gas for 10 minutes. The resulting solution was stirred in at 0° for 0.5 hr. The solvent was removed to provide 4—4 as white solid.

¹H NMR (300 MHz, D₂O) δ1.29 (2H, m), 1.63 (4H,m), 2.62 (2H,t, 2.87 (2H, t), 3.52 (4H, m), 4.40 (2H, s), 7.51 (1H, d), 7.80 (2H, m).

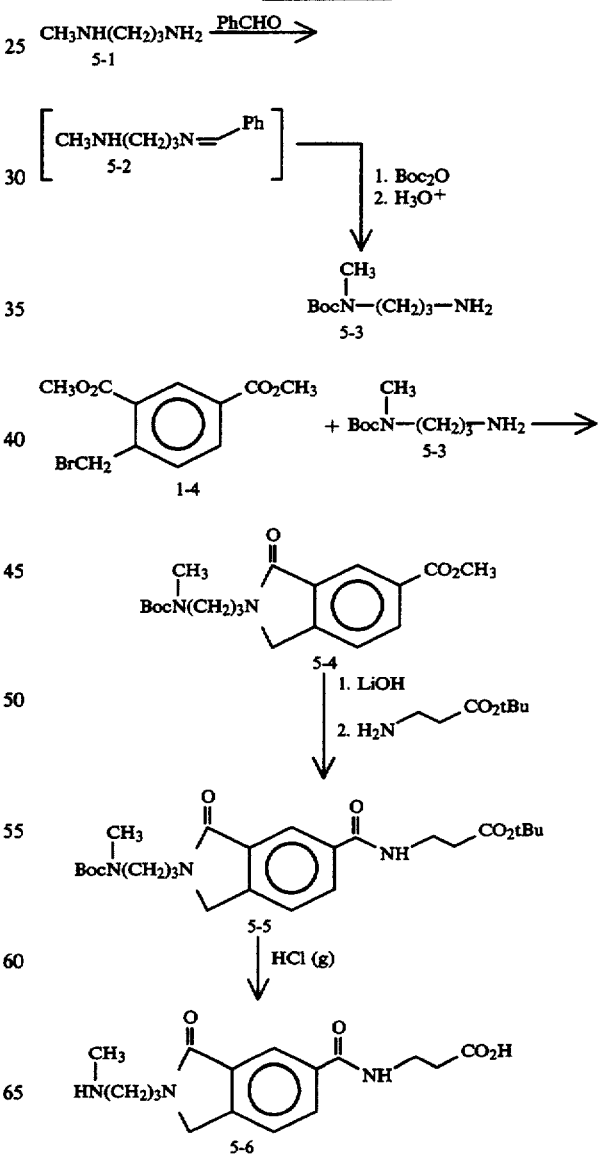

SCHEME 5

SCHEME 5

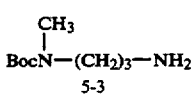
5-3

N-t-Butyloxycarbonyl-N-methyl-1,3-diaminopropane (5-3)

A solution of N-methyl-1,3-diaminopropane (2.05 g, 23.2 mmoles) in toluene (30 ml) was treated with benzaldehyde (2.41 g, 22.7 mmoles) and the resulting mixture was heated at reflux with use of a Dean-Stark trap. After 2 hrs. the reaction mixture was cooled and treated with Boc$_2$O (5.57 g, 25.5 mmoles) portionwise and the resulting solution was stirred for 48 hrs.

The solvent was then removed and the residue was cooled to 0°-5° and acidified to pH 2-3 with 10% KHSO$_4$ solution (25 ml) and the resulting slurry was stirred for 3 hrs. This mixture was then extracted with EtOAc and the aqueous phase was adjusted to pH 9 with 1N NaOH and extracted with CHCl$_3$ (5×25 ml). The dried organic phase was concentrated to give 5-3 as an oil.

$^1$H NMR (300 MHz, CDCl$_3$) δ1.47 (9H, s), 1.72 (2H, bt), 2.16 (2H, bs), 2.75 (2H, t), 2.87 (3H, s), 3.34 (2H, bs).

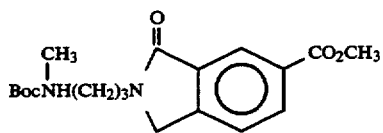
5-4

Methyl-1H-Isoindole-5-carboxylate, 2,3-dihydro-N-[2-(3-N-t-butyloxycarbonyl-N-methylamino)propyl]-3-oxo (5-4)

A solution of 1-4 (2.0 g, 6.97 mmoles) in benzene (10 ml) was treated with 5-3 (1.19 g, 6.32 mmoles) and Et$_3$N (7.17 mmoles) and the resulting solution was heated at reflux for 24 hrs. The cooled reaction mixture was then dissolved in EtOAc (150 ml), washed with 10% KHSO$_4$ solution (4×50 ml), brine (50 ml) and dried (MgSO$_4$). The solvent was removed to give an oil that was purified by flash chromatography on silica gel eluting with EtOAc(7)/hexane(1) to give pure 5-4 as a white solid.

$^1$H NMR (300 MHz, CDCl$_3$) δ1.45 (9H, s), 1.92 (2H, m), 2.90 (3H, s), 3.30 (2H, t), 3.68 (2H, t), 3.97 (3H, s), 4.50 (2H, s), 7.55 (1H, d), 8.26 (1H, d), 8.52 (1H, s).

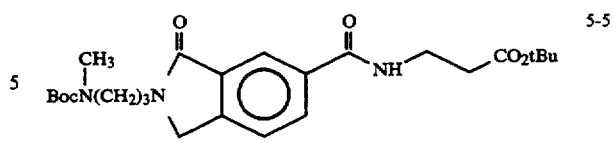
5-5

1-H-Isoindole-5-carboxamide, 2,3-dihydro-N-[2-(t-butyloxycarbonyl)ethyl]-2-[3-(N-t-butyloxycarbonyl-N-methylamino)propyl]-3-oxo (5—5)

A solution of 5-4 (1.28 g, 3.53 mmoles) in THF(1)/MeOH-(1)/H$_2$O(1) (105 ml) was treated with LiOH·H$_2$O (0.76 g, 18.1 mmoles) and the resulting solution was stirred at room temperature for 30 minutes. The solvent was then removed and the residue was taken up in H$_2$O (30 ml), acidified to TpH 2-3 with 10% KHSO$_4$ solution, and extracted with EtOAc. The combined organic extracts were washed with brine, dried (MgSO$_4$) and the solvent removed to provide the desired acid.

$^1$H NMR (300 MHz, CD$_3$OD) δ1.34 (9H, s), 1.86 (2H, m), 2.78 (3H, s), 3.22 (2H, m), 3.55 (2H, t), 4.50 (2H, s), 7.60 (1H, d), 8.17 (1H, d), 8.30 (1H, s).

This acid (1.28 g, 3.59 mmoles) was dissolved in CH$_3$CN (20 ml) and treated successively with β-alanine t-butyl ester hydrochloride (0.65 g, 3.59 mmoles), Et$_3$N (2.51 mmoles), and BOP (2.39 g, 5.40 mmoles) and the resulting cloudy suspension was stirred at room temperature for 20 hrs. The reaction mixture was then concentrated and the residue was taken up in EtOAc (100 ml), extracted with H$_2$O (2×25 ml), 10% KHSO$_4$ solution (4×25 ml), brine and dried (MgSO$_4$). Solvent removal gave a residue that was purified by flash chromatography on silica gel eluting with acetone(3)/hexane(7) to give pure 5—5 as a white solid.

$^1$H NMR (300 MHz, CDCl$_3$) δ1.42 (9H, s), 1.44 (9H, s), 1.93 (2H, m), 2.37 (2H, t), 2.88 (3H, s), 3.30 (2H, t), 3.68 (4H, m), 4.47 (2H, s), 6.98 (1H, bt), 7.55 (1H, d), 8.09 (1H, d), 8.12 (1H, s).

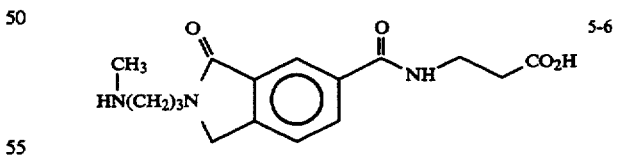
5-6

1-H-Isoindole-5-carboxamide, 2,3-dihydro-N-(2-carboxyethyl)-2-[3-(N-methylamino)propyl]-3-oxo (5-6)

A solution of 5—5 (1.42 g, 2.09 mmoles) in EtOAc (40 ml) was cooled to −78° and treated with HCl gas for 3-5 minutes. The resulting solution was stirred at 0° for 0.5 hr. The solvent was then removed to provide 5-6 as a white solid.

$^1$H NMR (300 MHz, D$_2$O) δ 2.00 (2H, m), 2.62 (5H, m), 3.00 (2H, t), 3.60 (4H, m), 4.29 (2H, s), 7.75 (1H, d), 7.83 (1H, d), 7.88 (1H, s).

SCHEME 6

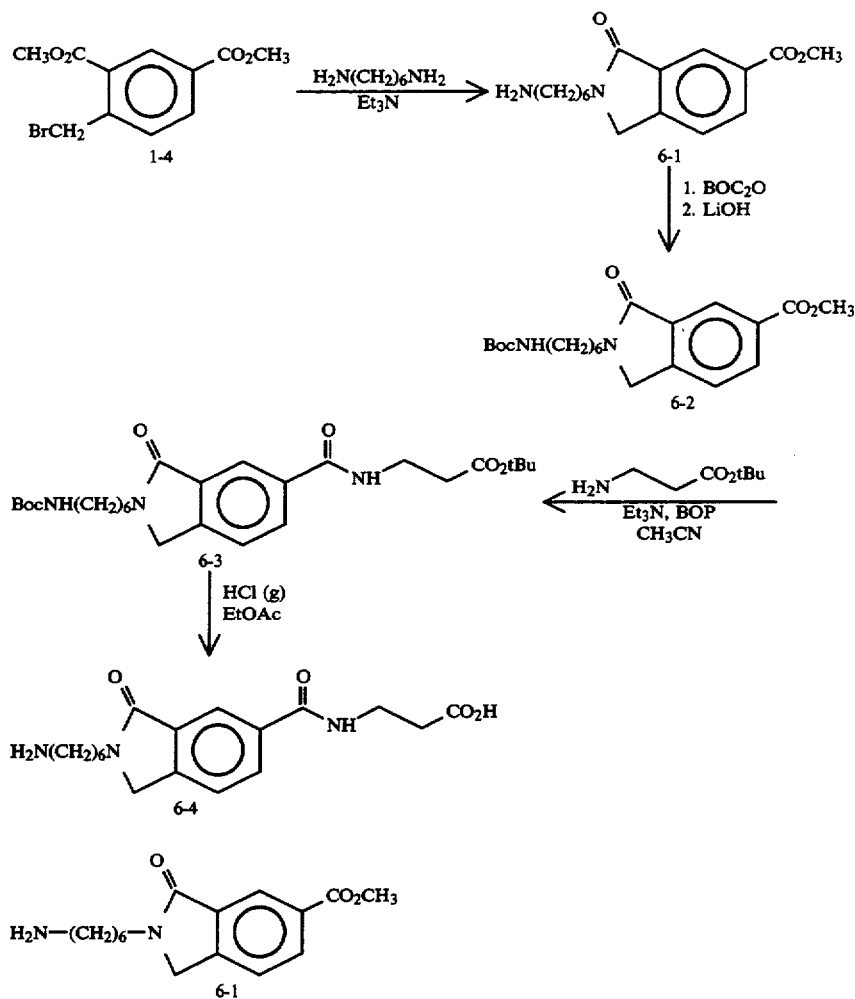

Methyl- 1H-Isoindole-5-carboxylate, 2,3-dihydro-N-[6-aminohexyl]-3-oxo (6-1)

Treatment of 1-4 with 1,6-diaminohexane as described for 1-9 provided 6-1 as a white solid. R$_f$ 0.5 (silica gel, hexane (9)/EtOAc (1)).

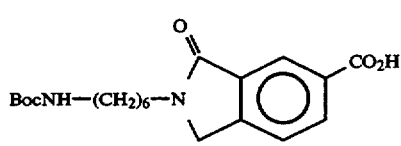

1-H-Isoindole-5-carboxylic acid, 2,3-dihydro-N-[6-N(t-butyloxycarbonylamino)hexyl]-3-oxo (6-2)

Treatment of 6-1 with Boc$_2$O (1 equiv) and triethylamine (2 equivalents) in H$_2$O(1)/THF(1) (100 ml) at room temperature for 48 hours followed by solvent removal gave crude BOC-protected derivative. Hydrolysis of this with LiOH·H$_2$O (4 equiv.) as described for 1-10 gave 6-2 as an oil. $^1$H NMR/(300 MHz, CD$_3$OD) δ1.32 (17H, m), 1.68 (2H, m) 2.95 (2H, t), 4.50 (2H, s), 7.62 (1H, d), 8.19 (1H, d), 8.31 (1H, s).

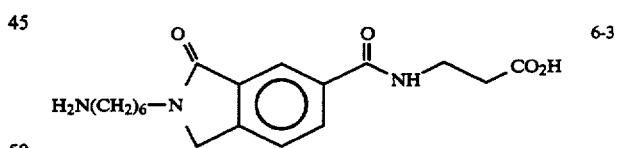

1-H-Isoindole-5-carboxamide, 2,3-dihydro-N-[2-(t-butyloxycarbonyl)ethyl]-2-[6-N-(t-butyloxycarbonylamino)hexyl]-3-oxo (6-3)

Treatment of 6-2 (1.18 g, 3.12 mmoles) with t-butyl β-alanine (0.54 g, 3.51 mmoles) as described for 1-11 gave crude 6-3. This was purified by flash chromatography on silica gel eluting with pet ether (6)/EtOAc (4) to provide 6-3 as an oil. R$_f$ 0.25 (silica gel, pet ether (7)/acetone (3)).

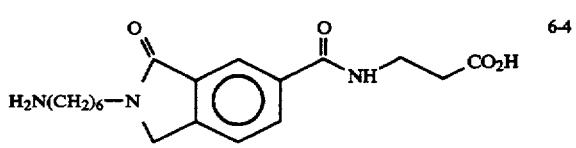

1-H-Isoindole-5-carboxamide, 2,3-dihydro-N-(2-carboxyethyl)-2-[6-aminohexyl]-3-oxo (6-4)

6-3 (0.44 g) was dissolved in EtOAc (25 ml) cooled to −78° and treated with HCl gas for 5 minutes. The reaction mixture was then stirred at 0° for 30 minutes and the solvent was removed. The residue was purified by flash chromatography on silica gel eluting with EtOH(9)/H$_2$O(1)/NH$_4$OH(1) to provide 6-4. as a whim solid.

$^1$H NMR (300 MHz, CD$_3$OD) δ1.42 (4H, m), 1.68 (4H, m), 2.63 (2H, t), 2.88 (2H, t), 3.60 (4H, m), 4.52 (2H, s), 7.60 (1H, d), 7.97 (1H, d), 8.10 (1H, s).

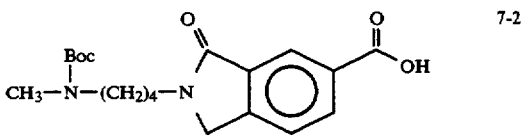

1H-Isoindole-5-carboxylic acid, 2,3-dihydro-N-[4-(N-methyl-N-t-butyloxycarbonylamino)butyl]-3-oxo (7-2)

Treatment of 7-4 with 4-(1.16 g, 2.08 mmoles) with LiOH·H$_2$O (0.65 g, 15.5 mmoles) in THF(1)/CH$_3$OH(1)/H$_2$O(I) (75 ml) as described for 1-10 gave 7-2 as a white solid. $^1$H NMR (300 MHz, CD$_3$OD) δ1.67 (10H, m), 1.80 (2H, m), 1.89 (2H, m), 3.05 (3H, s), 3.50 (2H, t), 3.88 (2H, t), 4.78 (2H, s), 7.90 (1H, d), 8.45 (1H, d), 8.60 (1H, s).

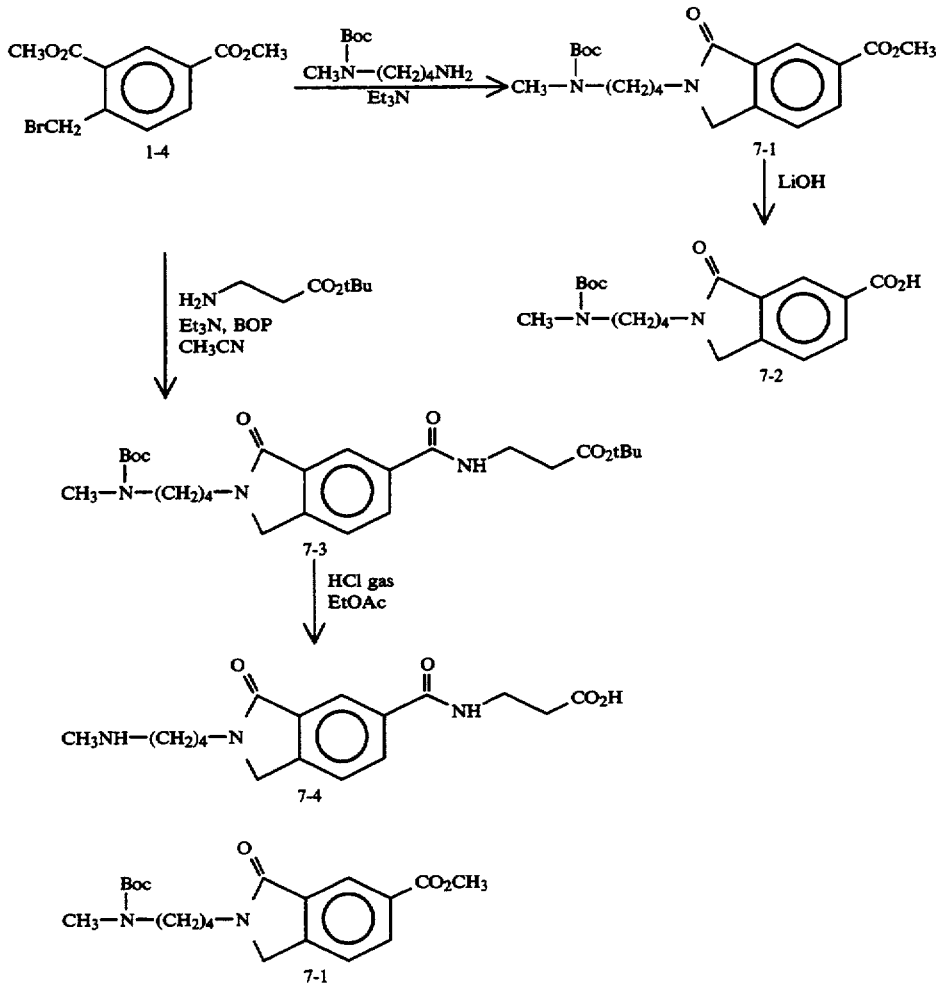

SCHEME 7

Methyl- 1H-Isoindole-5-carboxylate, 2,3-dihydro-N-[4-(N-methyl-N-t-butyloxycarbonylamino)butyl]-3-oxo (7-1)

Treatment of 1-4 with 4-(N-methyl-N-t-butyloxycarbonylamino)butylamine (prepared as described for 5-3) as described for 1-9 provided crude 7-1. This was purified by flash chromatography on silica gel eluting with EtOAc(7)/hexane(3) to give pure 7-1. R$_f$ 0.3 (silica gel, EtOAc(7)/hexane(3). 1H NMR (300 MHz, CDCl$_3$) δ1.45 (9H, s), 1.60 (4H, m), 7.52 (1H, d), 8.23 (1H, d), 8.23 (1H, d), 8.50 (1H, s).

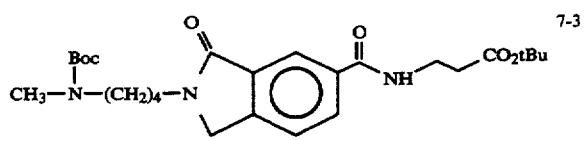

1-H-Isoindole-5-carboxamide, 2,3-dihydro-N-[2-(t-butyloxy-carbonyl)ethyl]-2-[4-(N-t-butyloxycarbonyl-N-methylamino)butyl]-3-oxo (7-3)

Treatment of 7-2 (1.04 g, 2.86 mmoles) with β-alanine t-butyl ester (0.54 g, 2.97 mmoles) as described for 1-11 gave crude 7-3. This was purified by flash chromatography on silica gel eluting with hexane(6)/acetone(4) to give 7-3 as an oil. $R_f$ 0.4 (silica gel, EtOAc(7)/hexane(3).

$^1$H NMR (300 MHz, CHCl$_3$) δ 1.46 (18H, m), 1.60 (4H, m), 2.58 (2H, t), 2.83 (3H, s), 3.28 (2H, t), 3.70 (4H, m), 4.45 (2H, s), 7.52 (1H, d), 8.09 (1H, d), 8.11 (1H, s).

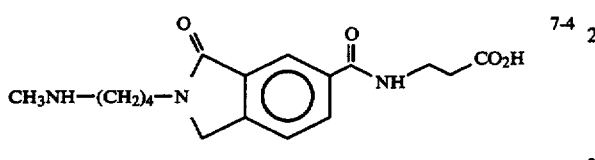

1-H-Isoindole-5-carboxamide, 2,3-dihydro-N-(2-carboxyethyl)-2-[4-(N-methylamino)butyl]-3-oxo (7-4)

Treatment of 7-3 with HCl gas in EtOAc solution as described for 6-4 gave 7-4 as a whim solid.

$^1$H NMR (300 MHz, CD$_3$OD) δ 1.67 (4H, m), 2.58 (5H, m), 2.95 (2H, t), 3.50 (4H, m), 4.50 (2H, s), 7.56 (1H, d), 7.97 (1H, d), 8.08 (1H, s).

SCHEME 8

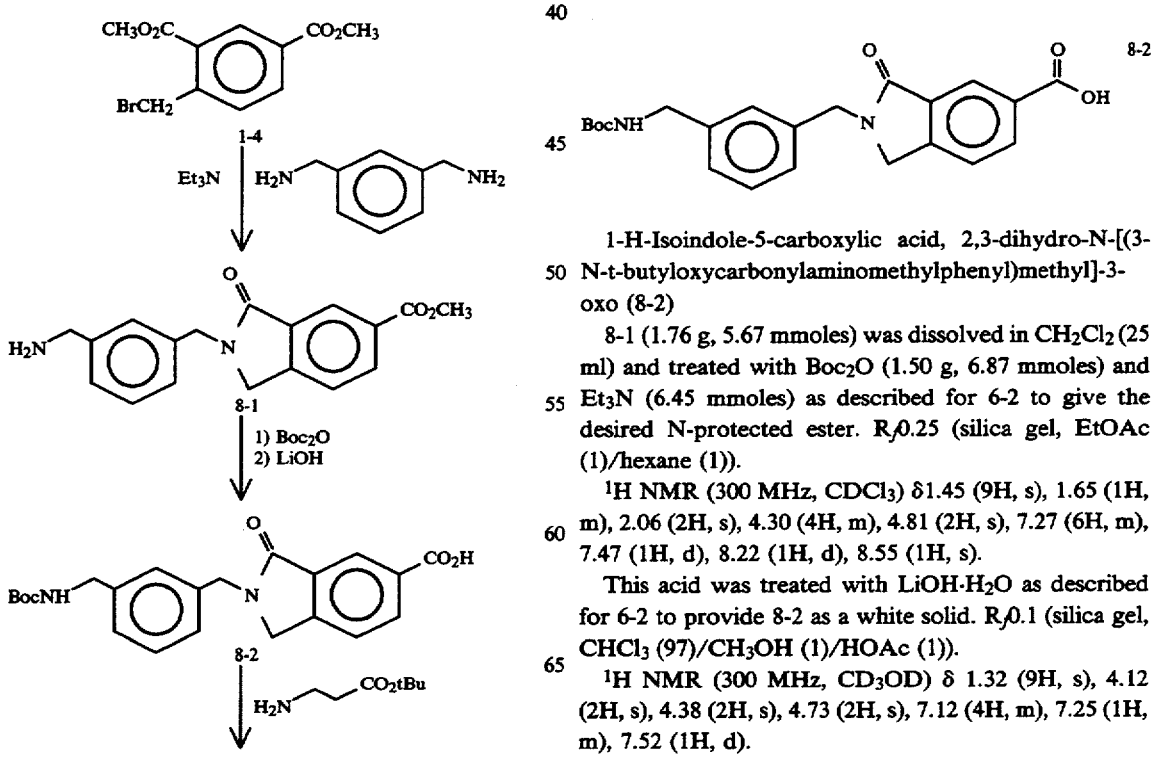

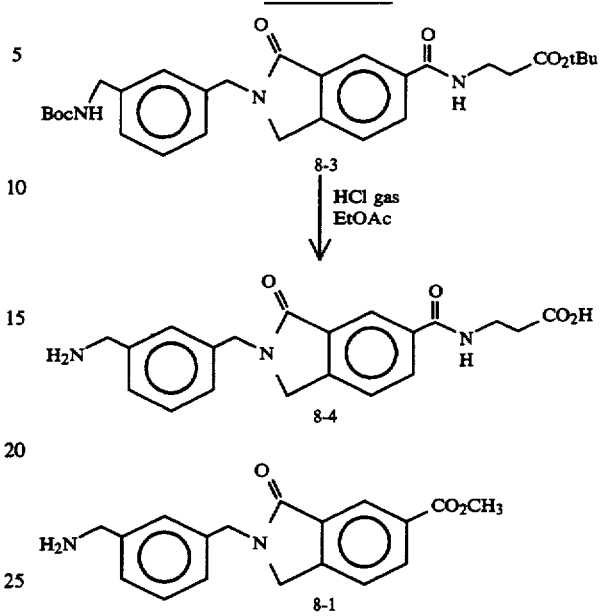

Methyl-1H-Isoindole-5-carboxylate, 2,3-dihydro-N-[(3-aminomethylphenyl)methyl]-3-oxo (8-1)

Treatment of 1-4 (2.15 g, 7.49 mmoles) with m-xylenediamine (9.85 mmoles) as described for 1-9 gave crude 8-1. This was purified by flash chromatography on silica gel eluting with CH$_3$OH (10/CHCl$_3$ (NH$_4$OH) (90) to give pure 8-1 as a white solid. $R_f$ 0.7 silica gel, CH$_3$OH (10)/CHCl$_3$ (NH$_4$OH) (90).

1-H-Isoindole-5-carboxylic acid, 2,3-dihydro-N-[(3-N-t-butyloxycarbonylaminomethylphenyl)methyl]-3-oxo (8-2)

8-1 (1.76 g, 5.67 mmoles) was dissolved in CH$_2$Cl$_2$ (25 ml) and treated with Boc$_2$O (1.50 g, 6.87 mmoles) and Et$_3$N (6.45 mmoles) as described for 6-2 to give the desired N-protected ester. $R_f$ 0.25 (silica gel, EtOAc (1)/hexane (1)).

$^1$H NMR (300 MHz, CDCl$_3$) δ1.45 (9H, s), 1.65 (1H, m), 2.06 (2H, s), 4.30 (4H, m), 4.81 (2H, s), 7.27 (6H, m), 7.47 (1H, d), 8.22 (1H, d), 8.55 (1H, s).

This acid was treated with LiOH·H$_2$O as described for 6-2 to provide 8-2 as a white solid. $R_f$ 0.1 (silica gel, CHCl$_3$ (97)/CH$_3$OH (1)/HOAc (1)).

$^1$H NMR (300 MHz, CD$_3$OD) δ 1.32 (9H, s), 4.12 (2H, s), 4.38 (2H, s), 4.73 (2H, s), 7.12 (4H, m), 7.25 (1H, m), 7.52 (1H, d).

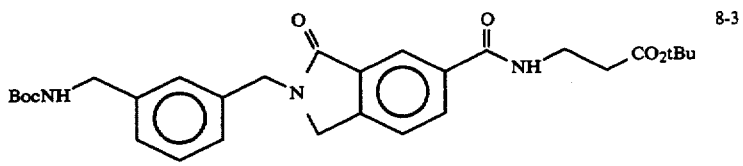

1-H-Isoindole-5-carboxamide, 2,3-dihydro-N-[2-(t-butyloxycarbonyl)ethyl]-2-[(3-N-t-butyloxycarbonylaminomethylphenyl)methyl]-3-oxo (8-3)

Treatment of 8-2 (0.80 g, 2.02 mmoles) with β-alanine t-butyl ester (0.35 g, 2.28 mmoles), BOP (1.35 g, 3.04 mmoles) and Et₃N (14.3 mmoles) as described for 1–11 gave crude 8-3. This was purified by flash chromatography on silica gel eluting with hexane (6)/acetone (4) to give pure 8-3.

¹H NMR (300 MHz, CDCl₃) δ1.45 (9H, s), 1.47 (9H, s), 2.59 (2H, t), 3.72 (2H, m), 4.30 (4H, s), 4.82 (2H, s), 4.88 (1H, m), 7.28 (5H, m), 7.48 (1H, d), 8.08 (1H, d), 8.19 (1H, s).

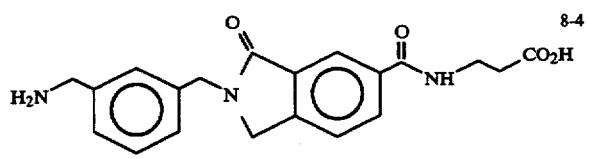

1-H-Isoindole-5-carboxamide, 2,3-dihydro-N-(2-carboxyethyl)-2-[(3-aminomethylphenyl)methyl]-3oxo (8-4)

8-3 (0.872 g, 1.67 mmoles) was dissolved in EtOAc (25 ml) and treated with HCl as described for 6-4 to give pure 8-4.

¹H NMR (300 MH₃, CD₃OD) δ 2.58 (2H, t), 3.56 (2H, t), 4.00 (4H, s), 4.42 (2H, s), 7.32 (4H, m), 7.52 (1H, d), 7.95 (1H, d), 8.11 (1H, s).

SCHEME 9

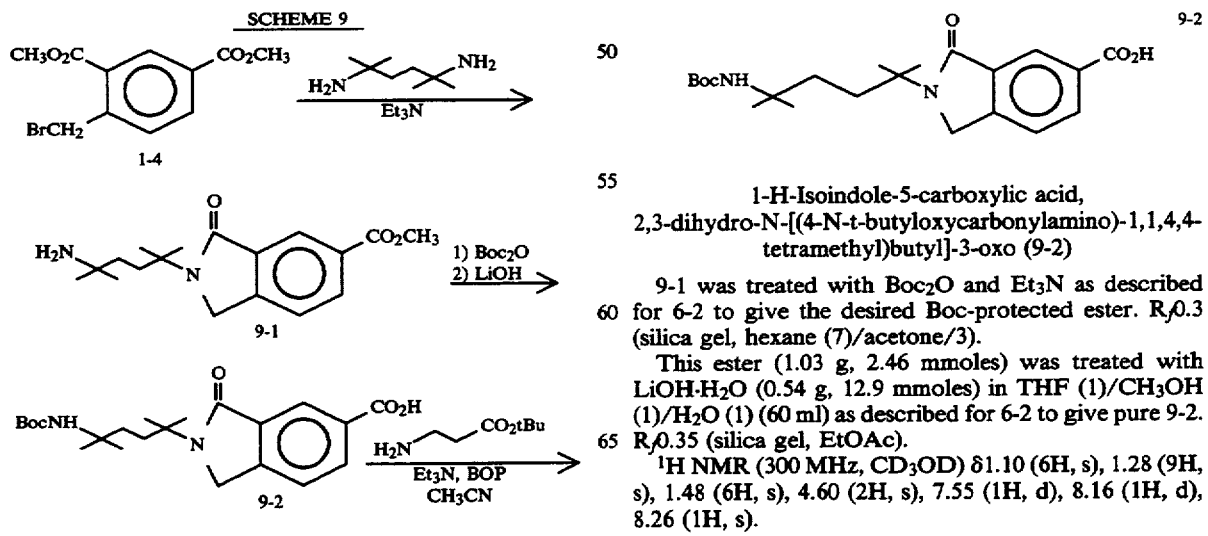

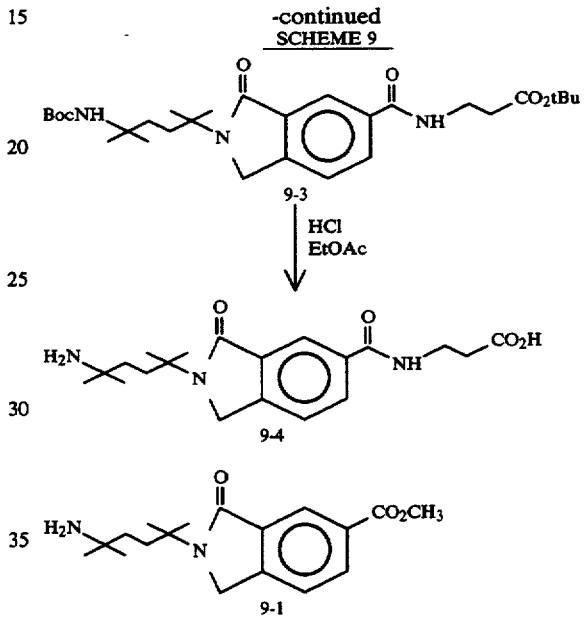

Methyl- 1H-Isoindole-5-carboxylate, 2,3-dihydro-N-[(4-amino-1,1,4,4tetramethyl)butyl]-3-oxo (9-1)

Treatment of 1-4 (2.51 g, 8.74 mmoles) with 1,1,4,4,-tetramethyl-1,4-diaminobutane (1.50 g, 10.40 mmoles) as described for 1–9 provided 9-1. R/0.25 silica gel, 10% CH₃OH in CHCl₃/NH₄OH.

1-H-Isoindole-5-carboxylic acid, 2,3-dihydro-N-[(4-N-t-butyloxycarbonylamino)-1,1,4,4-tetramethyl)butyl]-3-oxo (9-2)

9-1 was treated with Boc₂O and Et₃N as described for 6-2 to give the desired Boc-protected ester. R/0.3 (silica gel, hexane (7)/acetone/3).

This ester (1.03 g, 2.46 mmoles) was treated with LiOH·H₂O (0.54 g, 12.9 mmoles) in THF (1)/CH₃OH (1)/H₂O (1) (60 ml) as described for 6-2 to give pure 9-2. R/0.35 (silica gel, EtOAc).

¹H NMR (300 MHz, CD₃OD) δ1.10 (6H, s), 1.28 (9H, s), 1.48 (6H, s), 4.60 (2H, s), 7.55 (1H, d), 8.16 (1H, d), 8.26 (1H, s).

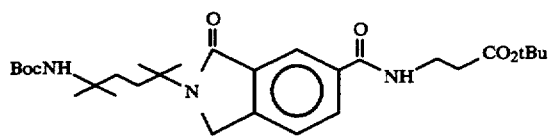

1-H-Isoindole-5-carboxamide, 2,3-dihydro-N-[2-t-butyloxy-carbonyl)ethyl]-2-[4-(N-t-butyloxycarbonyl-amino)-(1,1,4,4-tetramethyl)butyl]-3-oxo (9-3)

9-2 (1.05 g, 2.83 mmoles) was treated with [β-alanine t-butyl ester (0.48 g, 3.12 mmoles), Et₃N (20.0 moles) and BOP (1.91 g, 4.31 mmoles) in CH₃ CN (15 ml) as described for 1-11 to provide crude 9-3. This was purified by flash chromatography on silica gel eluting with pet ether (7)/acetone (3) to give pure 9-3. R/0.3 silica gel, pet ether (7)/acetone (3).

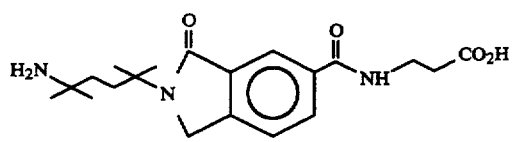

1-H-Isoindole-5-carboxamide, 2,3-dihydro-N-(2-carboxyethyl)-2-[(4-amino-1,1,4,4-tetramethyl)butyl]-3-oxo (9-4)

9-3 (1.23 g) was dissolved in EtOAc (25 ml), cooled to −78° and treated with HCl gas as described for 6-4 to give pure 9-4.

¹H NMR (300 MHz, CD₃OD) a 1.26 (6H, s), 1.53 (SH, m), 2.59 (2H, t), 3.57 (2H, m), 4.63 (2H, s), 7.57 (1H, d), 7.98 (1H, d), 8.06 (1H, s).

SCHEME 10

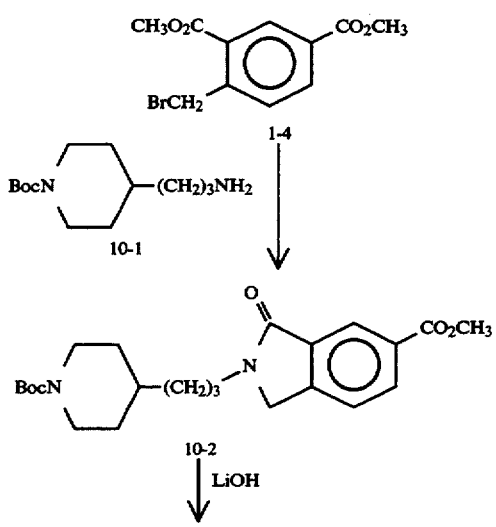

-continued
SCHEME 10

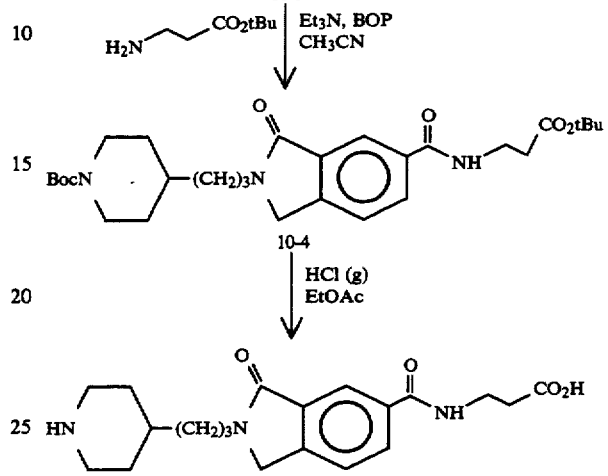

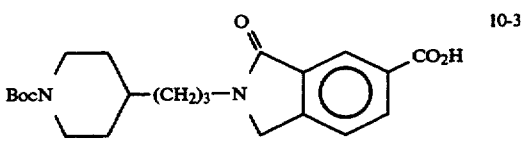

Methyl-1H-Isoindole-5-carboxylate, 2,3-dihydro-N-[3-(4-N-t-butyloxycarbonylpiperidinyl)-propyl]-3-oxo (10-2)

Treatment of 1-4 (4.59 g, 16.0 mmoles) with 3-(4-N-t-butyloxycarbonylpiperidinyl)propylamine (prepared from 1-6 by nitrile formation followed by catalytic hydrogenation) (4.36 g, 15.6 mmoles) as described for 1-9 gave crude 10-2. This was purified by flash chromatography on silia gel eluting with hexane (3)/ethyl acetate (1) to give pure 10-2.

¹H NMR (300 MHz, CDCl₃) δ1.10 (2H, m), 1.30 (2H, m), 1.45 (9H, s), 1.68 (4H, m), 2.66 (2H, m), 3.62 (2H, t), 3.95 (3H, s), 4.10 (2H, m), 4.44 (2H, s), 7.52 (1H, d), 8.23 (1H, d), 8.50 (1H, s).

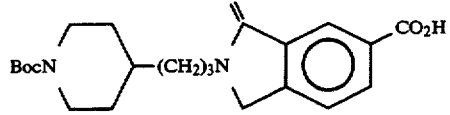

1-H-Isoindole-5-carboxylic acid, 2,3-dihydro-N-[3-(4-N-t-butyloxycarbonylpiperidinyl)propyl]-3-oxo (10-3)

Treatment of 10-2 (2.79 g, 6.91 mmoles) with LiOH·H₂O (1.48 g, 35.2 mmoles) in THF (1)/MeOH (1)/H₂O (1) as described for 1-10 provided 10-3 as a white solid.

¹H NMR (300 MHz, CD₃OD) δ 0.95 (2H, m), 1.23 (3H, m), 1.35 (9H, s), 1.66 (3H, m), 2.65 (2H, m), 3.56 (2H, t), 3.96 (2H, bd), 4.50 (2H, s), 7.60 (1H, d), 8.17 (1H, d), 8.30 (1H, s).

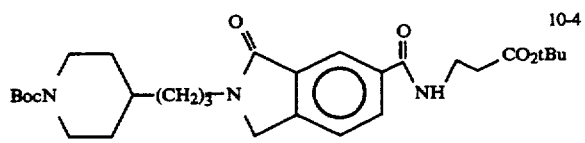

1-H-Isoindole-5-carboxamide, 2,3-dihydro-N-[3-(t-butyloxycarbonyl)ethyl]-2-[3-(4-N-t-butyloxycarbonyl-piperdinyl)propyl]-3-oxo (10-4)

Treatment of 10-3 (1.28 g, 3.28 mmoles) with β-alanine t-butyl ester (0.64 g, 3.52 mmoles), Et₃N (3.3 mmoles), BOP (2.16 g) in CH₃CN as described for 1–11 gave crude 10-4. This was purified by flash chromatography on silica gel eluting with hexane (7)/acetone (3) to give pure 10-4.

¹H NMR (300 MHz, CDCl₃) δ1.09 (2H, m), 1.30 (3H, m), 1.45 (9H, s), 1.68 (4H, m), 2.62 (4H, m), 3.62 (2H, t), 3.70 (2H, t), 4.08 (2H, bd), 4.23 (2H, s), 7.52 (1H, d), 8.10 (1H, d), 8.13 (1H, s).

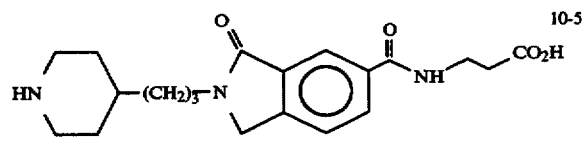

1-H-Isoindole-5-carboxamide, 2,3-dihydro-N-(2-carboxyethyl)-2-[3-(4-piperidinyl)propyl]-3-oxo (10-5)

Treatment of 10-4 (1.18 g) in EtOAc (30 ml) −78° with HCl gas as described for 6-4 gave pure 10-5 as a white solid. R$_f$0.4 (silica gel, EtOAc).

¹H NMR (300 MHz, CD₃OD) δ1.30 (4H, m), 1.67 (4H, m), 1.89 (2H, bd), 2.60 (2H, t), 2.40 (2H, t), 3.19 (2H, bd), 3.58 (4H, m), 4.50 (2H, s), 7.60 (1H, d), 7.99 (1H, d), 8.08 (1H, s).

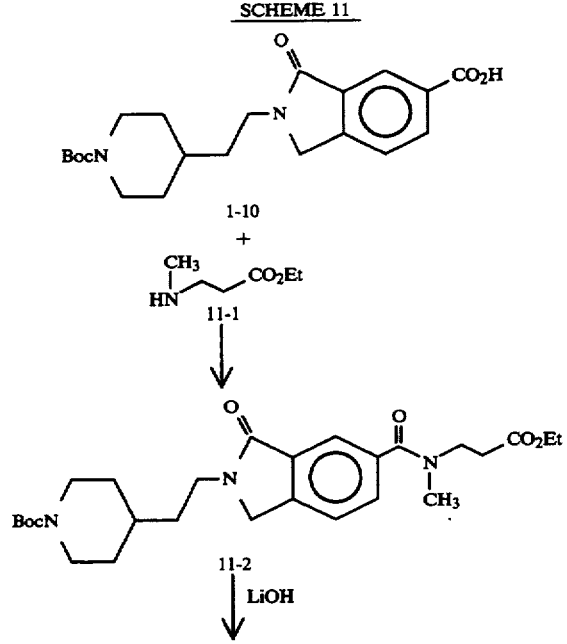

-continued
SCHEME 11

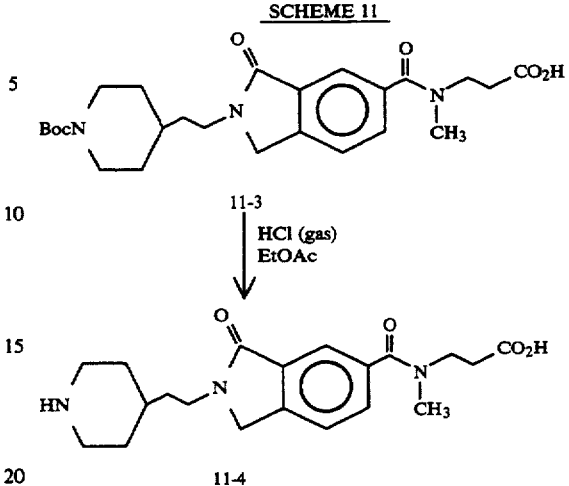

1-H-Isoindole-5-carboxamide, 2,3-dihydro-N-[N-methyl-N-2(carboethoxy)ethyl]-2-[2-(4-N-t-butyloxycarbonyl-piperidinyl)-ethyl]-3-oxo (11-2)

Treatment of 1-10 (0.2 g, 0.54 mmoles) with ethyl 3-(N-methyl)aminopropionate (0.14 g, 1.08 mmoles) (Appl. Polymer Sci., 1969, 13, 227), N-methylmorpholine (1.08 mmoles), and BOP (0.35 g, 0.8 mmoles) in CH₃ CN (3 ml) as described for 1-11 gave crude 11-2. This was purified by flash chromatography on silica gel eluting with EtOAc to give pure 11-2 as a white solid.

¹H NMR (300 MHz, CD₃OD) δ1.20 (6H, m), 1.45 (9H, s), 1.67 (2H, q), 1.80 (2H, bd), 2.73 (2H, m), 3.00 (3H, s), 3.08 (1H, bs), 3.71 (2H, t), 3.84 (1H, m), 4.05 (4H, m), 4.17 (1H, m), 4.56 (2H, s), 7.66 (2H, m), 7.77 (1H, s).

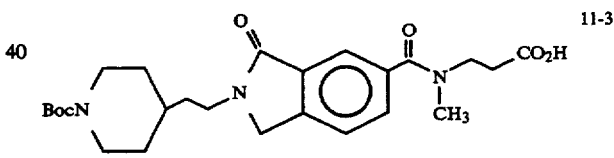

1-H-Isoindole-5-carboxamide, 2,3-dihydro-N-[N-methyl-N-(2-carboxyethyl)]-2-[2-(4-N-t-butyloxycarbonylpiperidinyl)ethyl]-3-oxo (11-3 )

11-2 (0.23 g, 0.49 mmoles) was treated with LiOH·H₂O (0.096 g, 2.3 mmoles) as described for 8-2 to give 11-3 as a white solid.

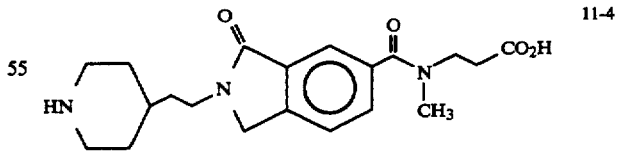

1-H-Isoindole-5-carboxamide, 2,3-dihydro-N-[N-methyl-N-(2-carboxyethyl)]-2-[(4-piperidinyl)ethyl]-3-oxo (11-4)

11-3 (0.2 g, 0.45 mmoles) in EtOAc was treated with HCl gas as described for 8-4 to give pure 11-4 as a white solid.

¹H NMR (300 MHz, CD₃OD) δ1.14 (1H, t), 1.37 (2H, m), 1.50 (1H, m), 1.63 (2H, q), 1.92 (2H, bd), 2.51 (1H, t), 2.67 (1H, t), 2.83 (2H, m), 3.31 (2H, bd), 3.54 (1H, t), 3.60 (2H, t), 3.73 (1H, t), 4.49 (2H, s), 7.57 (2H, q), 7.65 (1H, s).

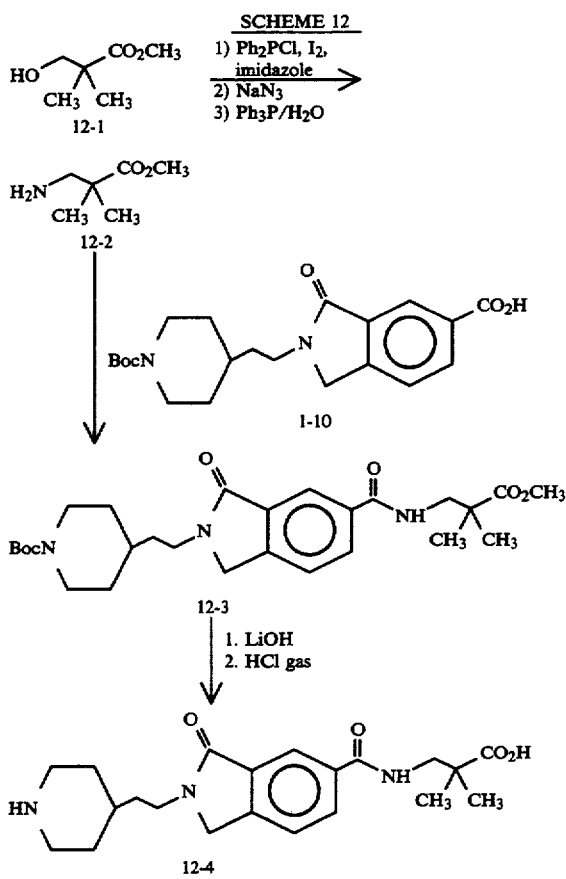

Methyl 3-amino-2,2-dimethylpropionate (12-2)

12-1 (Aldrich, 5.0 g, 38 mmoles) in toluene (150 ml) at room temperature was treated with chlorodiphenyl phosphine (49.4 mmoles) followed by imidazole (5.7 g, 83.6 moles) and I₂ (12.5 g, 49.4 mmoles) and the resulting brown solution was stirred for 0.5 hours. This mixture was poured into 150 ml saturated Na₂CO₃ solution and the organic layer was separated and washed with saturated Na₂CO₃ solvent, 5% Na₂SO₄ solution, H₂O, and 10% KHSO₄ solution. The nearly colorless organic layer was then washed with brine, dried (Na₂SO₄) and the solvent was removed to produce a yellow residue.

This was purified by flash chromatography on silica gel eluting with hexane (6)/EtOAc (4) to give the desired iodo intermediate as an oil. R$_f$0.9 (silica gel, hexane (6)/EtOAc (4)).

¹H NMR (300 MHz, CDCl₃) δ1.38 (6H, s), 3.40 (2H, s), 3.75 (3H, s).

This iodo compound (3.9 g, 16 mmoles) was dissolved in DMSO (80 ml) and treated with NaN₃ (2.1 g, 32 mmoles) at 70° for 2 hours. The cooled reaction next was diluted with EtOAc and extracted with H₂O and brine. The organic phase was washed with brine, dried (Na₂SO₄) and the solvent was removed to give the desired azide as a foam.

¹H NMR (300 MHz, CDCl₃) δ1.25 (6H, s), 3.45 (2H, s), 3.75 (3H, s).

This azide (2.0 g, 12.7 mmoles) was dissolved in THF (50 ml) and treated with H₂O (25 ml) and triphenyl phosphine (13.3 g, 50.8 mmoles) at room temperature for 2 hours. The THF was removed under vacuum and the resulting residue was acidified to pH 2–3 with 10% KHSO₄ solution. This was filtered to remove triphenyl phosphine and the filtrate was extracted with EtOAc. The acidic aqueous phase was then basified with 10% NaOH and extracted with Et₂O. The combined ether extracts were washed with brine, dried (Na₂SO₄) and the solvent removed to give 12-2 as a clear oil. R$_f$0.35 (silica gel, CH₂Cl₂ (9)/CH₃OH (1)/H₂O (1).

¹H NMR (300 MHz, CD₃OD) δ1.22 (6H, s), 2.75 (2H, s), 3.75 (3H, s).

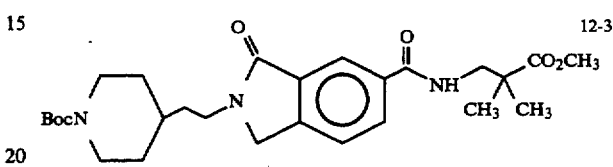

1-H-Isoindole-5-carboxamide, 2,3-dihydro-N-[(2-carbomethoxy-2methyl)propyl]-2-[2-(4-N-t-butyloxycarbonyl-piperidinyl)ethyl]-3-oxo (12-3)

Treatment of 1-10 (1.0 g, 2.7 mmoles) with 12-2 (0.524 g, 4.0 mmoles), N-methylmorpholine (4.0 mmoles) and BOP (1.78 g, 4.0 mmoles) in CH₃CN (15 ml) as described for 6-3 provided crude 12-3. This was purified by flash chromatography on silica gel eluting with EtOAc (9)/Hexane (1) to give pure 12-3 as a white solid.

¹H NMR (300 MHz, CDCl₃) δ1.20 (2H, m), 1.33 (6H, s), 1.48 (9H, s), 1.80 (2H, bd), 2.71 (2H, bt), 3.64 (2H, d), 3.73 (2H, t), 3.77 (3H, s), 4.13 (2H, m), 4.44 (2H, s), 6.94 (1H, t), 7.57 (1H, d), 8.11 (1H, d), 8.13 (1H, s).

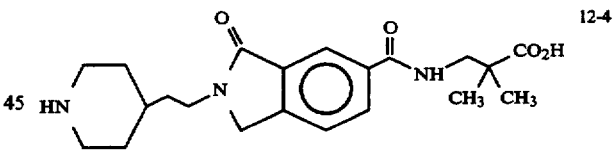

1-H-Isoindole-5-carboxamide, 2,3-dihydro-N-[(2-carboxy-2-methyl)-propyl]-2-[2-(4-piperidinyl)ethyl]-3-oxo (12-4)

12-3 (0.5 g, 1.0 mmoles) was treated with LiOH·H₂O (0.216 g, 5.0 mmoles) as described for 6-2 to give the desired acid as a white solid.

¹H NMR (300 MHz, CD₃OD) δ1.13 (2H, m), 1.25 (6H, s), 1.45 (9H, s), 1.65 (2H, m), 1.80 (2H, bd), 2.72 (2H, m), 3.68 (2H, m0, 3.70 (2H, t), 4.05 (2H, bd), 4.56 (2H, s), 7.67 (1H, d), 8.04 (1H, dd), 8.15 (s).

This acid (0.40 g) was dissolved in EtOAc and was treated with HCl gas as described for 6-4 to give pure 12-4 as a white solid.

¹H NMR (300 MHz, D₂O) δ 1.14 (6H, s), 1.35 (2H, m), 1.49 (1H, m), 1.60 (2H, q), 1.90 (2H, bd), 2.81 (2H, t), 3.30 (2H, bd), 3.47 (2H, s), 3.57 (2H, t), 4.48 (2H, s), 7.55 (1H, d), 7.82 (1H, d), 7.90 (1H, s).

SCHEME 13

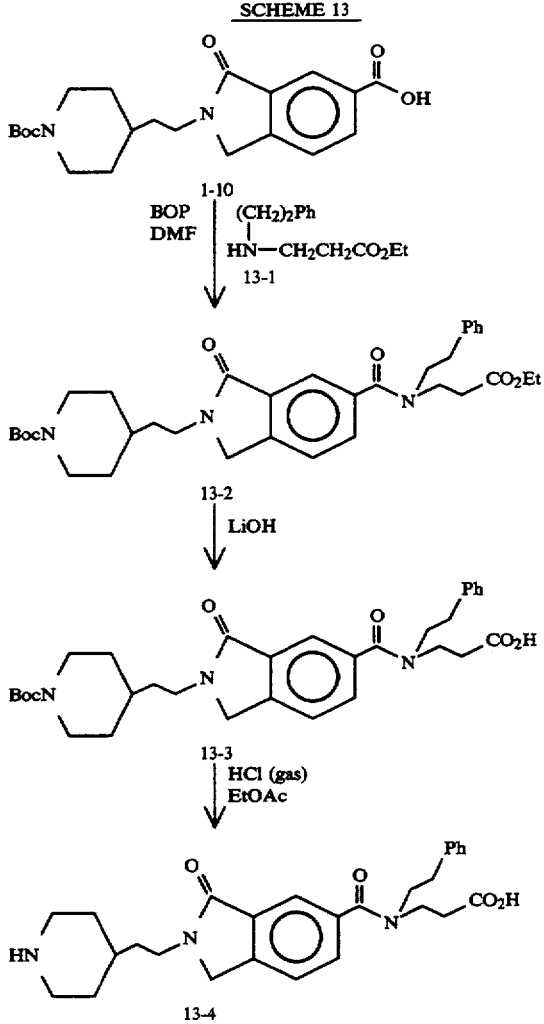

1-H-Isoindole-5-carboxamide,
2,3-dihydro-N-[N-phenethyl-N-2carboethoxyethyl]-2-
[2-(4-N-t-butyloxy-carbonylpiperidinyl)ethyl]-3-oxo
(13-2)

1-10 (0.388 g, 1.0 mmoles) was treated with ethyl 3-(N-phenethyl)aminopropionate (0.22 g, 1.0 mmoles) (prepared by treatment of phenethylamine with ethyl acrylate), triethylamine (0.243 g, 2.4 mmoles) and BOP (0.53 g, 1.2 mmoles) in DMF (15 ml) and the resulting solution was stirred at room temperature for 18 hours. The solvent was then removed and the residue was diluted with $H_2O$ (100 ml) and extracted with EtOAc (3×100 ml portions). The organic phase was washed with 10% $KHSO_4$ solution, brine, saturated $NaHCO_3$ solution, brine and dried ($Na_2SO_4$). Solvent removal gave 13-2 as an oil.

$^1H$ NMR (300 MHz, $CDCl_3$) δ1.07–1.35 (6H, m), 1.48 (9H, s), 1.62 (3H, m), 1.75 (2H, bd), 2.72 (4H, m), 3.00 (1H, m), 3.50 (2H, m), 3.67 (2H, t), 3.83 (2H, m), 4.10 (5H, m), 4.38 (2H, s), 6.94 (1H, bs), 7.30 (6H, m), 7.50 (1H, m), 7.67 (1H, m).

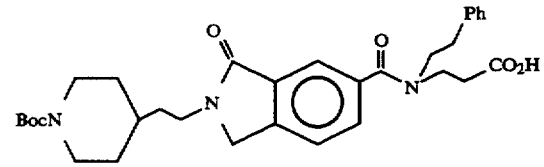

1-H-Isoindole-5-carboxamide,
2,3-dihydro-N-[N-phenethyl-N-(2-carboxyethyl)]-2-[2-
(4-N-t-butyloxycarbonylpiperidinyl)ethyl]-3-oxo (13-3)

13-2 (0.60 g, 1.0 mmoles) was treated with $LiOH·H_2O$ (0.127 g, 3.0 mmoles) as described for 6-2 to give 13-3 as a white solid. $R_f$ 0.45 (silica gel, $CHCl_3$ (9)/MeOH (5)/HOAc (1)).

$^1H$ NMR (300 MHz, $CDCl_3$) δ1.17 (2H, m), 1.47 (9H, s), 1.63 (3H, m), 1.75 (2H, bd), 2.67 (2H, t), 2.80 (3H, m), 3.42 (1H, m), 3.57 (1H, m), 3.67 (2H, t), 3.80 (2H, m), 4.08 (3H, m), 4.37 (2H, s), 6.93 (1H, m), 7.25 (6H, m), 7.48 (1H, m), 7.70 (1H, m).

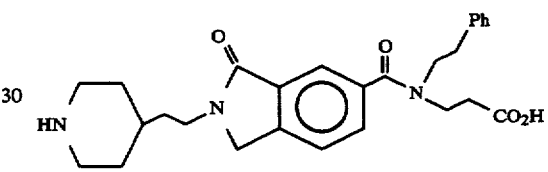

1-H-Isoindole-5-carboxamide,
2,3-dihydro-N-[N-phenethyl-N-(2-carboxyethyl)]-2-[2-
(4-piperidinyl)ethyl]-3-oxo (13-4)

13-3 was treated with HCl (gas) in EtOAc as described for 6-4 to give pure 13-4 as a white solid. $R_f$ 0.25 (silica gel, EtOH (10)/$H_2O$ (1)/$NH_4OH$ (1)).

$^1H$ NMR (300 MHz, $CD_3OD$) δ1.45 (2H, m), 1.62 (2H, m), 1.71 (2H, m), 2.07 (2H, bd), 2.45 (1H, m), 2.78 (2H, m), 2.95 (3H, m), 3.37 (3H, bd), 3.57 (1H, bt), 3.72 (2H, t), 3.83 (2H, m), 3.55 (2H, s), 6.95 (1H, m), 7.20 (4H, bs), 7.33 (1H, bs), 7.45 (1H, bs), 7.55 (1H, m), 7.66 (1H, m).

SCHEME 14

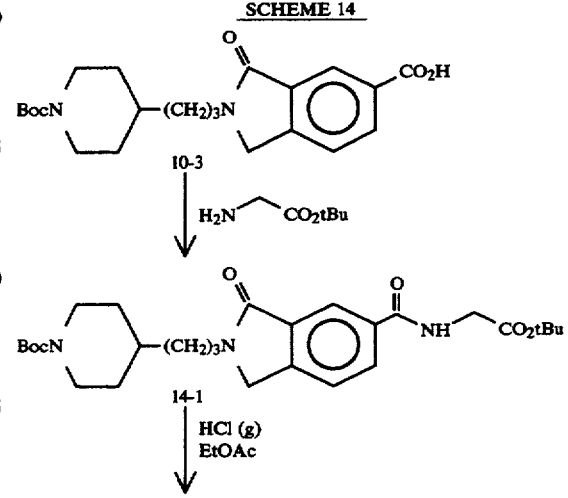

-continued
SCHEME 14

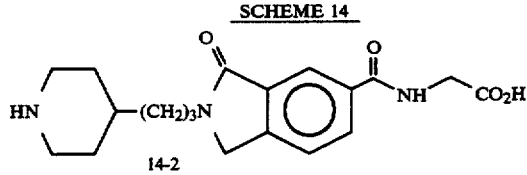

1-H-Isoindole-5-carboxamide, 2,3-dihydro-N-[t-butyloxycarbonylmethyl]-2-[3-(4-N-t-butyloxycarbonylpiperidinyl)propyl]-3-oxo (14-1)

Treatment of 10-3 with glycine t-butyl ester as described for 6-3 gave 14-1.

$^1$H NMR (300 MHz, CDCl$_3$) a 1.13 (2H, m), 1.30 (2H, m), 1.41 (9H, s), 1.52 (9H, s), 1.73 (4H, m), 2.69 (2H, t), 3.65 (2H, t), 4.10 (2H, bd), 4.16 (2H, d), 4.45 (2H, s), 7.53 (1H, d), 8.10 (1H, d), 8.22 (1H, s).

1-H-Isoindole-5-carboxamide, 2,3,-dihydro-N-[carboxymethyl]-2-[3-(4-piperidinyl)-propyl]-3-oxo (14-2)

Treatment of 14-1 with HCl gas in EtOAc as described for 6-4 gave 14-2 as a white solid.

hu 1H NMR (300 MHz, CD$_3$OD) δ1.30 (4H, m), 1.65 (4H, m), 1.90 (2H, bd), 2.59 (2H, t), 2.90 (2H, t), 3.30 (2H, bd), 3.58 (4H, m), 4.50 (2H, s), 7.58 (1H, d), 7.98 (1H, d), 8.07 (1H, s).

give crude 15-1. This was purified by flash chromatography on silica gel eluting with 25% CH$_3$OH/CHCl$_3$(NH$_3$) to give pure 15-1 as a solid.

$^1$H NMR (300 MHz, CD$_3$OD) δ1.61 (2H, m), 1.75 (2H, m), 2.90 (2H, t), 3.24 (1H, m), 3.63 (2H, t), 3.85 (3H, s), 4.53 (2H, s), 7.62 (1H, d), 8.18 d) 8.28 (1H, s).

1-H-Isoindole-5-carboxylic acid-2,3-dihydro-N-[2-(4-N-t-butyloxycarbonyamino)butyl]-3-oxo(15-2)

15-1 (1.11 g, 4.24mmoles) was treated with Boc$_2$O (1.17 g, 5.36 mmoles) as described for 3-1. Crude residue was purified by flash chromatography on silica gel eluting with 30% acetone/hexane to give the desired protected ester as an oil. R$_f$0.7 silica gel, 30% acetone/hexane.

This ester (0.85 g, 2.34mmoles) was dissolved in THF(1)/CH$_3$OH(1)/H$_2$O(1) (30ml) and treated with LiOH·H$_2$O (0.52 g, 12.4 mmoles) as described for 3-2 to give 15-2 as a white solid.

$^1$H NMR (300 MHz, CD$_3$OD) δ1.36 (9H, s), 1.44 (2H, m), 1.66 (4H, m), 3.01 (2H, t), 3.60 (2H, t), 4.54 (2H, s), 7.62 (1H, d), 8.20 (1H, d), 8.35 (1H, s).

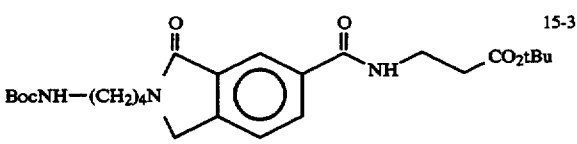

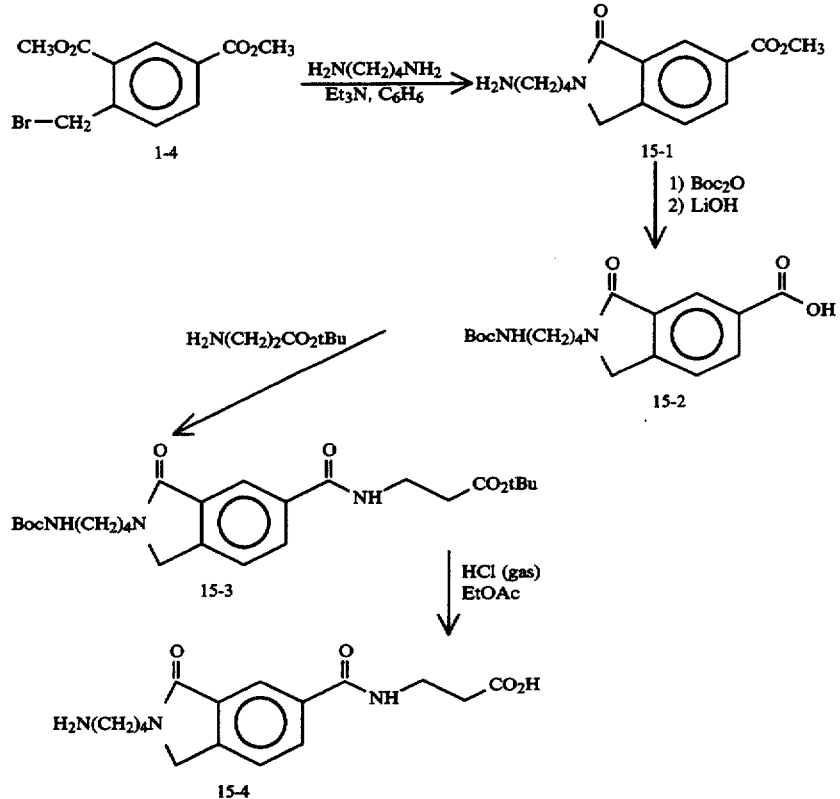

Methyl-1H-Isoindole-5-carboxylate, 2,3-dihydro-N-[2-(4-aminobutyl)]-3-oxo(15-1)

1-4 (2.56 g, 8.92mmoles)was treated with 1,4-diaminobutane (10.9 mmoles) as described for 1-9 to

1-H-Isoindole-5-carboxamide, 2,3-dihydro-N-[2-(t-butyloxy-carbonyl)ethyl]-2-[4-(N-t-butyloxycarbonyl)butyl]-3-oxo(15-3)

Treatment of 15-2 (0.75 g, 2.07 mmoles) in CH₃CN (12 ml) with β-alanine t-butyl ester (0.39 g, 2.54 mmoles), Et₃N (14.3 mmoles) and BOP (1.40 g, 3.16 mmoles) as described for 3—3 gave crude 15-3. This was purified by flash chromatography on silica gel eluting with 75% EtOAc/hexane to give pure 15-3 as a white solid. R$_f$ 0.25 (silica gel, 75% EtOAc/hexanes).

$^1$H NMR (300 MHz, CDCl₃) δ1.42 (9H, s), 1.44 (9H, s), 1.52 (2H, m), 1.77 (2H, m), 2.55 (2H, t), 3.19 (2H, m), 3.67 (4H, m), 4.43 (2H, s), 7.00 (1H, bt), 7.52 (1H, d), 8.09 (1H, d), 8.10 (1H, s).

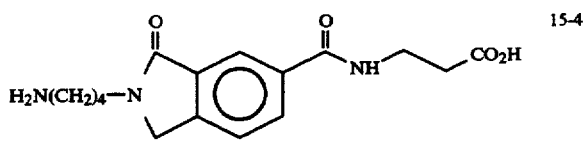

1-H-Isoindole-5-carboxamide, 2,3-dihydro-N-[2-carboxyethyl]-2-[4-aminobutyl]-3-oxo(15-4)

Treatment of 15-3 (0.51 g, 1.07 mmoles) in EtOAc with HCl gas as described for 3—4 provided pure 15-4 as a white solid.

$^1$H NMR (300 MHz, D₂O), δ1.63 (4H, m), 2.64 (2H, t), 2.92 (2H, t), 3.52 (4H, m), 4.46 (2H, s), 7.55 (1H, d), 7.81 (1H, d), 7.85 (1H, s).

SCHEME 16

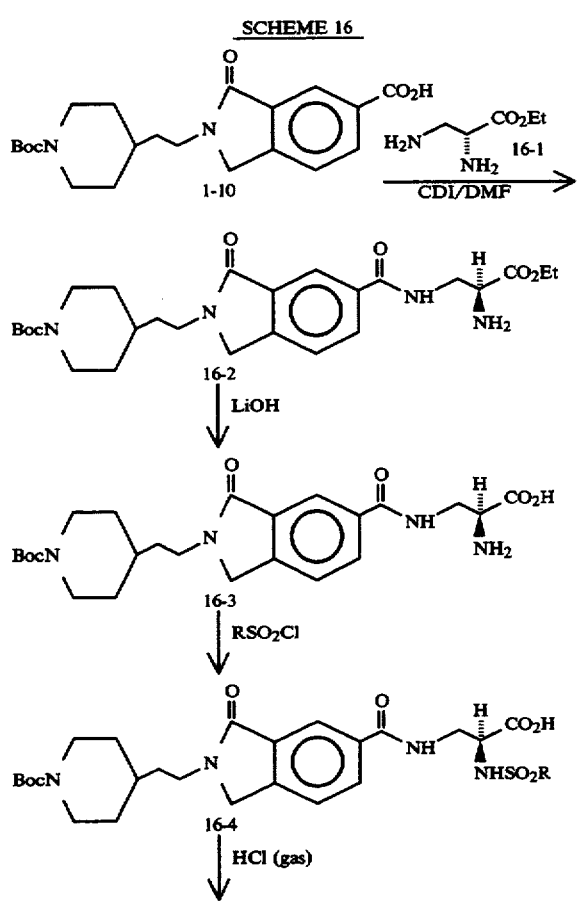

-continued
SCHEME 16

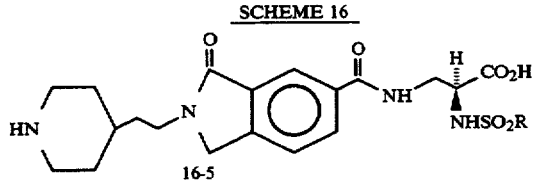

1-H-Isoindole-5-carboxamide, 2,3-dihydro-N-[ethyl-3-(2(S)aminopropionate)]-2-[2-(4-N-t-butyloxycarbonylpiperidinyl]-3-oxo (16-2)

A solution of 1-10 (1.5 g, 3.87 mmoles) in DMF (15 ml) at room temperature was treated with carbonyl diimidazole (0.627 g, 3.87 mmoles) (CDI) and after 2 hours this solution was added dropwise to a DMF solution of ethyl 2(S),3-diaminopropionate (1.5 g, 7.74 mmoles) and N-methylmorpholine (23.2 mmoles). The reaction mixture was then stirred at room temperature for 16 hrs.

The solvent was then removed and the residue was dissolved in EtOAc and 10% aqueous KHSO₄ solution. The aqueous phase was separated, washed with EtOAc and made basic to pH 12. This was extracted with EtOAc, and the extracts were combined, washed with brine, and dried (Na₂SO₄). Solvent removal provided 16-2.

$^1$H NMR (300 MHz, CD₃OD) δ1.24 (2H, m), 1.46 (3H, t), 1.43 (9H, s), 1.66 (2H, q), 1.80 (2H, bd), 3.67 (4H, m), 4.10 (2H, bd), 4.17 (2H, q), 4.57 (2H, s), 7.04 (1H, d), 7.67 (1H, m), 8.06 (1H, m), 8.17 (1H, d).

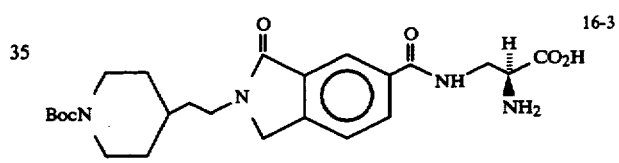

1-H-Isoindole-5-carboxamide, 2,3-dihydro-N-[3-[2(S)-aminopropanoic acid]-2-[2-(4-N-t-butyloxycarbonylpiperidinyl]-3-oxo (16-3)

Treatment of 16-2 (0.6 g, 1.2 mmoles) with LiOH·H₂O (0.25 g, 6.0 mmoles) as described for 1-10 gave 16-3.

$^1$H NMR (300 MHz, D₂O) δ 0.92 (2H, m), 1.27 (9H, s), 1.46 (4H, m), 2.58 (2H, t), 3.48 (4H, m), 3.83 (2H, bd), 4.38 (2H, s), 6.96 (1H, s), 7.50 (1H, d), 7.82 (1H, d), 7.87 (1H, s).

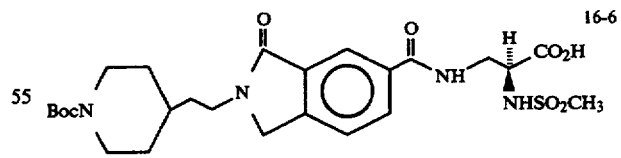

1-H-Isoindole-5-carboxamide, 2,3-dihydro-N-[3-[2(S)-methylsulfonylamino)propanoic acid)]-2-[2-(4-N-t-butyloxycarbonylpiperidinyl]-3-oxo (16-6)

A solution of 16-6 (0.55 g, 1.2 mmoles) in H₂O (15 ml)/dioxane (3 ml) was cooled to 0°-10° and treated with 1N NaOH soln. (1.5 ml) and methane sulfonyl chloride (2.4 mmoles) in 3 ml dioxane was added dropwise while also adding 1N NaOH solution to keep the pH at 10–12. This cycle of CH₃SO₂Cl addition at basic pH was carried out 5 times at which point all 16-6 was consumed. The acidity was carefully adjusted to pH 2–3 with 10% KHSO₄ solution and this was extracted with EtOAc (4 portions). The combined organics were washed with brine, dried (Na₂SO₄) and the solvent removed. The residue was purified by flash chromatography on silica gel eluting with CH₂Cl₂ (9)/MeOH (0.8)/HOAc (0.8) to give 16-6 as a white solid. $R_f$ 0.31.

¹H NMR (300 MHz, CD₃OD) δ 1.25 (2H, m), 1.45 (9H, s), 1.65 (2H, q), 1.80 (2H, bd), 2.72 (2H, m), 2.97 (3H, s), 3.70 (3H, m), 3.86 (1H, m), 4.05 (2H, bd), 4.34 (1H, m), 4.56 (2H, s), 7.66 (1H, d), 8.08 (1H, d), 8.19 (1H, s).

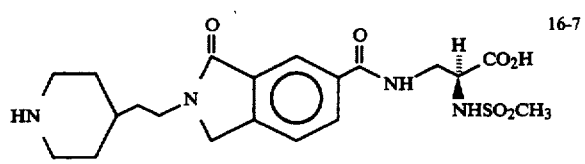

1-H-Isoindole-5-carboxamide, 2,3-dihydro-N-[3-(2(S)-methylsulfonylamino)propionic acid]-2-[2-(4-piperidinyl)ethyl]-3-oxo (16-7)

Treatment of 16-6 (0.22 g, 0.39 mmoles) with HCl gas in EtOAc as described for 1-12 gave 16-7 as a white solid.

¹H NMR (300 MHz, D₂O) δ 1.35 (2H, m), 1.59 (2H, m), 1.87 (2H, bd), 2.78 (2H, bt), 2.95 (3H, m), 3.27 (2H, bd), 3.55 (3H, m), 3.78 (1H, m), 4.20 (1H, m), 4.48 (2H, s), 7.56 (1H, m), 7.87 (1H, m), 7.95 (1H, bs).

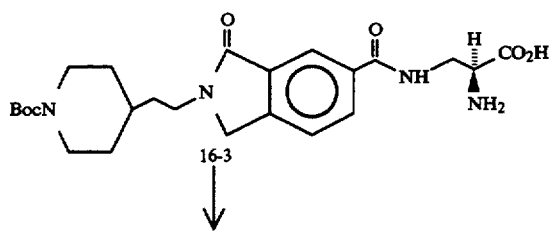

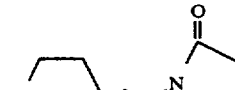

1-H-Isoindole-5-carboxamide, 2,3-dihydro-N-[3-(2(S)-n-butylsulfonylamino)propanoic acid]-2-[2-(4-N-t-butyloxy-carbonylpiperidinyl)]-3-oxo (16-8)

Treatment of 16-3 (0.836 mmoles) with n-butylsulfonyl chloride (1.67 mmoles) as described for 16-6 gave 16-8 as a white solid.

¹H NMR (300 MHz, CD₃OD) δ 0.85 (6H, m), 1.13 (2H, m), 1.35 (4H, m), 1.45 (9H, s), 1.65 (2H, m), 1.75 (2H, m), 2.70 (2H, m), 3.04 (2H, t), 3.68 (2H, m), 3.83 (1H, m), 4.04 (2H, bd), 4.53 (2H, s), 7.62 (1H, d), 8.05 (1H, d), 8.18 (1H, s).

1-H-Isoindole-5-carboxamide, 2,3-dihydro-N-[3-(2(S)-n-butylsulfonylamino)propionic acid]-2-[2-(4-piperidinyl)ethyl]-3-oxo (16-9)

Treatment of 7-8 in EtOAc with HCl gas as described for 1-12 gave pure 16-9 as a white solid.

¹H NMR (300 MHz, CD₃OD) δ 0.59 (2H, t), 1.12 (2H, m), 1.35 (2H, m), 1.50 (2H, m), 1.59 (2H, m), 1.90 (2H, bd), 2.80 (2H, t), 2.98 (2H, t), 3.29 (2H, bd), 3.42 (1H, m), 3.60 (2H, t), 3.70 (1H, m), 4.50 (2H, s), 7.59 (1H, d), 7.91 (1H, d), 7.98 (1H, s).

SCHEME 17

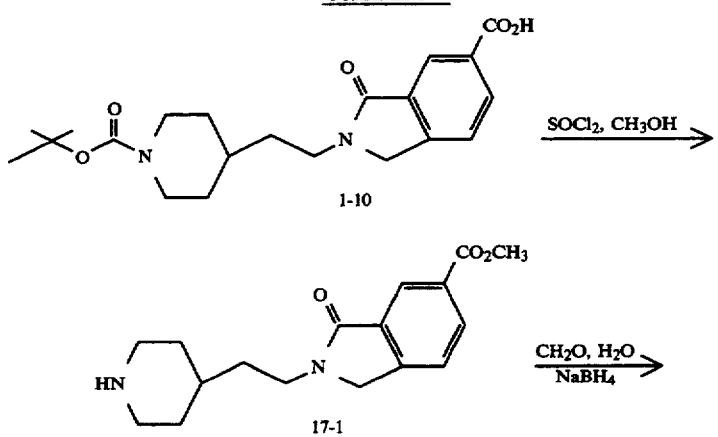

SCHEME 17

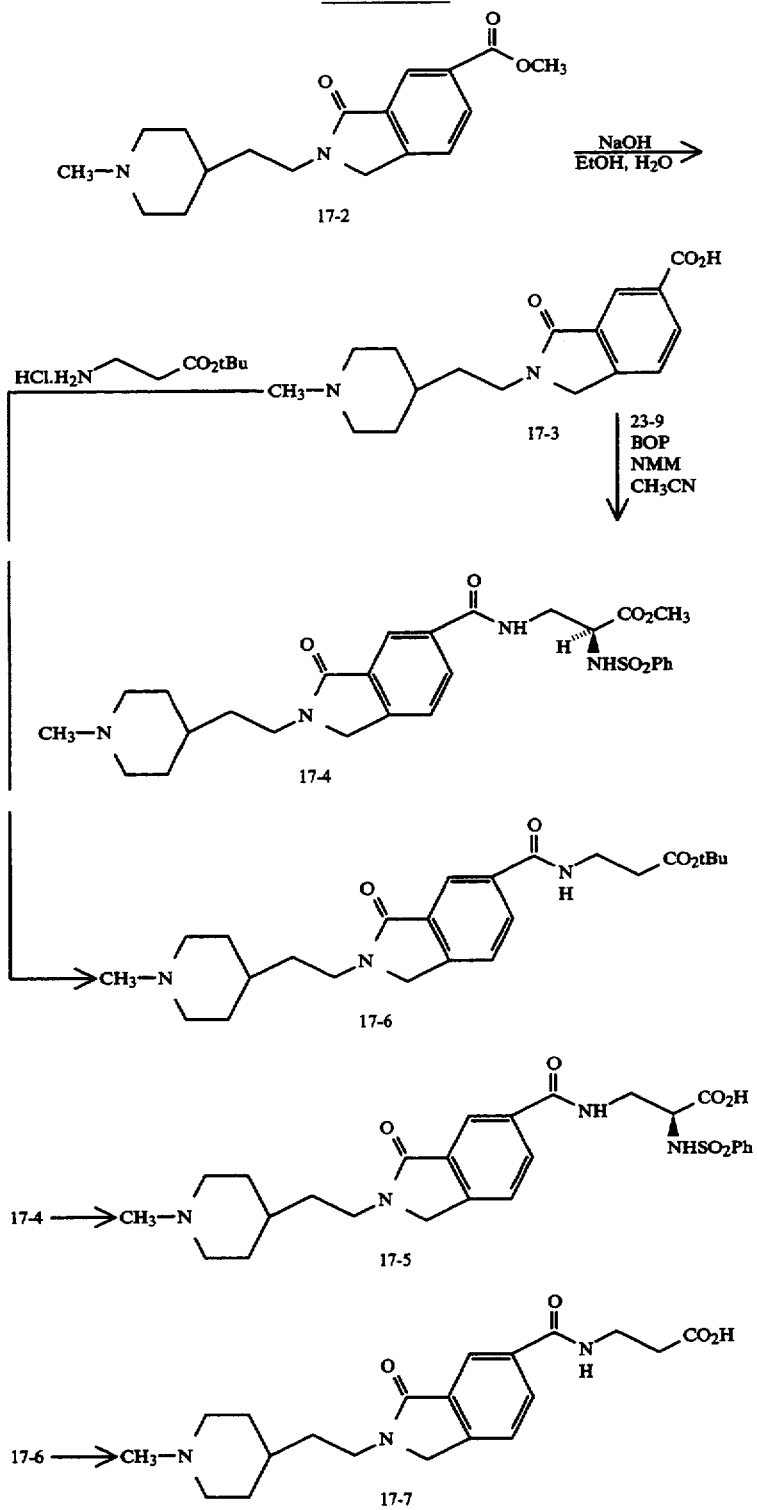

Methyl 1-H-Isoindole-5-carboxylate,
2,3-dihydro-2-[2-(piperidin-4-yl)ethyl]3-oxo (1.7-1)

A solution of 1-10 (1.7 g, 4.4 mmol) in CH$_3$OH (30 mL) was cooled to 0° C. and treated with thionyl chloride (1.6 mL, 22 mmol) dropwise over five minutes. The solution was warmed to room temperature and stirred for 20 h, then concentrated to give 17-1 as a white solid.

R$_f$(10:1:1 EtOH/H$_2$O/NH$_4$OH) 0.29

$^1$H NMR (300 MHz, CD$_3$OD) δ 8.25 (s, 1H), 8.15 (d, 1H), 7.6 (d, 1H), 4.5 (s, 2H), 3.82 (s, 3H), 3.7 (t, 2H), 3.2 (m, 2H), 2.82 (t, 2H), 1.95 (bd, 2H), 1.6 (m, 2H), 1.5 (m, 1H), 1.32 (m, 2H).

Methyl 1-H-Isoindole-5-carboxylate, 2,3-dihydro-2-[2-(N-methyl piperidin-4-yl)ethyl]-3-oxo (17-2)

A solution of 17-1 (1.32 g, 4.4 mmol) in boiling EtOH and treated with aqueous formaldehyde (11.5 mL, 37% by weight in H$_2$O, 0.14 mole) and acetic acid (3.45 mL). After refluxing for 2h, the reaction was cooled to room temperature and treated with NaBH$_4$ (1.17 g, 30.8 mmol). After 5 h the reaction was quenched with 1N HCl, then basified with saturated NaHCO$_3$ and 1N NaOH to pH 10, diluted with H$_2$O (200 mL) and extracted with 4×300 mL CHCl$_3$. The combined organic layers were washed with brine, dried (MgSO$_4$), filtered and evaporated to give 17-2 as an off-white solid.

R$_f$(10:1: 1 EtOH/NH$_4$OH/H$_2$O) 0.2

$^1$H NMR (300 MHz, CDCl$_3$) δ 8.52 (s, 1H), 8.25 (d, 1H), 7.55 (d, 1H), 4.45 (s, 2H), 3.97 (s, 3H), 3.7 (m, 2H), 3.0 (m, 2H), 2.4 (m, 3H), 2.1 (m, 2H), 1.88 (bd, 2H), 1.68 (m, 2H), 1.5 (m, 1H), 1.25 (m, 2H).

1-H-Isoindole-5-carboxylic acid, 2,3-dihydro-2-[2-(N-methylpiperidin-4-yl)ethyl]-3-oxo (17-3)

A solution of 17-2 (1.23 g, 3.9 mmol) in EtOH (20 mL) was treated with 1N NaOH (5.9 mL, 3.9 mmol) at room temperature for 16h, then concentrated to give 17-3 as a yellow solid.

$^1$H NMR (400 MHz, CD$_3$OD) δ 8.4 (s, 1H), 8.21 (d, 1H), 7.6 (d, 1H), 4.55 (s, 2H), 3.7 (m, 2H), 2.85 (d, 2H), 2.23 (s, 3H), 2.0 (m, 2H), 1.85 (m, 2H), 1.7 (m, 2H), 1.35 (m, 3H).

1-H-Isoindole-5-carboxamide, 2,3-dihydro-N-[methyl 3-(2(S)-phenylsulfonylamino)propionate]-2-[2-(N-methylpiperidin-4-yl)ethyl]-3-oxo (17-4)

A solution of 17-3 (0.32 g, 1.02 mmol) and 22-3 (0.3 g, 1.02 mmol) in CH$_3$ CN (5 mL) was treated with N-methylmorpholine (0.22 mL, 2.04 mmol) and BOP reagent (0.45 g, 1.02 mmol). After 72 h the solution was concentrated and the residue chromatographed (5.02, 10% CH$_3$OH/CHCl$_3$ saturated with NH$_3$) to give 17-4 as a yellow solid. Rf (10% CH$_3$OH/CHCl$_3$ saturated with NH$_3$) 0.26

$^1$H NMR (300 MHz, CDCl$_3$) δ 8.13 (s, 1H), 8.06 (d, 1H), 7.85 (d, 2H), 7.5 (m, 4H), 7.1 (m, 1H), 4.42 (s, 2H), 4.18 (dd, 1H), 3.82 (dd, 1H), 3.7 (t, 2H), 3.62 (s, 3H), 2.89 (bd, 2H), 2.28 (s, 3H), 1.95 (m, 2H), 1.8 (m, 2H), 1.63 (m, 2H), 1.5-1.3 (m, 3H).

1-H-Isoindole-5-carboxamide, 2,3-dihydro-N-[3(2(S)-phenylsulfonylamino)propionate]-2-[2-N-methylpiperidin-4-yl)ethyl]-3-oxo (17-5)

A solution of 17-4 (0.19 g, 0.35 mmol) in 6N HCl was stirred for 20 h at room temperature and 40° C. for 1.5 h, then concentrated to give 17-5 as a yellow solid.

$^1$H NMR (300 MHz, CD$_3$OD) δ 8.0 (s, 1H), 7.8 (d, 1H), 7.7 (d, 2H), 7.53 (d, 1H), 7.3 (m, 3H), 4.47 (s, 2H), 4.1 (dd, 1H), 3.7-3.6 (m, 2H), 3.42-3.3 (m, 2H), 2.9-2.8 (m, 2H), 2.7 (s, 3H), 2.0 (bd, 2H), 1.7 (m, 2H), 1.5-1.3 (m, 3H).

1-H-Isoindole-5-carboxamide, 2,3-dihydro-N-[t-butyl, 3-propionate]-2-[2-N-methylpiperidin-4-yl]ethyl-3-oxo (17-6)

A solution of 17-3 (0.3 g, 1 mmol) in CH$_3$ CN (7 mL) was treated with t-Butyl β alanine hydrochloride (0.18 g, 1 mmol), N-methyl morpholine (0.22 mL, 2 mmol), and BOP reagent (0.44 g, 1 mmol). After 100 h the solution was concentrated and the residue chromatographed (SiO$_2$, 10:1:1 EtOH/NH$_4$OH/H$_2$O) to give 17-6 as an off-white solid.

$^1$H NMR (300 MHz, CDCl$_3$) δ 8.1 (m, 2H), 7.52 (d, 1H), 6.95 (m, 1H), 4.4 (s, 2H), 3.7 (m, 4H), 2.95 (bd, 2H), 2.6 (t, 2H), 2.32 (s, 3H), 2.0 (m, 2H), 1.9-1.8 (bd, 2H), 1.7-1.6 (m, 2H), 1.45 (s, 9H), 1.4 (m, 3H).

1-H-Isoindole-5-carboxamide, 2,3-dihydro-N-[3-propionate]-2-[2-N-methylpiperidin-4-yl]ethyl-3-oxo (17-7)

A solution of 17-6 (0.38 g) was cooled to −40° C. and saturated with HCl gas. The solution was warmed to 0° C. for 4 h, then concentrated to give a greenish residue, which was purified (10:0.3:0.3 EtOH/NH$_4$OH/H$_2$O) to give 17-7 as a white solid.

Rf (10:1: 1 EtOH/H$_2$O/NH$_4$OH) 0.59

$^1$H NMR (400 MHz, CD$_3$OD) δ 8.2 (s, 1H), 8.1 (d, 1H), 7.65 (d, 1H), 4.6 (s, 2H), 3.68 (m, 4H), 3.45 (d, 2H), 2.9 (m, 2H), 2.8 (s, 3H), 2.58 (m, 2H), 2.05 (bd, 2H), 1.7 (m, 2H), 1.5 (m, 3H).

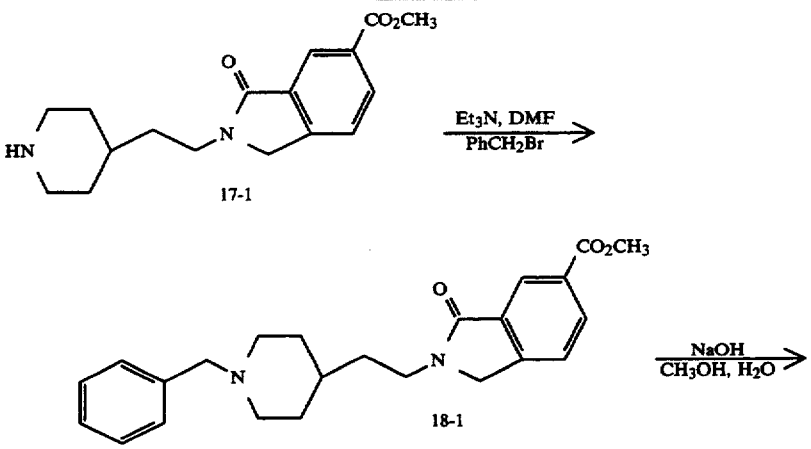

SCHEME 18

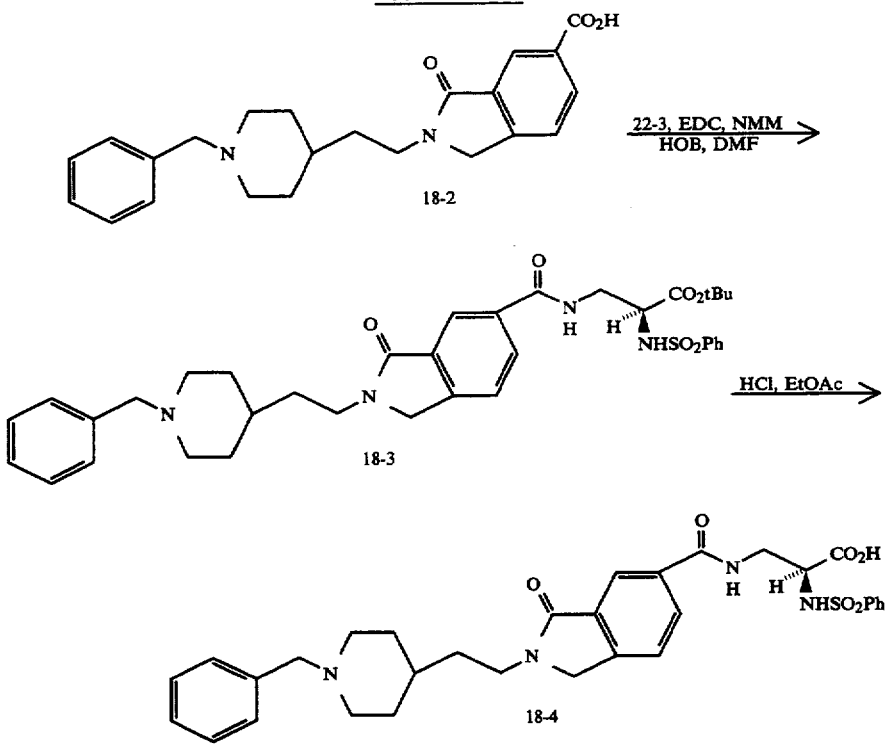

Methyl 1-H-Isoindole-5-carboxylate, 2,3-dihydro-2-[2-(N-benzylpiperidin-4-yl)ethyl]-3-oxo (18-1)

A suspension of 17-1 (0.85 g, 2.5 mmol) in DMF (20 mL) was treated with triethylamine (0.69 mL, 5 mmol) and benzyl bromide (0.43 g, 2.5 mmol). After 20 h the DMF was removed under vacuum and the residue was dissolved in H$_2$O, basified to pH 8–9 with saturated NaHCO$_3$ and extracted with EtOAc. The organic layer was washed with brine, dried over Na$_2$SO$_4$, filtered and evaporated to give 18-1 as a tan solid.

R$_f$(5% CH$_3$OH/CHCl$_3$) 0.22

$^1$H NMR (300 MHz, CDCl$_3$) δ 8.5 (s, 1H), 8.22 (d, 1H), 7.51 (d, 1H), 7.3-7.2 (m, 5H), 4.4 (s, 2H), 3.92 (s, 3H), 3.65 (t, 2H), 3.5 (b, 2H), 2.88 (bd, 2H), 1.95 (m, 2H), 1.7 (m, 2H), 1.6 (m, 2H), 1.4 (m, 3H).

1-H-Isoindole-5-carboxamide, 2,3-dihydro-N-[t-butyl, 3(2(S)-phenylsulfonylamino)propionate]-2-[2-(N-benzylpiperidin-4-yl)ethyl]-3-oxo (18-3)

A solution of 18-2 (1.0 g, 2.5 mmol) in CH$_3$OH (20 mL) was treated with 1N NaOH (5.1 mL, 5 mmole) for 20 h. The solvent was evaporated and the residue was chromatographed (SiO2, 5% NH$_4$OH/Isopropanol, followed by 10:1:1 EtOH/H$_2$/NH$_4$OH) to give 18-2 as a pale yellow solid.

A solution of 18-2 (0.76 g, 2 mmol) in DMF (20 mL) was treated with 22-3 (0.674 g, 2 mmol), HOBt (0.297 g, 2.2 mmol), N-methyl morpholine (0.66 mL, 6 mmol) and EDC (0.46 g, 2.4 mmol) and stirred overnight. The solvent was removed in vacuo, the residue dissolved in 100 mL H$_2$O, and extracted with EtOAc. The organic layer was extracted with saturated NaHCO$_3$ and brine, dried (Na$_2$SO$_4$), filtered and evaporated. Chromatography (SiO$_2$, 5% CH$_3$OH/CHCl$_3$) gave 18-3 as a foam.

R$_f$(10% CH$_3$OH/CHCl$_3$) 0.36

$^1$H NMR (300 MHz, CDCl$_3$) δ 8.17 (s, 1H), 8.04 (d, 1H), 7.85 (d, 2H), 7.5 (m, 3H), 7.3 (m, 5H), 7.05 (m, 1H), 5.95 (b, 1H), 4.39 (s, 2H), 4.0 (m, 1H), 3.86 (m, 1H), 3.7-3.6 (m, 3H), 3.55 (b, 2H), 2.94 (m, 2H), 2.0 (b, 2H), 1.75 (m, 2H), 1.6 (m, 2H), 1.4 (m, 1H), 1.29 (s, 9H).

1-H-Isoindole-5-carboxamide, 2,3-dihydro-N-[3(2(S)-phenylsulfonylamino)propionate]-2-[2-(N-benzylpiperidin-4-yl)ethyl]-3-oxo (18-4)

A solution of 18-3 (0.39 g, 0.6 mmol) in EtOAc (25 mL) was cooled to −25° C. and saturated with HCl gas. The solution was warmed to 0° C. for 1 h, then degassed with argon and concentrated to give 18-4 as a white solid.

R$_f$(10:1:1 EtOH/H$_2$O/NH$_4$OH) 0.75 $^1$H NMR (300 MHz, CD$_3$OD) δ 8.7 (m, 1H), 8.11 (s, 1H), 8.02 (d, 1H), 7.82 (d, 2H), 7.65 (d, 1H), 7.5-7.4 (m, 5H), 4.58 (s, 2H), 4.27 (s, 2H), 4.23 (dd, 1H), 3.8-3.7 (m, 3H), 3.5 (m, 3H), 2.98 (m, 2H), 2.1 (bd, 2H), 1.7 (m, 2H), 1.6-1.4 (m, 3H).

SCHEME 19

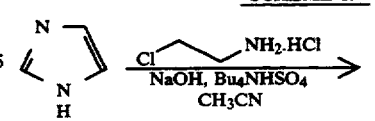

SCHEME 19 (continued)

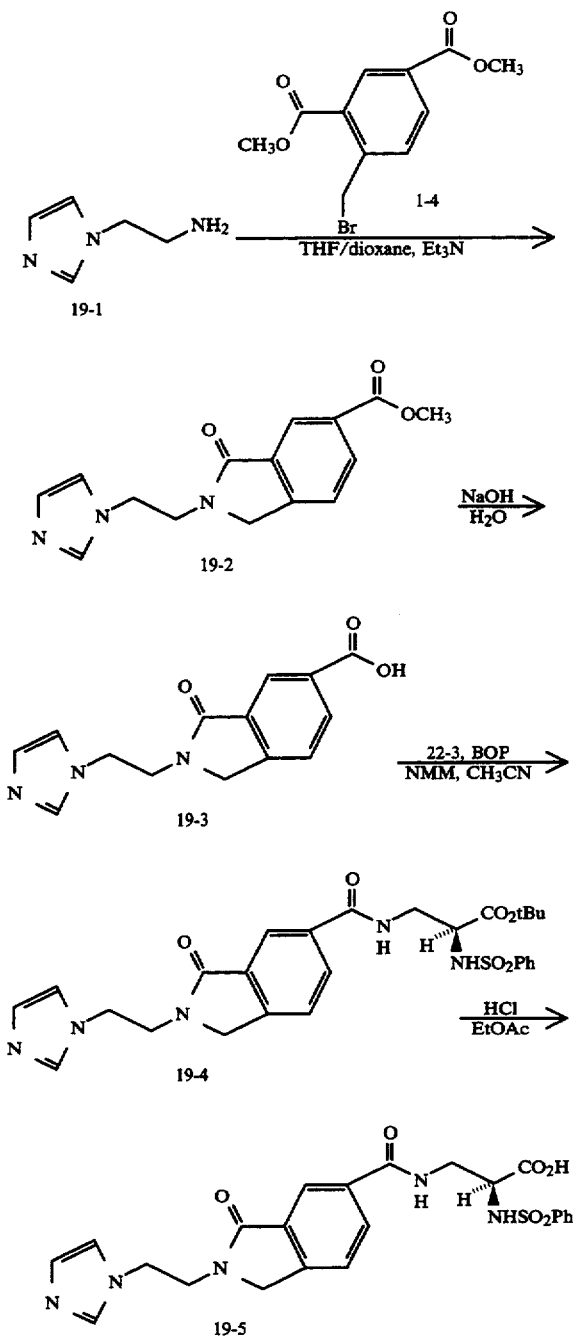

2-(Imidazole) ethylamine hydrobromide (1.9-1).

A mixture of imidazole (5.23 g, 76.8 mmol) and NaOH (9.48 g, 237 mmol)in acetonitrile (35 mL) was stirred at room temperature for 0.5 h. Tetra-butyl ammonium hydrogen sulfate (0.896 g, 2.64 mmol) and 2-chloroethylamine monohydrochloride (5.64 g, 70.9 mmol) were added and the mixture was heated to 80° C. After 20 h the reaction was cooled, the solid was removed by filtration and the filtrate was concentrated to give an orange oil, which was treated with an excess of HBr and concentrated to give an off-white solid. This solid was triturated with EtOH to give 19-1 as a white solid.

$R_f$ (10:1:1 EtOH/H$_2$O/NH$_4$OH) 0.59 $^1$H NMR (300 MHz, DMSO-d$_6$) δ 9.14 (s, 1H), 8.0 (b, 2H), 7.78 (m, 1H), 4.45 (t, 2H), 3.4-3.3 (b, 3H).

Methyl 1-H-Isoindole-5-carboxylate, 2,3-dihydro-2-[2(1-imidazole)ethyl]-3-oxo (19-2)

A solution of 19-1 (1.98 g, 10.4 mmol) in 1:1 THF/dioxane (50 mL) was treated with 1-4 (3 g, 10.4 retool) and triethylamine (4.25 mL, 30 mmol), heated to reflux for 3 h, then stirred at room temperature for 20 h. The mixture was concentrated and chromatographed (SiO$_2$, 10:0.5:0.5 CHCl$_3$/MeOH/NH$_4$OH) to give 19-2 as a light brown solid.

$R_f$ (10% CH$_3$OH/CHCl$_3$ saturated with NH$_3$) 0.54 $^1$H NMR (300 MHz, CD$_3$OD) δ 8.02 (s, 1H), 7.94 (d, 1H), 7.63 (m, 1H), 7.35 (m, 2H), 6.9 (s, 1H), 6.65 (s, 1H), 4.1 (m, 4H), 3.72 (t, 2H), 3.64 (s, 3H).

1-H-Isoindole-5-carboxylic acid, 2,3-dihydro-2-[2(1-imidazole)ethyl]-3-oxo (19-3)

A solution of 19-2 (2 g, 8.1 mmol) in H$_2$O (30 mL) was treated with 1N NaOH (8.1 mL, 8.1 mmol) for 65 h. The solution was concentrated to give 19-3 as an orange solid.

$R_f$(10:1:1 EtOH/H$_2$O/NH$_4$OH) 0.69

$^1$H NMR (300 MHz, CD$_3$OD) a 8.2 (s, 1H), 8.0-5 (m, 1H), 7.5 (s, 1H), 7.35 (d, 1H), 7.02 (s, 1H), 6.82 (s, 1H), 4.3-4.2 (m, 2H), 4.15 (s, 2H), 3.9-3.8 (m, 2H).

1H-Isoindole-5-carboxamide, 2,3-dihydro-N-[t-Butyl, 3(2(S)-phenylsulfonylamino)propionate]-2 [2-(1-imidazole)ethyl]-3-oxo (19-4)

An CH$_3$ CN (15 mL) solution of 19-3 (0.4 g, 1.5 mmol) and 2-3 (0.46 g, 1.5 mmol) was treated with N-methyl morpholine (0.33 mL, 3 mmol) and BOP reagent (0.66 g, 1.5 mmol). After stirring for 100 h, the solution was concentrated and the residue was chromatographed (SiO$_2$, 1-5% CH$_3$OH/CHCl$_3$ saturated with NH$_3$ gradient) to give 19-4 as an off-white solid.

Rf (10% CH$_3$OH/CHCl$_3$ saturated with NH$_3$) 0.31 $^1$H NMR (300 MHz, CDCl$_3$) δ 8.22 (s, 1H), 8.05 (d, 1H), 7.89 (d, 1H), 7.64 (s, 1H), 7.6-7.4 (m, 5H), 7.1 (s, 1H), 7.0 (s, 1H), 6.15 (bs, 1H), 4.38 (t, 2H), 4.05 (s, 2H), 3.98 (t, 2H), 3.9 (m, 1H), 3.8-3.7 (m, 1H), 1.3 (s, 9H).

1-H-Isoindole-5-carboxamide, 2,3-dihydro-N-[3-(2(S)-phenyl sulfonylamino)propionate]-2-[2-(1-imidazole)ethyl]-3-oxo (19-5)

A solution of 19-4 (0.15 g, 0.277 mmol) in EtOAc was cooled to -40° C. and saturated with HCl gas. The solution was warmed to 0° C. for 2 h, then concentrated to give 19-5 as a white solid.

1H NMR (400 MHz, CD$_3$OD) δ 8.28 (s,1H), 7.8-7.75 (m, 2H), 7.55 (d, 2H), 7.36 (d, 1H), 7.2 (s, 1H), 7.15 (m, 2H), 7.07 (s, 1H), 4.28 (s, 2H), 4.23 (t, 2H), 3.85 (dd, 1H), 3.3 (t, 2H), 3.48 (dd, 1H), 3.21 (dd, 1H).

SCHEME 20

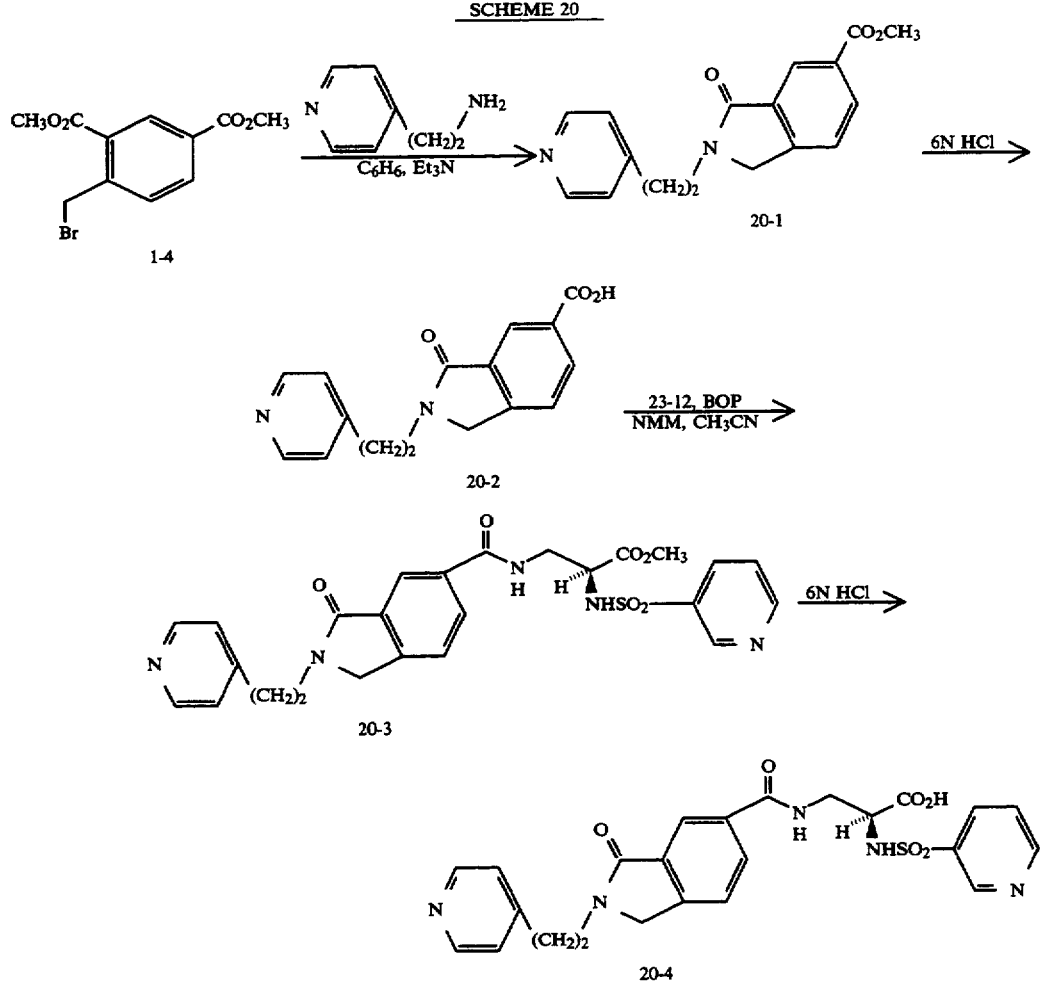

Methyl 1-H-Isoindole-5-carboxylate, 2,3-dihydro-2-[2-(4-pyridinyl)-ethyl]-3-oxo (20-1)

A solution of 1-4 (2.0 g, 6.9 mmol) in benzene (25 mL) was treated with 4-pyridine ethylamine (0.83 mL, 6.9 mmol) and triethylamine (0.98 mL, 6.9 mmol) and brought to reflux for 2 h. The solvent was removed and the residue was chromatographed ($SiO_2$, 50% acetone/hexanes) to give 20-1 as a white solid.

$^1$H NMR (400 MHz, $CD_3OD$) δ 8.4 (d, 2H), 8.33 (s, 1H), 8.23 (d, 1H), 7.65 (d, 1H), 7.47 (d, 2H), 4.54 (s, 2H), 3.94 (m, 5H), 3.09 (t, 2H).

1-H-Isoindole-5-carboxylic acid, 2,3-dihydro-2-[2-(4-pyridinyl)ethyl-3-oxo (20-2)

A solution of 20-1 (0.6 g, 2 mmol) in 6N HCl (6 mL) was stirred for 72 h at room temperature, then heated to 50° C. for 4 h. The solvent was removed to give 20-2 as a white solid.

$^1$H NMR (400 MHz, $CD_3OD$) δ 8.71 (d, 2H), 8.3 (s, 1H), 8.26 (d, 1H), 8.06 (d, 1H), 7.7 (d, 1H), 4.7 (s, 2H), 4.19 (t, 2H), 3.4 (t, 2H).

1-H-Isoindole-5-carboxamide, 2,3-dihydro-N-[Methyl, 3-[2(S)-(3-pyridyl)sulfonylamino)propionate]-2-[2-(4-pyridinyl)ethyl]-3-oxo (20-3)

A slurry of 20-2 (0.33 g, 1.07 mmol) and 23-12 (0.344 g, 1.04 mmol) in $CH_3CN$ (6 mL) was treated with N-methylmorpholine (0.47 mL, 4.28 mmol), and BOP reagent (0.473 g, 1.07 mmol). After 24 h the reaction was diluted with EtOAc, washed with $H_2O$ and brine, dried over $MgSO_4$, filtered and evaporated. The residue was chromatographed ($SiO_2$, 10% $CH_3OH/CHCl_3$) to give 20-3.

$^1$H NMR (400 MHz, $CD_3OD$) δ 8.92 (s, 1H), 8.61 (d, 1H), 8.41 (d, 2H), 8.21 (d, 1H), 8.04 (s, 1H), 8.0 (d, 1H), 7.84 (m, 1H), 7.64 (d, 2H), 7.51 (dd, 1H), 7.48 (d, 2H), 4.55 (s, 2H), 4.33 (m, 1H), 3.96 (t, 2H), 3.74 (dd, 1H), 3.59 (dd, 1H), 3.51 (s, 3H), 3.1 (t, 2H).

1-H-Isoindole-5-carboxamide, 2,3-dihydro-N-[3-(2-(3-pyridyl)sulfonylamino)propionate]-2-[2-(4-pyridyl)ethyl]-3-oxo (20-4)

Compound 20-3 (0.2 g, 0.38 mmol) was treated with 6N HCl for 72 h at room temperature followed by heating at 50° C. for 1 h. The solvent was removed and the residue was chromatographed ($SiO_2$, 10:1:1 EtOH/$H_2O$/$NH_4OH$) to give 20-4.

$R_f$ (10:1:1 EtOH/$H_2O$/$NH_4OH$) 0.25 $^1$H NMR (300 MHz, $D_2O$) δ 8.75 (s, 1H), 8.25 (d, 2H), 8.0 (d, 1H), 7.89 (d, 1H), 7.63 (d, 1H), 7.5 (s, 1H), 7.45 (d, 1H), 7.26 (d, 2H), 7.05 (dd, 1H), 4.4 (s, 2H), 3.91 (dd, 1H,), 3.83 (t, 2H), 3.61 (dd, 1H), 3.3 (dd, 1H), 3.0 (t, 2H).

SCHEME 21

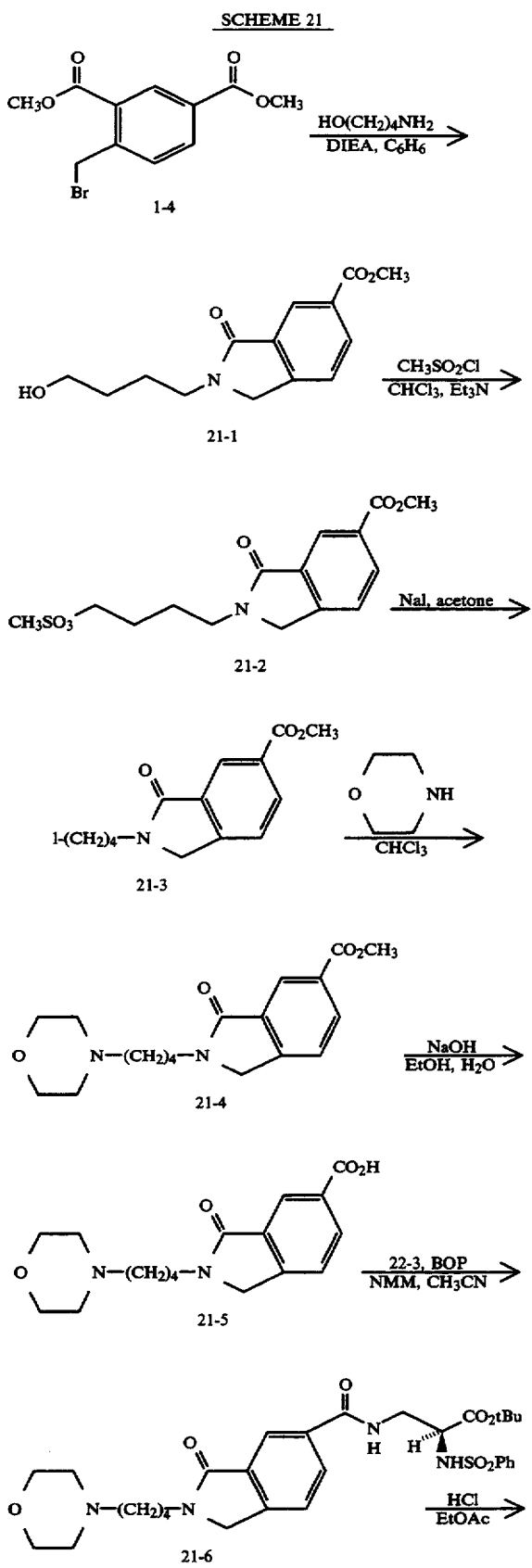

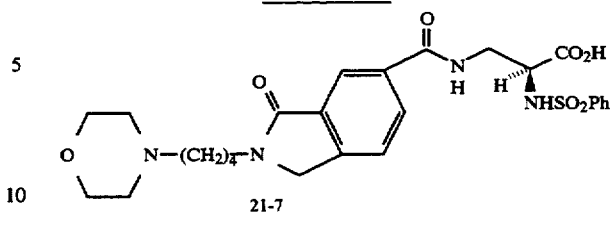

Methyl 1-H-Isoindole-5-carboxylate, 2,3-dihydro-2(4-hydroxybutyl)-3-oxo (21-1)

A solution of 1-4 (1.6 g, 5.6 mmol) in benzene (30 mL) was treated with 4-hydroxybutylamine (0.52 mL, 5.6 mmol) and diisopropylethylamine (1.96 mL, 11.2 mmol) and brought to reflux for 5 h and stirred at room temperature for 30 h. The reaction was concentrated. Chromatography (SiO$_2$, 3% CH$_3$OH/CHCl$_3$) gave 21-1 as a white solid.

R$_f$(20% CH$_3$OH/CHCl$_3$) 0.65

$^1$H NMR (400 MHz, CDCl$_3$) δ 8.5 (s, 1H), 8.23 (dd, 1H), 7.52 (d, 1H), 4.45 (s, 2H), 3.94 (s, 3H), 3.71 (m, 4H), 1.95 (b, 1H), 1.8 (m, 2H), 1.62 (m, 2H).

Methyl 1-H-Isoindole-5-carboxylate, 2,3-dihydro-2[4-(methanesulfonyloxy)butyl]-3-oxo (21-2)

A solution of 21-1 (1.1 g, 4.2 mmol) in CHCl$_3$ (30 mL) was cooled to 0° C. and treated with triethylamine (1.05 mL, 7.5 mmol) and methanesulfonyl chloride (0.33 mL, 4.8 mmol). After stirring for 2 h, the solution was washed with H$_2$O, 10% KHSO$_4$, brine, dried (MgSO$_4$), filtered and evaporated to give 21-2 as a tan solid.

R$_f$(10% CH$_3$OH/CHCl$_3$) 0.75

$^1$H NMR (300 MHz, CDCl$_3$) δ 8.52 (s, 1H), 8.29 (d, 1H), 7.56 (d, 1H), 4.49 (s, 2H), 4.32 (m, 2H), 3.98 (s, 3H), 3.72 (m, 2H), 3.04 (s, 3H), 1.86 (m, 4H).

Methyl 1-H-Isoindole-5-carboxylate, 2,3-dihydro-2[4-iodobutyl]-3-oxo (21-3)

A solution of 21-2 (1.0 g, 2.93 mmol) in acetone (20 mL) was treated with NaI (0.7 g, 4.4 mmol). After 3 h at room temperature the solution was heated to reflux for 3 h, then allowed to cool to room temperature and stir overnight. The mixture was filtered and the solid washed with acetone. The filtrate was concentrated and chromatographed (SiO$_2$, 40% EtOAc/Hexanes) to give 21-3 as a pale yellow solid.

R$_f$(40% EtOAc/Hexanes) 0.25

$^1$H NMR (300 MHz, CDCl$_3$) δ 8.53 (s, 1H), 8.27 (d, 1H), 7.56 (d, 1H), 4.49 (s, 2H), 3.98 (s, 3H), 3.7 (t, 2H), 3.28 (t, 2H), 1.95-1.8 (m, 4H).

Methyl 1-H-Isoindole-5-carboxylate, 2,3-dihydro-2[4-N-(morpholino) butyl]-3-oxo (21-4)

A solution of 21-3 (1.0 g, 2.7 mmol) in CHCl$_3$ (27 mL0 was added to 1.18 mL of morpholine (1.18 mL, 13.5 mmol) and the mixture was heated to reflux for 3 h, then concentrated. The residue was chromatographed (SiO$_2$, 10% CH$_3$OH/CHCl$_3$) to give 21-4.

R$_f$(10% CH$_3$OH/EthylAcetate) 0.19

$^1$H NMR (400 MHz, CD$_3$OD) δ 8.36 (s, 1H), 8.23 (d, 1H), 7.84 (d, 1H), 4.6 (s, 2H), 3.98 (s, 3H), 3.6 (m, 6H), 2.4 (m, 6H), 1.78 (m, 2H), 1.6 (m, 2H).

1-H-Isoindole-5-carboxylate, 2,3-dihydro-2[4-(N-morpholino)butyl]-3-oxo (21-5)

A solution of 21-4 (0.76 g, 2.3 mmol) in EtOH (11 mL0 was treated with 1N NaOH (2.3 mL, 2.3 mmol) for 120 h, then concentrated to give 21-5 as a white solid.

1H NMR (400 MHz, CD3OD) δ 8.35 (s, 1H), 8.28 (d, 1H), 7.55 (d, 1H), 4.52 (s, 2H), 3.7-3.6 (m, 6H0, 2.4 (m, 6H), 1.75 (m, 2H), 1.55 (m, 2H). 1-H-Isoindole-5-carboxyamide, 2,3-dihydro-N-[t-butyl, 3(2(S)phenylsulfonylamino)propionate]-2[4-N-morpholinobutyl]-3-oxo (21-6)

A solution of 21-5 (0.38 g, 1.19 mmol) in CH3CN (10 mL) was treated with 22-3 (0.36 g, 1.19 mmol), BOP reagent (0.53 g, 1.119 mmol), and N-methyl morpholine (0.26 mL, 2.38 mmol). After 90 h the solution was concentrated and the residue was chromatographed (SiO2, 5% CH3OH/CHCl3) to give 21-6 as a colorless oil.

1H NMR (400 MHz, CDCl3) δ 8.18 (s, 1H), 8.04 (d, 2H), 7.85 (d, 2H), 7.5 (m, 4H), 6.98 (m, 1H), 5.85 (m, 1H), 4.42 (s, 2H), 4.0 (m, 1H), 3.88 (m, 1H), 3.72-3.6 (m, 8H), 2.4 (m, 6H), 1.9 (b, 1H), 1.74 (m, 2H), 1.57 (m, 2H), 1.28 (s, 9H).

1H-Isoindole-5-carboxamide, 2.3-dihydro-N-[3(2(S)-phenylsulfonylamino)propionoate]-2[4-N-methylmorpholinobutyl]-3-oxo 21-7

A solution of 21-6 (0.35 g, 0.58 mmol) in EtOAc (6 mL) was cooled to −40° C. and saturated with HCl gas, then warmed to 0° C. and stirred for 2 h. The solution was concentrated, and the residue was filtered through a plug of silica gel (eluting with 10:1:1 EtOH/NH4OH/H2O) to give 21-7 as an off-white solid.

1H NMR (400 MHz, DMSO-d6, of HCl salt before filtration through silica gel plug) d 9.39 (m, 1H), 8.92 (d, 1H), 8.57 (s, 1H), 8.62 (d, 1H), 8.4 (d, 2H), 8.32 (1H), 8.18-8.03 (m, 3H), 5.2 (s, 2H), 4.7-4.6 (m, 2H), 4.58 (d, 2H), 4.27 (t, 2H), 4.2-4.0 (m, 5H), 3.78 (m, 2H), 3.63 (m, 2H), 2.3 (m, 2H), 1.9 (m, 2H).

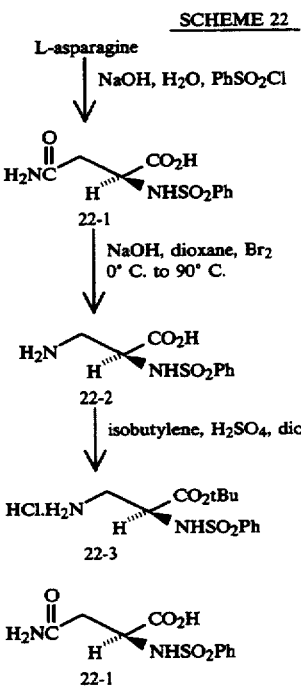

SCHEME 22

N-Phenysulfonyl-L-asparagine (22-1)

To a stirred solution of L-asparagine (Aldrich) (10 g, 76 mmol), NaOH (3.4 g, 85 mmol), H2O (50 mL), and dioxane (50 mL) at 0° C. was added PhSO2Cl (10.6 mL, 84 mmol). After 1 min, NaOH (3.4 g) in H2O (50 mL) was added and the reaction mixture stirred for 30 min. The reaction mixture was then concentrated to remove the dioxane then washed with EtOAc. The aqueous phase was then cooled to 0° C. and acidified to pH 3 with conc. HCl to effect product precipitation. The resulting solid was collected by filtration, washed with H2O (20 mL) and dried at 50° C. under vacuum to give 22-1 as a white solid.

Rƒ0.40 (silica, 10:1: 1 ethanol/H2O/NH4OH).

1H NMR (300 MHz, D2O) d 7.59 (m, 2H), 7.26 (m, 3H), 3.92 (m, 1H), 3.02 (m, 1H), 2.35 (m, 1H).

2(S)-Phenylsulfonylamino-3-aminopropionic acid (22-2)

To a stirred solution of NaOH (15.6 g, 0.4 mol) in H2O (70 mL), cooled with an icebath, was added bromine (3.6 mL, 0.07 mol) dropwise. After 5 min, a cold solution of 22-1 (14.6 g, 54 mmol) and NaOH (4.3 g, 0.1 mol) in H2O (50 mL) was added in one portion. The solution was stirred for 20 min at 0° C. then 30 min at 90° C. The reaction mixture was re-cooled to 0° C., and the pH adjusted to 7 through dropwise addition of conc. HCl. The white precipitate that formed was collected by filtration and dried to give 22-2 as a white solid. 1H NMR (300 MHz, D2O) δ 8.00-7.50 (m, 5H), 3.88 (m, 1H), 3.37 (m, 1H), 3.12 (m, 1H).

tert-Butyl 2(S)-Phenylsulfonylamino-3-aminopropionate hydrochloride (22-3)

In a Fischer-Porter tube, a mixture of 22-2 (102 g, 42 mmol) and DME (150 mL) was sequentially treated with H2SO4 (6.4 mL, 0.12 mol), cooled to −78° C., and then condensed isobutylene (75 mL). The cooling bath removed. After 2 h, ice-water (250 mL) was added followed by washing with ether (2×). The aqueous phase was basified with aq 5N NaOH, then saturated with NaCl, followed by extraction with EtOAc (3×). The combined extracts were washed with brine dried (MgSO4), and concentrated to give a white solid. This was dissolved in CHCl3 then treated with 1N HCl/ether (22 mL) then concentrated to give 22-3 as a glossy yellow solid.

1H NMR (400 MHz, DMSO) δ 8.25-8.00 (m, 4H), 7.85-7.58 (m, 5H), 4.08 (m, 1H), 3.10 (m, 1H), 2.73 (m, 1H), 1.17 (s, 9H).

SCHEME 23

2.Substituted-3-Aminopropionates are prepared in the following manner:

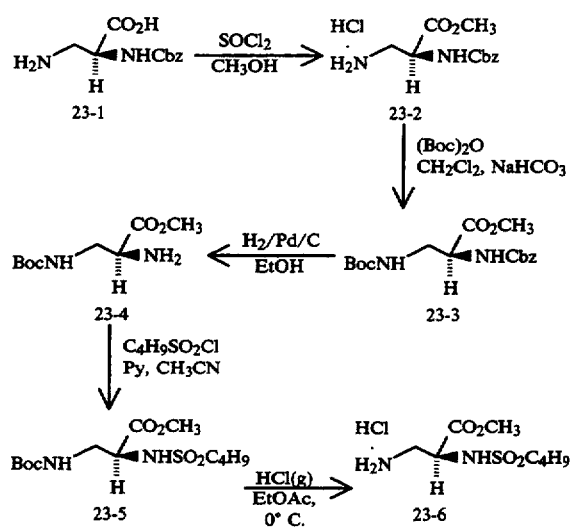

Methyl 2(S)-Benzyloxycarbonylamino-3-aminopropionate hydrochloride (23-2)

To a cooled suspension of 2(S)-benzyloxycarbonylamino-3-aminopropionic acid (Fluka) (23-1) (10 g, 0.042 mol) in 150 ml of methanol was added 5.47 g (0.046 mol) of thionyl chloride over 20 minutes. The resulting solution was allowed to stir at room temperature overnight. After ~18 hrs, the solvent was removed in vacuo, and the residual solid was stirred with 150 ml of ether for 0.5 hr. The resulting white solid was collected and air dried to give 23-2.

$^1$H NMR (300 MHz, CD$_3$OD) δ 3.26 (2H, m), 3.45 (1H, dd), 3.77 (3H, s), 4.25 (1H, m), 5.13 (2H, s), 7.37 (5H, m).

Methyl 2(S)-Benzyloxycarbonylamino-3-(N-t-butyloxycarbonyl)aminopropionate (23-3)

To a 2-phase mixture of CH$_2$Cl$_{12}$ (500 ml) and saturated NaHCO$_3$ solution (300 ml) was added 28.87 g (0.10 mol) of 23-2. After a few minutes, 21.83 g (0.10 mol) of di-t-butyldicarbonate was added in one portion and the resulting mixture was stirred at room temperature for 4 hrs. The CH$_2$Cl$_2$ layer was then separated from the aqueous layer, and the aqueous layer was extracted with 300 ml of CH$_2$Cl$_2$. The combined organic extracts were washed with brine, dried and the solvent removed in vacuo to provide the product as a viscous oil. Trituration of this oil with 300 ml of hexane gave 23-3 as a white solid, m.p. 85°–87°.

$^1$H NMR (300 MHz, CDCl$_3$) δ 1.42 (9H, s), 1.50 (4H, m), 1.62 (1H, m), 3.52 (2H, m), 3.75 (3H, s), 4.41 (1H, m), 4.83 (1H, m), 5.12 (2H, s), 5.78 (1H, m), 7.35 (5H, m).

Methyl 2(S)-Amino-3-(N-t-butyloxycarbonyl)aminopropionate (23-4)

To a solution of 6.60 g (0.0187 mol) 23-3 in 150 ml EtOH was added 0.5 g of 10% Pd/C. The resulting mixture was hydrogenated under balloon pressure at r.t. for 4 hrs. The catalyst was filtered off and the solvent removed in vacuo to provide 23-4 as a viscous oil.

$^1$H NMR (300 MHz, CDCl$_3$) δ 1.45 (9H, s), 1.49 (2H, m), 1.59 (2H, m), 3.25 (1H, m), 3.49 (1H, m), 3.58 (1H,m), 3.75 (3H, s), 5.03 (1H, m).

Methyl 2(S)-Butylsulfonylamino-3-(N-t-butylcarbonyl)aminopropionate (23-5)

To a solution of 0.400 g (0.00183 mol) of 23-4 in 10 ml of CH$_3$CN was added 0.226 g (0.00286 mol) pyridine followed by 0.408 g (0.0026 mol) of n-butanesulfonyl chloride. The resulting solution was stirred at room temperature for 2.5 hrs at which time starting material was consumed. The solvent was removed in vacuo and 50 ml of H$_2$O added to the residual material. This mixture was extracted with 3×50 ml portions of ethyl acetate and the combined extracts layer was dried (Na$_2$SO$_4$), filtered and concentrated to give 0.5 g of a viscous oil.

Trituration to this oil with 25 ml of hexane provided 23-5 as a white, amorphous solid.

$^1$H NMR (300 MHz, CDCl$_3$) δ 0.95 (3H, t), 1.43 (9H, s), 1.48 (2H, m), 1.80 (2H, m), 3.03 (2H, m), 3.52 (2H, t), 3.80 (3H, s), 4.22 (1H, m), 4.99 (1H, bt), 5.48 (1H, bd),

Methyl 2(S)-Butylsulfonylamino-3-aminopropionate hydrochloride (23-6)

A cooled (−20° C.) solution of 0.400 g (0.00118 mol) of 23-5 in 25 ml of ethyl acetate was treated with HCl gas for 15 min. The resulting solution was then stoppered and allowed to stir at 0° C. for an additional hour. The solvent and excess HCl were removed in vacuo to give 23-6 as a hygroscopic, yellowish foam.

$^1$H NMR (300 MHz, CDCl$_3$) δ 0.94 (3H, t), 1.44 (9H, s), 1.48 (2H, m), 1.80 (2H, m), 3.04 (2H, m), 3.53 (2H, bt), 3.80 (3H, s), 4.22 (1H, m), 4.93 (1H, m), 5.40 (1H, bd).

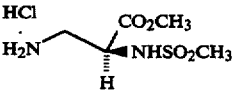

Methyl 2(S)-Methylsulfonylamino-3-aminopropionate hydrochloride (23-7)

23-7 was prepared as described above for the butylsulfonylamino analog (23-6) using methanesulfonyl chloride at the appropriate stage.

$^1$H NMR (300 MHz, CD$_3$OD) δ 3.07 (3H, s), 3.13 (1H, m), 3.43 (1H, dd), 3.83 (3H, s), 4.96 (1H, m).

Methyl 2(S)-Phenylsulfonylamino-3-(t-butyloxycarbonylamino)propionate acid (23-8)

A solution of 23-4 (19.6 g, 90.1 mmol) in CH$_2$Cl$_2$ (150 mL) was treated with benzenesulfonyl chloride (17.3 mL, 127 mmol) and pyridine (10.8 mL) as stirred overnight at room temperature. The solvent was removed in vacuo to give a yellow solid which was triturated with 1:1 hexanes/ether to give 23-8 as a white solid.

R$_f$ (30% EtOAc/Hexane) 0.22

¹H NMR (400 MHz, CDCl₃) δ 7.86 (d, 2H), 7.6 (m, 1H), 7.56 (m, 2H), 5.6 (bd, 1H), 4.92 (bs, 1H), 4.0 (m, 1H), 3.55 (s, 3H), 3.48 (m, 2H), 1.4 (s, 9H).

Methyl 2(S)-Phenylsulfonylamino-3-aminopropionate acid (23-9)

A solution of 23-8 (0.35 g, 0.98 mmol) in EtOAc (5 mL) was cooled to −40° C. and saturated with HCl gas. The solution was warmed to 0° C. for 2 h, then concentrated to give 23-9 as a white solid.

¹H NMR (400 MHz, CD₃OD) δ 7.95-7.90 (m, 2H), 7.7-7.5 (m, 3H), 4.22 (dd, 1H), 3.4 (dd, 1H), 3.12 (dd, 1H).

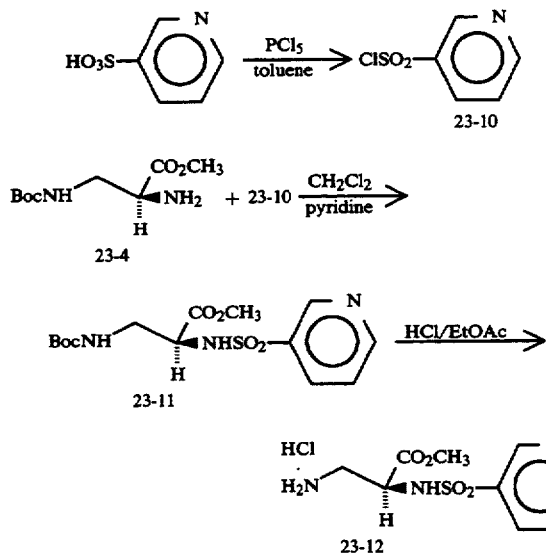

3-Pyridylsulfonyl chloride (23-10)

3-Pyridylsulfonic acid (30 g, 0.188 mole) was added to PCl₅ (46.8 g, 0.225 mole), suspended in 150 mL toluene and heated to reflux overnight. The suspension was cooled and concentrated to yield a yellow oil, which was diluted with benzene, filtered through a pad of celite and concentrated to give 30.7 g (92%) of 23-10 as a yellow oil, which was used in the next step without purification.

¹H NMR (300 MHz, CDCl₃) δ 9.27 (1H, s), 8.98 (1H, d, 8.35 (1H, d), 7.62 (1H, dd).

Methyl [2(S)-(3-Pyridylsulfonylamino)-3-(N-t-butyloxycarbonyl)amino]propionate (23-11)

Methyl 2(S)-amino-3-(N-t-butyloxycarbonyl)aminopropionate 23-4 (16.8 g, 0,077 mole) dissolved in 330 mL methylene chloride was treated with sulfonyl chloride 23-10 (20.6 g, 0.116 mole) and pyridine (12.5 mL, 0,154 mole) and the reaction was stirred for 21 hours. The reaction was concentrated, absorbed to silica and chromatographed with a gradient of 30%-70% acetone/hexanes to give crude 23-11 which was swished with hot EtOAc, cooled and filtered to give 23-11 as a pale yellow solid. R/0.29 (30% acetone/hexanes).

¹H NMR (300 MHz, CDCl₃) δ 9.0 (1H, s), 8.8 (1H, d), 8.6 (1H, d), 8.1 (1H, d), 7.45 (1H, dd), 7.3 (1H, m), 4.1 (1H, m), 4.1 (3H, s), 3.4–3.5 (2H, m), 1.4 (9H, s).

Methyl [2(S)-(3-Pyridylsulfonylamino)-3-aminolpropionate (23-12)

Methyl 2(S)-(3-pyridylsulfonyl)amino-3-(N-t-butyloxycarbonyl)aminopropionate 23-11 (17.5 g, 0,049 mole) was suspended in 200 mL EtOAc and cooled to −78° C. HCl gas was bubbled through the solution for ten minutes and the solution was then placed in an ice bath. After stirring for 40 minutes at 0° C., no starting material could be detected by TLC. The solution was concentrated, first at room temperature, then at 40° C. to yield 23-12 as an off-white solid.

R/0.34 (9:1:1 EtOH/H₂O/NH₄OH). ¹H NMR (300 MHz, CD₃OD) δ 9.3 (1H, s), 9.0 (1H, dd), 8.9 (1H, d), 8.2 (1H, dd), 4.6 (1H, dd), 3.6 (3H, s), 3.5 (1H, dd), 3.3 (1H, dd).

What is claimed is:
1. A compound of the following formula

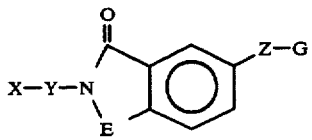

and pharmaceutically acceptable salts thereof, wherein G is

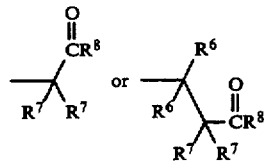

E is
—CH₂—or
—(C≡C)—,

X is a piperidinyl group either unsubstituted or substituted with R¹, R², R³, or R⁴, wherein R¹, R², R³, or R⁴, are independently selected from the group consisting of
hydrogen,
C₁₋₁₀ alkyl,
aryl C₀₋₈alkyl,
oxo,
thio,
amino C₀₋₈ alkyl, C₁₋₃ acylamino C₀₋₈ alkyl,
C₁₋₆ alkylamino C₀₋₈ alkyl,
C₁₋₆ dialkylamino C₀₋₈ alkyl,
C₁₋₄ alkoxy C₀₋₆ alkyl,
carboxy C₀₋₆ alkyl, C₁₋₃ alkoxycarbonyl C₀₋₆ alkyl,
carboxy C₀₋₆ alkyloxy and
hydroxy C₀₋₆ alkyl; or
a pyridinyl group either unsubstituted or substituted with R¹, R², R³, or R⁴, wherein R¹, R², R³, or R⁴, are independently selected from the group consisting of
hydrogen,
C₁₋₁₀ alkyl,
aryl C₀₋₈ alkyl,
oxo, thio,
amino $C_{0-8}$ alkyl, $C_{1-3}$ acylamino $C_{0-8}$ alkyl,
$C_{1-6}$ alkylamino $C_{0-8}$ alkyl,
$C_{1-6}$ dialkylamino $C_{0-8}$ alkyl,
$C_{1-4}$ alkoxy $C_{0-6}$ alkyl,
carboxy $C_{0-6}$ alkyl, $C_{1-3}$ alkoxycarbonyl $C_{0-6}$ alkyl,
carboxy $C_{0-6}$ alkyloxy and
hydroxy $C_{0-6}$ alkyl;

Y is
$C_{0-8}$ alkyl,
$C_{0-8}$ alkyl—$NR^3$—CO—$C_{0-8}$ alkyl,
$C_{0-8}$ alkyl—$CONR^3$—$C_{0-8}$ alkyl,
$C_{0-8}$ alkyl—O—$C_{0-8}$ alkyl,
$C_{0-8}$ alkyl—$SO_2$—$NR^3$—$C_{0-8}$ alkyl—,
$C_{0-8}$ alkyl—$NR^3$—$SO_2$—$(_{0-8}$ alkyl—,
$C_{1-8}$ alkyl—CO—$C_{0-8}$ alkyl;

Z is

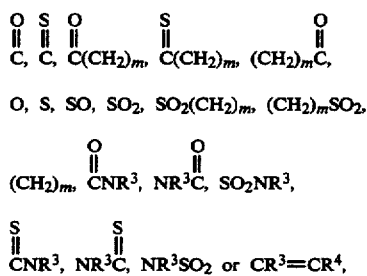

O, S, SO, $SO_2$, $SO_2(CH_2)_m$, $(CH_2)_mSO_2$, $(CH_2)_m$, $\overset{O}{\underset{\|}{C}}NR^3$, $NR^3\overset{O}{\underset{\|}{C}}$, $SO_2NR^3$, $\overset{S}{\underset{\|}{C}}NR^3$, $NR^3\overset{S}{\underset{\|}{C}}$, $NR^3SO_2$ or $CR^3=CR^4$, $R^6$ is
hydrogen;
$C_{1-8}$ alkyl,
aryl $C_{0-6}$ alkyl,
$C_{3-8}$ cycloalkyl $C_{0-6}$ alkyl, when two $R^6$ groups are attached to the same carbon, they may be the same or different;

$R^7$ is
hydrogen, fluorine
$C_{1-8}$ alkyl,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$-alkyl,
aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl
aryl $C_{0-6}$ alkylcarbonyl $C_{0-6}$ alkyl,
$C_{1-6}$ alkylthiocarbonylamino $C_{0-6}$ alkyl
aryl $C_{0-6}$ alkylthiocarbonylamino $C_{0-6}$ alkyl
wherein groups may be unsubstituted or substituted with one or more substituents selected from $R^1$ and $R^2$, and provided that when two $R^7$ groups are attached to the same carbon atom, they may be the same or different;

$R^8$ is
hydroxy,
$C_{1-8}$ alkyloxy,
aryl $C_{0-6}$ alkyloxy,
$C_{1-8}$ alkylcarbonyloxy $C_{1-4}$ alkyloxy, or
aryl $C_{1-8}$ alkylcarbonyloxy $C_{1-4}$ alkyloxy.

2. A compound of claim 1 selected from the group consisting of

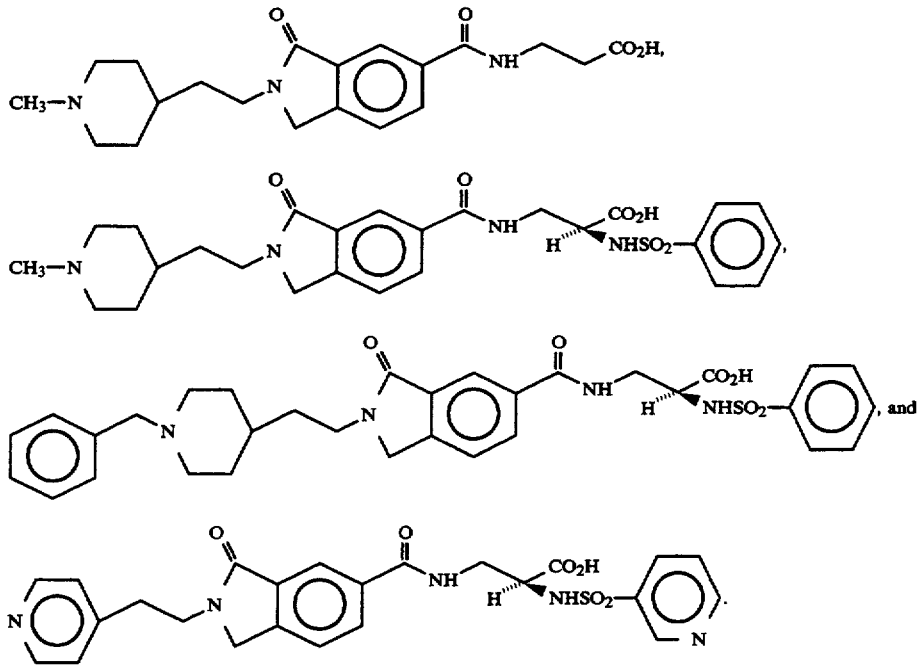

$C_{0-6}$ alkylcarboxy $C_{0-6}$ alkyl, carboxy $C_{0-6}$ alkyl,
$C_{1-4}$ alkyloxy $C_{0-6}$ alkyl,
hydroxy $C_{0-6}$ alkyl, provided that any of which groups may be substituted or unsubstituted independently with $R^1$ or $R^2$, and provided that, 3. A composition for inhibiting the aggregation of blood platelets in a mammal, comprising an antifibrinogen binding amount of a compound of claim 1 and pharmaceutically acceptable carrier.

4. A method for inhibiting the aggregation of blood platelets in a mammal, comprising administering to the mammal the composition of claim 3.

5. A compound of the following formula

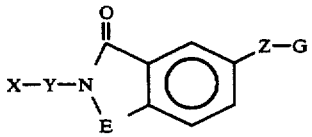

and pharmaceutically acceptable salts thereof, wherein G is

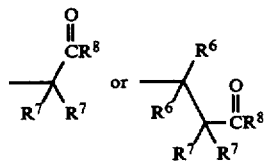

E is
- —CH$_2$—or
- —(C═C)—,

X is
a piperidinyl group either unsubstituted or substituted with R$^1$, R$^2$, R$^3$, or R$^4$, wherein R$^1$, R$^2$, R$^3$, or R$^4$, are independently selected from the group consisting of
hydrogen,
C$_{1-10}$ alkyl,
aryl C$_{0-8}$ alkyl,
oxo,
thio,
amino C$_{0-8}$ alkyl, C$_{1-3}$ acylamino C$_{0-8}$ alkyl,
C$_{1-6}$ alkylamino C$_{0-8}$ alkyl,
C$_{1-6}$ dialkylamino C$_{0-8}$ alkyl,
C$_{1-4}$ alkoxy C$_{0-6}$ alkyl,
carboxy C$_{0-6}$ alkyl, C$_{1-3}$ alkoxycarbonyl C$_{0-6}$ alkyl,
carboxy C$_{0-6}$ alkyloxy, and
hydroxy C$_{0-6}$ alkyl;

Y is
C$_{0-8}$ alkyl,
C$_{0-8}$ alkyl—NR$^3$—CO—C$_{0-8}$ alkyl,
C$_{0-8}$ alkyl-CONR$^3$—C$_{0-8}$ alkyl,
C$_{0-8}$ alkyl—O—C$_{0-8}$ alkyl,
C$_{0-8}$ alkyl—SO$_2$—NR$^3$—C$_{0-8}$ alkyl—,
C$_{0-8}$ alkyl—NR$^3$—SO$_2$—C$_{0-8}$ alkyl—,
C$_{1-8}$ alkyl—CO—C$_{0-8}$ alkyl;

Z is $$\overset{O}{\underset{}{\overset{\|}{C}}},\ \overset{S}{\underset{}{\overset{\|}{C}}},\ \overset{O}{\underset{}{\overset{\|}{C}}}(CH_2)_m,\ \overset{S}{\underset{}{\overset{\|}{C}}}(CH_2)_m,\ (CH_2)_m\overset{O}{\underset{}{\overset{\|}{C}}},$$

O, S, SO, SO$_2$, SO$_2$(CH$_2$)$_m$, (CH$_2$)$_m$SO$_2$, $$(CH_2)_m,\ \overset{O}{\underset{}{\overset{\|}{C}}}NR^3,\ NR^3\overset{O}{\underset{}{\overset{\|}{C}}},\ SO_2NR^3,$$

$$\overset{S}{\underset{}{\overset{\|}{C}}}NR^3,\ NR^3\overset{S}{\underset{}{\overset{\|}{C}}},\ NR^3SO_2\ or\ CR^3=CR^4,$$

wherein m is 0-6;
R$^6$ is
hydrogen,
C$_{1-8}$ alkyl,
aryl C$_{0-6}$ alkyl,
C$_{3-8}$ cycloalkyl C$_{0-6}$ alkyl,
C$_{0-6}$ alkylcarboxy C$_{0-6}$ alkyl, carboxy C$_{0-6}$ alkyl,
C$_{1-4}$ alkyloxy C$_{0-6}$ alkyl,
hydroxy C$_{0-6}$ alkyl, provided that any of which groups may be substituted or unsubstituted independently with R$^1$ or R$^2$, and provided that, when two R$^6$ groups are attached to the same carbon, they may be the same or different;

R$^7$ is
hydrogen, fluorine
C$_{1-8}$ alkyl,
C$_{3-8}$ cycloalkyl,
aryl C$_{0-6}$ alkyl,
C$_{0-6}$ alkylamino C$_{0-6}$ alkyl,
C$_{0-6}$ dialkylamino C$_{0-6}$ alkyl,
C$_{1-8}$ alkylsulfonylamino C$_{0-6}$ alkyl,
aryl C$_{0-6}$ alkylsulfonylamino C$_{0-6}$ alkyl,
C$_{1-8}$ alkyloxycarbonylamino C$_{0-8}$-alkyl,
aryl C$_{0-8}$ alkyloxycarbonylamino C$_{0-8}$ alkyl,
C$_{1-8}$ alkylcarbonylamino C$_{0-6}$ alkyl,
aryl C$_{0-6}$ alkylcarbonylamino C$_{0-6}$ alkyl,
C$_{0-8}$ alkylaminocarbonylamino C$_{0-6}$ alkyl,
aryl C$_{0-8}$ alkylaminocarbonylamino C$_{0-6}$ alkyl,
C$_{1-6}$ alkylsulfonyl C$_{0-6}$ alkyl,
aryl C$_{0-6}$ alkylsulfonyl C$_{0-6}$ alkyl,
C$_{1-6}$ alkylcarbonyl C$_{0-6}$ alkyl
aryl C$_{0-6}$ alkylcarbonyl C$_{0-6}$ alkyl,
C$_{1-6}$ alkylthiocarbonylamino C$_{0-6}$ alkyl
aryl C$_{0-6}$ alkylthiocarbonylamino C$_{0-6}$ alkyl
wherein groups may be unsubstituted or substituted with one or more substituents selected from R$^1$ and R$^2$, and provided that when two R7 groups are attached to the same carbon atom, they may be the same or different;

R$^8$ is
hydroxy,
C$_{1-8}$ alkyloxy,
aryl C$_{0-6}$ alkyloxy,
C$_{1-8}$ alkylcarbonyloxy C$_{1-4}$ alkyloxy, or
aryl C$_{1-8}$ alkylcarbonyloxy C$_{1-4}$ alkyloxy.

6. A compound of the following formula

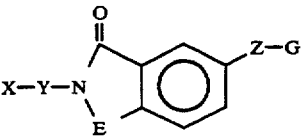

and pharmaceutically acceptable salts thereof, wherein G is

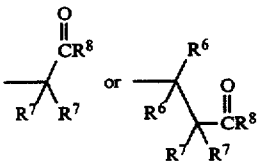

E is
- —CH$_2$—; or
- —(C═C)—,

X is a piperidinyl group;
Y is $C_{0-8}$ alkyl,
$C_{0-8}$ alkyl—$NR^3$—CO—$C_{0-8}$ alkyl,
$C_{0-8}$ alkyl—$CONR^3$—$C_{0-8}$ alkyl,
$C_{0-8}$ alkyl—O—$C_{0-8}$ alkyl,
$C_{0-8}$ alkyl—$SO_2$—$NR^3$—$C_{0-8}$ alkyl—,
$C_{0-8}$ alkyl—$NR^3$—$SO_2C_{0-8}$ alkyl—,
$C_{1-8}$ alkyl—CO—$C_{0-8}$ alkyl;

Z is $$\overset{O}{\underset{}{\overset{\|}{C}}}, \overset{S}{\underset{}{\overset{\|}{C}}}, \overset{O}{\underset{}{\overset{\|}{C}}}(CH_2)_m, \overset{S}{\underset{}{\overset{\|}{C}}}(CH_2)_m, (CH_2)_m\overset{O}{\underset{}{\overset{\|}{C}}},$$

O, S, SO, $SO_2$, $SO_2(CH_2)_m$, $(CH_2)_mSO_2$, $$(CH_2)_m, \overset{O}{\underset{}{\overset{\|}{C}}}NR^3, NR^3\overset{O}{\underset{}{\overset{\|}{C}}}, SO_2NR^3,$$

$$\overset{S}{\underset{}{\overset{\|}{C}}}NR^3, NR^3\overset{S}{\underset{}{\overset{\|}{C}}}, NR^3SO_2 \text{ or } CR^3{=}CR^4,$$

wherein m is 0–6;

$R^1$, $R^2$, $R^3$, or $R^4$, are independently selected from the group consisting of
  hydrogen,
  $C_{1-10}$ alkyl,
  aryl $C_{0-8}$ alkyl,
  oxo,
  thio,
  amino $C_{0-8}$ alkyl, $C_{1-3}$ acylamino $C_{0-8}$ alkyl,
  $C_{1-6}$ alkylamino $C_{0-8}$ alkyl,
  $C_{1-6}$ dialkylamino $C_{0-8}$ alkyl,
  $C_{1-4}$ alkoxy $C_{0-6}$ alkyl,
  carboxy $C_{0-6}$ alkyl, $C_{1-3}$ alkoxycarbonyl $C_{0-6}$ alkyl,
  carboxy $C_{0-6}$ alkyloxy, and
  hydroxy $C_{0-6}$ alkyl;

$R^6$ is
  hydrogen,
  $C_{1-8}$ alkyl,
  aryl $C_{0-6}$ alkyl,
  $C_{3-8}$ cycloalkyl $C_{0-6}$ alkyl,
  $C_{0-6}$ alkylcarboxy $C_{0-6}$ alkyl, carboxy $C_{0-6}$ alkyl,
  $C_{1-4}$ alkyloxy $C_{0-6}$ alkyl,
  hydroxy $C_{0-6}$ alkyl, provided that any of which groups may be substituted or unsubstituted independently with $R^1$ or $R^2$, and provided that, when two $R^6$ groups are attached to the same carbon, they may be the same or different;

$R^7$ is
  hydrogen, fluorine
  $C_{1-8}$ alkyl,
  $C_{3-8}$ cycloalkyl,
  aryl $C_{0-6}$ alkyl,
  $C_{0-6}$ alkylamino $C_{0-6}$ alkyl,
  $C_{0-6}$ dialkylamino $C_{0-6}$ alkyl,
  $C_{1-8}$ alkylsulfonylamino $C_{0-6}$ alkyl,
  aryl $C_{0-6}$ alkylsulfonylamino $C_{0-6}$ alkyl,
  $C_{1-8}$ alkyloxycarbonylamino $C_{0-8}$—alkyl,
  aryl $C_{0-8}$ alkyloxycarbonylamino $C_{0-8}$ alkyl,
  $C_{1-8}$ alkylcarbonylamino $C_{0-6}$ alkyl,
  aryl $C_{0-6}$ alkylcarbonylamino $C_{0-6}$ alkyl,
  $C_{0-8}$ alkylaminocarbonylamino $C_{0-6}$ alkyl,
  aryl $C_{0-8}$ alkylaminocarbonylamino $C_{0-6}$ alkyl,
  $C_{1-6}$ alkylsulfonyl $C_{0-6}$ alkyl,
  aryl $C_{0-6}$ alkylsulfonyl $C_{0-6}$ alkyl,
  $C_{1-6}$ alkylcarbonyl $C_{0-6}$ alkyl
  aryl $C_{0-6}$ alkylcarbonyl $C_{0-6}$ alkyl,
  $C_{1-6}$ alkylthiocarbonylamino $C_{0-6}$ alkyl
  aryl $C_{0-6}$ alkylthiocarbonylamino $C_{0-6}$ alkyl
wherein groups may be unsubstituted or substituted with one or more substituents selected from $R^1$ and $R^2$, and provided that when two R7 groups are attached to the same carbon atom, they may be the same or different;

$R^8$ is
  hydroxy,
  $C_{1-8}$ alkyloxy,
  aryl $C_{0-6}$ alkyloxy,
  $C_{1-8}$ alkylcarbonyloxy $C_{1-4}$ alkyloxy, or
  aryl $C_{1-8}$ alkylcarbonyloxy $C_{1-4}$ alkyloxy.

* * * * *